US006414139B1

(12) United States Patent
Unger et al.

(10) Patent No.: US 6,414,139 B1
(45) Date of Patent: Jul. 2, 2002

(54) SILICON AMPHIPHILIC COMPOUNDS AND THE USE THEREOF

(75) Inventors: Evan C. Unger; Dekang Shen; Guanli Wu, all of Tucson, AZ (US)

(73) Assignee: Imarx Therapeutics, Inc., Tucson, AZ (US)

(*) Notice: Subject to any disclaimer, the term of this patent is extended or adjusted under 35 U.S.C. 154(b) by 0 days.

(21) Appl. No.: 08/706,824

(22) Filed: Sep. 3, 1996

(51) Int. Cl.$^7$ .................................................. C07F 7/10
(52) U.S. Cl. .................. 536/413; 556/428; 556/437; 556/427; 556/436; 556/404; 556/405; 556/425
(58) Field of Search ................................ 556/413, 428, 556/437, 436, 404, 405, 425; 172/427

(56) References Cited

U.S. PATENT DOCUMENTS

| | | | |
|---|---|---|---|
| 3,015,128 A | 1/1962 | Sommerville et al. | 18/2.6 |
| 3,291,843 A | 12/1966 | Fritz et al. | 260/614 |
| 3,293,114 A | 12/1966 | Kenaga et al. | 162/168 |
| 3,479,811 A | 11/1969 | Walters | 57/153 |
| 3,488,714 A | 1/1970 | Walters et al. | 161/161 |
| 3,532,500 A | 10/1970 | Priest et al. | 96/91 |
| 3,557,294 A | 1/1971 | Dear et al. | 424/342 |
| 3,594,326 A | 7/1971 | Himmel et al. | 252/316 |
| 3,615,972 A | 10/1971 | Morehouse et al. | 156/79 |
| 3,650,831 A | 3/1972 | Jungermann et al. | 134/27 |
| 3,732,172 A | 5/1973 | Herbig et al. | 252/316 |
| 3,873,564 A | 3/1975 | Schneider et al. | 260/309.6 |
| 3,945,956 A | 3/1976 | Garner | 260/2.5 B |
| 3,960,583 A | 6/1976 | Netting et al. | 106/122 |
| 3,968,203 A | 7/1976 | Spitzer et al. | 424/47 |
| 4,027,007 A | 5/1977 | Messina | 424/46 |
| 4,089,801 A | 5/1978 | Schneider | 252/316 |
| 4,108,806 A | 8/1978 | Cohrs et al. | 521/54 |
| 4,138,383 A | 2/1979 | Rembaum et al. | 260/29.7 H |
| 4,162,282 A | 7/1979 | Fulwyler et al. | 264/9 |
| 4,179,546 A | 12/1979 | Garner et al. | 521/56 |
| 4,192,859 A | 3/1980 | Mackaness et al. | 424/5 |
| 4,224,179 A | 9/1980 | Schneider | 252/316 |
| 4,229,360 A | 10/1980 | Schneider et al. | 260/403 |
| 4,265,251 A | 5/1981 | Tickner | 128/660 |

(List continued on next page.)

FOREIGN PATENT DOCUMENTS

| | | |
|---|---|---|
| AU | 641363 | 3/1990 |
| AU | B-30351/89 | 3/1993 |
| DE | 25 21 003 | 8/1976 |
| DE | 3803972 | 8/1989 |
| EP | 0 052 575 | 5/1982 |
| EP | 0 107 559 | 5/1984 |
| EP | 0 077 752 B1 | 3/1986 |
| EP | 0 243 947 | 4/1987 |
| EP | 0 224 934 | 6/1987 |
| EP | 0 231 091 | 8/1987 |
| EP | 0 272 091 | 6/1988 |
| EP | 0 320 433 A2 | 12/1988 |
| EP | 0 324 938 | 7/1989 |
| EP | 0 338 971 | 10/1989 |
| EP | 357163 A1 | 3/1990 |
| EP | 0 359 246 | 3/1990 |
| EP | 0 361 894 | 4/1990 |
| EP | 0 216 730 | 1/1991 |
| EP | 0 467 031 A2 | 5/1991 |
| EP | 441468 A2 | 8/1991 |

(List continued on next page.)

OTHER PUBLICATIONS

Lindner et al., "Myocardial Perfusion Charcteristics and Hemodynamic Profile of MRX–115, a Venous Echocardiographic Contrast Agent, During Acute Myocardial Infarction", *J. Am. Soc. Echocardiography*, 1998, 11(1), 36–46.

Regen et al., "Polymerized Phosphatidylcholine Vesicles. Synthesis and Characterization", *J. Am. Chem. Soc.*, 1982, 104(3), 191–195.

Wei et al., "Quantification of Myocardial Blood Flow with Ultrasound–Induced Destruction of Microbubbles Administered as a Constant Venous Infusion", *Circulation*, 1998, 97, 473–483.

Hynynen et al., "The Usefulness of a Contrast Agent and Gradient Recalled Acquisition in a Steady–State Imaging Sequence for Magentic Resonance Imaging–Guided Noninvasive Ultrasound Surgery", *Investigative Radiology*, 1994, 29(10), 897–903.

Eibl, "Phospholipid synthesis: Oxazapholanes and dioxapholanes as intermediates", *Proc. Natl. Acad. Sci. USA*, 1978, 75(9), 4074–4077.

Hansen et al., "An Improved Procedure for the Synthesis of Choline Phospholipids via 2–Bromoethyl Dichlorophosphate", *Lipids*, 1982, 17(6), 453–459.

Hirt et al., "Zur Synthese der Phosphatide Eine neue Synthese der Lecithine", *Pharm. Acta. Helv.*, 1958, 33, 349–356 (Summary in English).

Santaella et al., "New Perfluoroalkylated Phospholipids as Injectable Surfactants: Synthesis, Preliminary Physicochemical and Biocompatibility Data", *New J. of Chem.*, 1991, 15, 685–692.

Simons, "Degradation of SFV in BHK21 Cells", *Biomembranes: Methods in Enzymology*, Part L—Membrane Biogenesis: Processing and Recycling, Sidney Fleischer and Becca Fleischer (eds.), 1983, 98, 263–264.

Villanueva et al., "Characterization of Spatial Patters of Flow Within the Reperfused Myocardium by Myocardial Contrast Echocardiography", *Circulation*, vol. 88, No. 6, pp. 2596–2606 (Dec. 1993).

(List continued on next page.)

*Primary Examiner*—Paul F. Shaver
(74) *Attorney, Agent, or Firm*—Woodcock Washburn

(57) ABSTRACT

Novel silicon amphiphilic compounds which comprise a silicon residue. The silicon amphiphilic compounds are particularly suitable for use in compositions for diagnostic imaging, such as ultrasound. Compositions of the silicon amphiphilic compounds comprise a gas or gaseous precursor, and may take the form of vesicle compositions, such as micelles or liposomes.

122 Claims, No Drawings

U.S. PATENT DOCUMENTS

| | | | |
|---|---|---|---|
| 4,276,885 A | 7/1981 | Tickner et al. | 128/660 |
| 4,310,505 A | 1/1982 | Baldeschwieler et al. | 424/1 |
| 4,310,506 A | 1/1982 | Baldeschwieler et al. | 424/1 |
| 4,315,514 A | 2/1982 | Drewes et al. | 128/653 |
| 4,331,654 A | 5/1982 | Morris | 424/38 |
| 4,342,826 A | 8/1982 | Cole | 435/7 |
| 4,344,929 A | 8/1982 | Bonsen et al. | 424/15 |
| 4,420,442 A | 12/1983 | Sands | 264/13 |
| 4,421,562 A | 12/1983 | Sands et al. | 106/75 |
| 4,426,330 A | 1/1984 | Sears | 260/403 |
| 4,427,649 A | 1/1984 | Dingle et al. | 424/38 |
| 4,428,924 A | 1/1984 | Millington | 424/4 |
| 4,442,843 A | 4/1984 | Rasor et al. | 128/660 |
| 4,466,442 A | 8/1984 | Hilmann et al. | 128/653 |
| 4,485,193 A | 11/1984 | Rubens et al. | 521/58 |
| 4,530,360 A | 7/1985 | Duarte | 128/419 F |
| 4,533,254 A | 8/1985 | Cook et al. | 366/176 |
| 4,534,899 A | 8/1985 | Sears | 260/403 |
| 4,540,629 A | 9/1985 | Sands et al. | 428/402 |
| 4,544,545 A | 10/1985 | Ryan et al. | 424/1.1 |
| 4,549,892 A | 10/1985 | Baker et al. | 65/21.4 |
| 4,569,836 A | 2/1986 | Gordon | 424/1 |
| 4,572,203 A | 2/1986 | Feinstein | 128/661 |
| 4,586,512 A | 5/1986 | Do-huu et al. | 128/660 |
| 4,603,044 A | 7/1986 | Geho et al. | 424/9 |
| 4,615,879 A | 10/1986 | Runge et al. | 424/9 |
| 4,620,546 A | 11/1986 | Aida et al. | 128/660 |
| 4,646,756 A | 3/1987 | Watmough et al. | 128/804 |
| 4,657,756 A | 4/1987 | Rasor et al. | 424/9 |
| 4,658,828 A | 4/1987 | Dory | 128/660 |
| 4,663,161 A | 5/1987 | Mannino et al. | 424/89 |
| 4,675,310 A | 6/1987 | Chapman et al. | 514/6 |
| 4,681,119 A | 7/1987 | Rasor et al. | 128/660 |
| 4,684,479 A | 8/1987 | D'Arrigo | 252/307 |
| 4,689,986 A | 9/1987 | Carson et al. | 73/19 |
| 4,693,999 A | 9/1987 | Axelsson et al. | 514/174 |
| 4,718,433 A | 1/1988 | Feinstein | 128/660 |
| 4,728,575 A | 3/1988 | Gamble et al. | 428/402.2 |
| 4,728,578 A | 3/1988 | Higgins et al. | 428/462 |
| 4,731,239 A | 3/1988 | Gordon | 424/9 |
| 4,737,323 A | 4/1988 | Martin et al. | 264/4.3 |
| 4,774,958 A | 10/1988 | Feinstein | 128/660.01 |
| 4,775,522 A | 10/1988 | Clark, Jr. | 424/9 |
| 4,776,991 A | 10/1988 | Farmer et al. | 264/4.3 |
| 4,781,871 A | 11/1988 | West, III et al. | 264/4.3 |
| 4,789,501 A | 12/1988 | Day et al. | 252/645 |
| 4,790,891 A | 12/1988 | Halliday et al. | 149/2 |
| 4,822,534 A | 4/1989 | Lencki et al. | 264/4.3 |
| 4,830,858 A | 5/1989 | Payne et al. | 424/450 |
| 4,834,964 A | 5/1989 | Rosen | 424/9 |
| 4,844,882 A | 7/1989 | Widder et al. | 424/9 |
| 4,863,717 A | 9/1989 | Keana | 424/9 |
| 4,865,836 A | 9/1989 | Long, Jr. | 424/5 |
| 4,877,561 A | 10/1989 | Iga et al. | 264/4.3 |
| 4,893,624 A | 1/1990 | Lele | 128/399 |
| 4,895,719 A | 1/1990 | Radhakrishnan | 424/45 |
| 4,898,734 A | 2/1990 | Mathiowitz et al. | 424/426 |
| 4,900,540 A | 2/1990 | Ryan et al. | 424/9 |
| 4,918,065 A | 4/1990 | Stindl et al. | 514/179 |
| 4,919,895 A | 4/1990 | Heldebrant et al. | 422/129 |
| 4,921,706 A | 5/1990 | Roberts et al. | 424/450 |
| 4,927,623 A | 5/1990 | Long, Jr. | 424/5 |
| 4,933,121 A | 6/1990 | Law et al. | 264/4.3 |
| 4,938,947 A | 7/1990 | Nicolau et al. | 424/1.1 |
| 4,957,656 A | 9/1990 | Cerny et al. | 252/311 |
| 4,972,002 A | 11/1990 | Volkert | 521/120 |
| 4,981,692 A | 1/1991 | Popescu et al. | 424/422 |
| 4,984,573 A | 1/1991 | Leunbach | 128/653 |
| 4,985,550 A | 1/1991 | Charpiot et al. | 536/18.4 |
| 4,987,154 A | 1/1991 | Long, Jr. | 514/772 |
| 4,993,415 A | 2/1991 | Long | 128/653 A |
| 4,996,041 A | 2/1991 | Arai et al. | 424/9 |
| 5,000,960 A | 3/1991 | Wallach | 424/450 |
| 5,004,611 A | 4/1991 | Leigh | 424/450 |
| 5,008,050 A | 4/1991 | Cullis et al. | 264/4.3 |
| 5,008,109 A | 4/1991 | Tin | 424/422 |
| 5,013,556 A | 5/1991 | Woodle et al. | 424/450 |
| 5,019,370 A | 5/1991 | Jay et al. | 424/4 |
| 5,045,304 A | 9/1991 | Schneider et al. | 424/9 |
| 5,049,388 A | 9/1991 | Knight et al. | 424/450 |
| B14,229,360 A | 11/1991 | Schneider et al. | 260/403 |
| 5,078,994 A | 1/1992 | Nair et al. | 424/501 |
| 5,088,499 A | 2/1992 | Unger | 128/662.2 |
| 5,107,842 A | 4/1992 | Levene et al. | 128/662.02 |
| 5,114,703 A | 5/1992 | Wolf et al. | 424/5 |
| 5,123,414 A | 6/1992 | Unger | 128/654 |
| 5,135,000 A | 8/1992 | Akselrod et al. | 128/662.02 |
| 5,137,928 A | 8/1992 | Erbel et al. | 521/56 |
| 5,141,738 A | 8/1992 | Rasor et al. | 424/2 |
| 5,147,631 A | 9/1992 | Glajch et al. | 424/9 |
| 5,149,319 A | 9/1992 | Unger | 604/22 |
| 5,171,755 A | 12/1992 | Kaufman | 514/759 |
| 5,186,922 A | 2/1993 | Shell et al. | 128/654 |
| 5,190,766 A | 3/1993 | Ishihara | 424/489 |
| 5,190,982 A | 3/1993 | Erbel et al. | 521/56 |
| 5,192,549 A | 3/1993 | Barenolz et al. | 424/450 |
| 5,194,266 A | 3/1993 | Abra et al. | 424/450 |
| 5,195,520 A | 3/1993 | Schlief et al. | 128/660.02 |
| 5,196,183 A | 3/1993 | Yudelson et al. | 424/9 |
| 5,196,348 A | 3/1993 | Schweighardt et al. | 436/173 |
| 5,198,225 A | 3/1993 | Meybeck et al. | 424/450 |
| 5,205,287 A | 4/1993 | Erbel et al. | 128/632 |
| 5,205,290 A | 4/1993 | Unger | 128/653.4 |
| 5,209,720 A | 5/1993 | Unger | 604/22 |
| 5,213,804 A | 5/1993 | Martin et al. | 424/450 |
| 5,215,680 A | 6/1993 | D'Arrigo | 252/307 |
| 5,219,538 A | 6/1993 | Henderson et al. | 428/402.2 |
| 5,228,446 A | 7/1993 | Unger et al. | 128/662.02 |
| 5,230,882 A | 7/1993 | Unger | 424/9 |
| 5,247,935 A | 9/1993 | Cline et al. | 128/653.2 |
| 5,271,928 A | 12/1993 | Schneider et al. | 424/9 |
| 5,281,408 A | 1/1994 | Unger | 424/4 |
| 5,305,757 A | 4/1994 | Unger et al. | 128/662.02 |
| 5,310,540 A | 5/1994 | Giddey et al. | 424/9 |
| 5,315,997 A | 5/1994 | Widder et al. | 128/653.3 |
| 5,315,998 A | 5/1994 | Tachibana et al. | 128/660.01 |
| 5,316,771 A | 5/1994 | Barenholz et al. | 424/450 |
| 5,334,381 A | 8/1994 | Unger | 424/9 |
| 5,339,814 A | 8/1994 | Lasker | 128/653.4 |
| 5,344,930 A | 9/1994 | Riess et al. | 544/84 |
| 5,350,571 A | 9/1994 | Kaufman et al. | 424/9 |
| 5,352,435 A | 10/1994 | Unger | 424/9 |
| 5,354,549 A | 10/1994 | Klaveness et al. | 424/3 |
| 5,358,702 A | 10/1994 | Unger | 424/9 |
| 5,362,477 A | 11/1994 | Moore et al. | 424/9 |
| 5,362,478 A | 11/1994 | Desai et al. | 424/9 |
| 5,380,519 A | 1/1995 | Schneider et al. | 424/9 |
| 5,393,524 A | 2/1995 | Quay | 424/9 |
| 5,409,688 A | 4/1995 | Quay | 424/9 |
| 5,410,516 A | 4/1995 | Uhlendorf et al. | 367/7 |
| 5,413,774 A | 5/1995 | Schneider et al. | 424/9.51 |
| 5,425,366 A | 6/1995 | Reinhardt et al. | 128/662.02 |
| 5,433,204 A | 7/1995 | Olson | 128/661.08 |
| 5,442,083 A | 8/1995 | Kobayashi | 556/434 |
| 5,445,813 A | 8/1995 | Schneider et al. | 424/9.51 |
| 5,456,900 A | 10/1995 | Unger | 424/9.4 |
| 5,460,800 A | 10/1995 | Walters | 424/9.6 |
| 5,469,854 A | 11/1995 | Unger et al. | 128/662.02 |
| 5,470,582 A | 11/1995 | Supersaxo et al. | 424/489 |
| 5,485,839 A | 1/1996 | Aida et al. | 128/653.1 |
| 5,487,390 A | 1/1996 | Cohen et al. | 128/662.02 |

| | | | |
|---|---|---|---|
| 5,496,535 A | 3/1996 | Kirkland | 424/9.37 |
| 5,498,421 A | 3/1996 | Grinstaff et al. | 424/450 |
| 5,501,863 A | 3/1996 | Rössling et al. | 424/489 |
| 5,502,094 A | 3/1996 | Moore et al. | 524/145 |
| 5,505,932 A | 4/1996 | Grinstaff et al. | 424/9.3 |
| 5,508,021 A | 4/1996 | Grinstaff et al. | 424/9.322 |
| 5,527,521 A | 6/1996 | Unger | 424/93 |
| 5,529,766 A | 6/1996 | Klaveness et al. | 424/9.52 |
| 5,531,980 A | 7/1996 | Schneider et al. | 424/9.52 |
| 5,536,489 A | 7/1996 | Lohrmann et al. | 424/9.52 |
| 5,536,490 A | 7/1996 | Klaveness et al. | 424/9.52 |
| 5,540,909 A | 7/1996 | Schutt | 424/9.52 |
| 5,542,935 A | 8/1996 | Unger et al. | 604/190 |
| 5,545,396 A | 8/1996 | Albert et al. | 424/93 |
| 5,547,656 A | 8/1996 | Unger | 424/9.4 |
| 5,552,133 A | 9/1996 | Lambert et al. | 424/9.52 |
| 5,552,155 A | 9/1996 | Bailey et al. | 424/450 |
| 5,556,372 A | 9/1996 | Talish et al. | 601/2 |
| 5,556,610 A | 9/1996 | Yan et al. | 424/9.52 |
| 5,558,092 A | 9/1996 | Unger et al. | 128/660.03 |
| 5,558,094 A | 9/1996 | Quay | 128/662.02 |
| 5,558,853 A | 9/1996 | Quay | 424/9.5 |
| 5,558,854 A | 9/1996 | Quay | 424/9.52 |
| 5,558,855 A | 9/1996 | Quay | 424/9.5 |
| 5,558,856 A | 9/1996 | Klaveness et al. | 424/9.37 |
| 5,560,364 A | 10/1996 | Porter | 128/662.02 |
| 5,562,608 A | 10/1996 | Sekins et al. | 604/20 |
| 5,562,893 A | 10/1996 | Lohrmann | 424/9.52 |
| 5,565,215 A | 10/1996 | Gref et al. | 424/501 |
| 5,567,413 A | 10/1996 | Klaveness et al. | 424/9.51 |
| 5,567,414 A | 10/1996 | Schneider et al. | 424/9.52 |
| 5,567,765 A | 10/1996 | Moore et al. | 524/801 |
| 5,569,448 A | 10/1996 | Wong et al. | 424/9.45 |
| 5,569,449 A | 10/1996 | Klaveness et al. | 424/9.51 |
| 5,571,797 A | 11/1996 | Ohno et al. | 514/44 |
| 5,573,751 A | 11/1996 | Quay | 424/9.52 |
| 5,578,292 A | 11/1996 | Schneider et al. | 424/9.51 |
| 5,585,112 A | 12/1996 | Unger et al. | 424/450 |
| 5,593,680 A | 1/1997 | Bara et al. | 424/401 |
| 5,595,723 A | 1/1997 | Quay | 424/9.5 |
| 5,605,673 A | 2/1997 | Schutt et al. | 424/9.51 |
| 5,606,973 A | 3/1997 | Lambert et al. | 128/662.02 |
| 5,612,057 A | 3/1997 | Lanza et al. | 424/450 |
| 5,612,318 A | 3/1997 | Weichselbaum et al. | 514/44 |
| 5,614,169 A | 3/1997 | Klaveness et al. | 424/9.52 |
| 5,620,689 A | 4/1997 | Allen et al. | 424/178.1 |
| 5,626,833 A | 5/1997 | Schutt et al. | 424/9.52 |
| 5,639,443 A | 6/1997 | Schutt et al. | 424/9.52 |
| 5,639,473 A | 6/1997 | Grinstaff et al. | 424/450 |
| 5,643,553 A | 7/1997 | Schneider et al. | 424/9.52 |
| 5,648,095 A | 7/1997 | Illum et al. | 424/489 |
| 5,648,098 A | 7/1997 | Porter | 424/490 |
| 5,672,585 A | 9/1997 | Pierschbacher et al. | 514/11 |
| 5,676,928 A | 10/1997 | Klaveness et al. | 424/9.32 |
| 5,679,459 A | 10/1997 | Riess et al. | 428/402.2 |
| 5,686,060 A | 11/1997 | Schneider et al. | 424/9.52 |
| 5,686,102 A | 11/1997 | Gross et al. | 424/450 |
| 5,695,460 A | 12/1997 | Siegel et al. | 604/21 |
| 5,701,899 A | 12/1997 | Porter | 428/662.02 |
| 5,707,352 A | 1/1998 | Sekins et al. | 604/56 |
| 5,707,606 A | 1/1998 | Quay | 424/9.52 |
| 5,707,607 A | 1/1998 | Quay | 424/9.52 |
| 5,711,933 A | 1/1998 | Bichon et al. | 424/9.52 |
| 5,716,597 A | 2/1998 | Lohrmann et al. | 424/9.5 |
| 5,732,707 A | 3/1998 | Widder et al. | 128/661.08 |
| 5,733,527 A | 3/1998 | Schutt | 424/9.52 |
| 5,736,121 A | 4/1998 | Unger | 424/9.4 |
| 5,740,807 A | 4/1998 | Porter | 128/662.02 |
| 5,770,222 A | 6/1998 | Unger et al. | 424/450 |
| 5,804,162 A | 9/1998 | Kabalnov et al. | 424/9.51 |
| 5,840,023 A | 11/1998 | Oraevsky et al. | 600/407 |
| 5,855,865 A | 1/1999 | Lambert et al. | 424/9.52 |
| 5,858,399 A | 1/1999 | Lanza et al. | 424/450 |
| 5,874,062 A | 2/1999 | Unger | 424/9.4 |
| 5,897,851 A | 4/1999 | Quay et al. | 424/9.52 |
| 5,976,501 A | 11/1999 | Jablonski | 424/9.52 |

FOREIGN PATENT DOCUMENTS

| | | |
|---|---|---|
| EP | 0 357 164 B1 | 10/1991 |
| EP | 0 458 745 A1 | 11/1991 |
| EP | 0 314 764 B1 | 9/1992 |
| EP | 0 554 213 A1 | 8/1993 |
| EP | 0 586 875 | 3/1994 |
| EP | 0 614 656 A1 | 9/1994 |
| EP | 0 727 225 A2 | 8/1996 |
| EP | 0 901 793 A1 | 3/1999 |
| FR | 2 700 952 | 8/1994 |
| GB | 1044680 | 10/1966 |
| GB | 2193095 A | 2/1988 |
| JP | 62 286534 | 12/1987 |
| JP | SHO 63-60943 | 3/1988 |
| WO | WO 80/02365 | 11/1980 |
| WO | WO 82/01642 | 5/1982 |
| WO | US85/01161 | 3/1985 |
| WO | WO 85/02772 | 7/1985 |
| WO | WO 86/00238 | 1/1986 |
| WO | WO 86/01103 | 2/1986 |
| WO | WO 89/05040 | 6/1989 |
| WO | WO 90/01952 | 3/1990 |
| WO | WO 90/04384 | 5/1990 |
| WO | WO 90/04943 | 5/1990 |
| WO | WO 91/00086 | 1/1991 |
| WO | WO 91/03267 | 3/1991 |
| WO | WO 91/09629 | 7/1991 |
| WO | WO 91/12823 | 9/1991 |
| WO | WO 91/15244 | 10/1991 |
| WO | WO 92/10166 | 6/1992 |
| WO | WO 92/11873 | 7/1992 |
| WO | WO 92/15284 | 9/1992 |
| WO | WO 92/17212 | 10/1992 |
| WO | WO 92/17213 | 10/1992 |
| WO | WO 92/17436 | 10/1992 |
| WO | WO 92/17514 | 10/1992 |
| WO | WO 92/21382 | 10/1992 |
| WO | WO 92/22247 | 12/1992 |
| WO | WO 92/22249 | 12/1992 |
| WO | WO 92/22298 | 12/1992 |
| WO | WO 93/00933 | 1/1993 |
| WO | WO 93/05819 | 1/1993 |
| WO | WO 93/06869 | 4/1993 |
| WO | WO 93/13809 | 7/1993 |
| WO | WO 93/17718 | 9/1993 |
| WO | WO 93/20802 | 10/1993 |
| WO | WO 94/00110 | 1/1994 |
| WO | WO 94/06477 | 3/1994 |
| WO | WO 94/07539 | 4/1994 |
| WO | WO 94/09829 | 5/1994 |
| WO | WO 84/02909 | 8/1994 |
| WO | WO 94/16739 | 8/1994 |
| WO | WO 94/21301 | 9/1994 |
| WO | WO 94/21302 | 9/1994 |
| WO | WO 94/28780 | 12/1994 |
| WO | WO 94/28873 | 12/1994 |
| WO | WO 95/03835 | 2/1995 |
| WO | WO 95/06518 | 3/1995 |
| WO | WO 95/07072 | 3/1995 |
| WO | WO 95/23615 | 9/1995 |
| WO | WO 95/24184 | 9/1995 |
| WO | WO 95/32005 | 11/1995 |
| WO | WO 96/04018 | 2/1996 |
| WO | WO 96/09793 | 4/1996 |
| WO | WO 96/36286 | 11/1996 |

| WO | WO 96/40281 | 12/1996 |
| WO | WO 96/40285 | 12/1996 |
| WO | WO 98/00172 | 1/1998 |
| WO | WO 99/13919 | 3/1999 |

OTHER PUBLICATIONS

Desir et al., "Assessment of regional myocardial perfusion with myocardial contrast echocardiography in a canine model of varying degrees of coronary stenosis", *Am. Heart J.,* Jan., 1994, 127(1), 56–63.

Sekins et al., "Lung Cancer Hyperthermia via Ultrasound and PFC Liquids", *Published in Proceedings of 5th International Symposium on Hyperthermic Oncology,* Kyoto, Japan, Aug. 29–Sep. 3, 1998, 3 pages.

Pietersen, "A New Warning System for Fires of Electrical Origin", *CERN European Organization for Nuclear Research, Health and Safety Division,* Mar., 1977, 1–5.

Feinstein, Steven B., "Myocardial Perfusion Imaging: Contrast Echocardiography Today and Tomorrow," *Journal of the American College of Cardiology,* 8(1):251–253 (1986).

Keller et al., "The Behavior of Sonicated Albumin Microbubbles Within the Microcirulation: A Basis for Their Use During Myocardial Contrast Echocardiography", *Circulation Res.,* 65(2):458–465 (1989).

Lincoff et al., "Perfluoro–m–butane: A Gas for Maximum Duration Retinal Tamponade," *Arch Ophthalmology,* 101:460–462 (1983).

*Remington's Pharmaceutical Sciences,* John Hoover, managing ed., Mack Publishing Company, Easton, PA, pp. 295–298; 736; 1242–1244 (1975).

*Handbook of Pharmaceutical Excipients,* American Pharmaceutical Association, Washington, D.C. and The Pharmaceutical Society of Great Britain, London, England, pp. 181–183 (1986).

Barnhart et al., "Characteristics of Albunex™: Air–Filled Microspheres for Echocardiography Contrast Enhancement," *Investigative Radiology,* 25:S162–164.

Levene et al., "Characterization of Albunex™," *J. Acoust. Soc. Am.,* 87(Suppl.1):569–70.

Miller et al., "Physiochemical Approaches to the Mode of Action of General Anesthetics," *J. Amer. Soc. Anesthesiologists,* 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials,* 11:713–717 (1990).

PR Newswire, Apr. 1, 1986.

Swanson et al., Chapter 22, "Enhancement Agents for Ultrasound: Fundamentals", *Pharmaceuticals In Medical Imaging,* pp. 682–687 (1990).

Ophir et al., "Contrast Agents in Diagnostic Ultrasound", *Ultrasound in Med. & Biol.,* vol. 15, No. 4, pp. 319–333 (1989).

Jacobs, "Intraocular gas measurement using A–scan ultrasound", *Current Eye Research,* vol. 5, No. 8, pp. 575–578 (1986).

Chang et al., "Semipermeable Aqueous Microcapsules", *Canadian J. Of Phys. And Pharm.,* 1966, 44, 115–128.

Chang, "Semipermeable Microcapsules", *Science,* 1964, 146, 524–525.

Deasy, *Microencapsulation and Related Drug Processes,* 1983, vol. 20, Chs. 9 and 10, 195–240 (Marcel Dekker, Inc., NY).

Yeung et al., "Preparation of Microencapsulated Liposomes", *J. Microencapsulation,* 1988, 5, 331–337.

Mattrey et al., Gas Emulsions as Ultrasound Contrast Agents; Preliminary Results in Rabbits and Dogs, *Investigative Radiology,* vol. 29, June Supp. 2, pp. S139–S141, 1994.

Meltzer et al., Transmission of Ultrasonic Contrast Through the Lungs, *Ultrasound in Med. & Biol.,* vol. 7, No. 4, 377–384, 1981.

Lincoff et al., "Intravitreal Expansion of Perfluorocarbon Bubbles", *Arch. Ophthalmol.,* 1980, 98, 1646.

Lincoff et al., "Intravitreal Longevity of Three Perfluorocarbon Gases", *Arch. Ophthalmol.,* 1980, 98, 1610–1611.

Lincoff et al., "The Perfluorocarbon Gases in the Treatment of Retinal Detachment", *Ophthalmology,* 1983, 90(5), 546–551.

Gardner et al., "A Survey of Intraocular Gas Use in North America", *Arch. Ophthalmol.,* 1988, 106, 1188–1189.

Unger et al., "Liposomal MR Contrast Agents", *J. Liposome Research,* 1994, 4(2), 811–834.

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry,* vol. 13, No. 3, pp. 568–574 (1974).

Thanassi, "Aminomalonic Acid: Spontaneous Decarboxylation and Reaction with 5–Deoxypyridoxal", *Biochemistry,* vol. 9, No. 3, pp. 525–532 (1970).

Stelmashok et al., *Koordinatsionnaya Khimiya,* vol. 3, No. 4, pp. 524–527 (1977) (Russian and English language versions).

Mayhew et al., "High–Pressure Continuous–Flow System for Drug Entrapment in Liposomes", *Methods in Enzymology,* vol. 149, pp. 64–77 (1987).

Mayhew et al., "Characterization of Liposomes Prepared Using a Microemulsifier", *Biochimica et Biophysica Acta,* vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta,* 812:55–65 (1985).

Mayer et al., "Vesicles of Variable Size Produced by a Rapid Extrusion Procedure", *Biochimica et Biophysica Acta,* vol. 858, pp. 161–168 (1986).

Cheng, et al., "The Production and Evaluation of Contrast–Carrying Liposomes Made with an Automatic High Pressure System", *Investigative Radiology,* vol. 22, pp. 47–55 (1987).

Jain, et al., *Introduction to Biological Membranes,* Ch. 9, pp. 192–231 (J. Wiley and Sons, N.Y. 1980).

Sigel, H., ed., *Metal Ions in Biological Systems: Antibiotics and Their Complexes,* vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta,* vol. 986, pp. 200–206 (1989).

Hope et al., "Generation of Multilamellar and Unilamellar Phospholipid Vesicles", *Chemistry and Physics of Lipids,* vol. 40, pp. 89–107 (1986).

Mattrey et al., "Perfluorochemicals as US Contrast Agents for Tumor–Imaging and Hepatosplenography: Preliminary Clinical Results", *Radiology,* vol. 163, pp. 339–343 (1987).

Mattrey et al., "Prefluoroctylbromide: A Liver/Spleen–Specific and Tumor Imaging Ultrasound Contrast Material", *Radiology,* vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography,* vol. 114, No. 3, pp. 570–575 (1987).

Feinstein et al., "Two–Dimensional Contrast Echocardiography, I: In Vitro Development and Quantitative Analysis of Echo Contrast Agents", *JACC,* vol. 3, No. 1, pp. 14–20 (1984).

Ten Cate et al., "Two–Dimensional Contrast Echocardiography, II: Transpulmonary Studies", *JACC,* vol. 3, No. 1, pp. 21–27 (1984).

Unger et al., "Hepatic Metastases: Liposomal Gd–DTPA–enhanced MR Imaging", *Radiology,* vol. 171, pp. 81–85 (1989).

Deamer et al., "Permeability of Lipid Bilayers to Water and Ionic Solutes", *Chemistry and Physics of Lipids,* vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts,* 87:34772q (1977).

Scarpa et al., "Cation Permeability of Liposomes as a Function of the Chemical Composition of the Lipid Bilayers", *Biochimica et Biophysica Acta,* vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta,* vol. 597, pp. 193–198 (1980).

Tilcock et al., "Liposomal Gd–DTPA: Preparation and Characterization of Relaxivity", *Radiology,* vol. 171, pp. 77–80 (1989).

Mann et al., "Formation of Iron Oxides in Unilamellar Vesicles", *Journal of Colloid and Interface Science,* vol. 122, No. 2, pp. 326–335 (1988).

Anderson et al., "Manganese (III) Complexes in Oxidative Decarboxylation of Acids", *J. Am. Chem. Soc.,* vol. 92, No. 8, pp. 2450–2460 (1970).

Muhlradt et al., "Vitamin B6 Analogs: An Improved Synthesis of 5–Deoxypyridoxal", *New Compounds,* vol. 10, pp. 129–130 (1967).

Chapman D., "Physiochemical Properties of Phospholipids and Lipid Water Systems", *Liposome Technology,* Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.,* vol. 23, pp. S294–S297, Sep. 1988.

Fritzsch et al., "Preclinical and Clinical Results with an Ultrasonic Contrast Agent", *Inv. Rad.,* vol. 23, pp. S302–S305, Sep. 1988.

Brochure, *Experience,* Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.,* vol. 108, pp. 2321–2327 (1986).

Regen, "Polymerized Vesicles", *J. Am. Chem. Soc.,* vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol.* (*MOSC*), vol. 44(3), pp. 322–326 (1981) (abstract).

J. Vion–Dury et al., *J. Pharmacol. Exper. Ther.,* vol. 250(3), pp. 1113–1118 (1989) (abstract).

M.R. Zalutsky et al., *Invest. Radiol.,* vol. 22(2), pp. 141–147 (1987) (abstract).

Crowe et al., *Archives of Biochemistry and Biophysics,* vol. 242, pp. 240–247 (1985).

Crowe et al., *Archives of Biochemistry and Biophysics,* vol. 220, pp. 477–484 (1983).

Dorland's Illustrated Medical Dictionary, p. 946, 27th ed. (W.B. Saunders Company, Philadelphia 1988).

*Liposome Technology,* Gregoriadis, G., ed., vol. I, pp. 1–18, 29–35, 51–65 and 79–107 (CRC Press Inc., Boca Raton, FL, 1984).

Madden et al., *Chemistry and Physics of Lipids,* vol. 53, pp. 37–46 (1990).

Sinkula et al., *J. Pharm. Sci.,* vol. 64, pp. 181–210 (1975).

Shiina et al., "Hyperthermiaby Low–frequency Synthesized Ultrasound", *IEEE Engineering,* pp. 879–880, vol. 2 (1988) (abstract).

McAvoy et al., *IEEE Engineering, Ultrasonics Symposium Proceedings,* vol. 2, pp. 677–1248 (1989) (abstract).

Chapman et al., "Biomembrane Phase Transitions", *J. Biol. Chem.,* 1974, 249:2512–2521.

Hug et al., "Liposomes for the Transformation of Eukaryotic Cells", *Biochimica et Biophysica Acta,* 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.,* 1965, 13:238–252.

Carson et al., *Ultrasound in Med. & Biol.* 3, 1978, 341–350.

deGier et al., "Relations Between Liposomes and Biomembranes", *Annals of The New York Academy of Sciences,* 1978, 308:85–99.

Felgner et al., "Lipofection: A highly efficient, lipid–mediated DNA–transfection procedure", *Proc. Natl. Acad. Sci.,* 1987, 84:7413–7417.

Gabizon et al., "Liposome formulations with prolonged circulation time in blood and enhanced uptake by tumors", *Proc. Natl. Acad. Sci.,* 1988, 85:6949–6953.

Garelli, et al., *Biochimica et Biophysica Acta,* vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.,* 1991, 113:9027–9045.

*Mammalian Cell Biotechnology: A Practical Approach,* M. Butler, 1991 (Oxford University Press, New York), p. 57–70.

Mathiowitz et al., "Photochemical Rupture of Microcapsules: A Model System", *Journal of Applied Polymer Science,* 1981, 26:809–822.

May et al., "Cationic Liposomes Enable Bovine Herpesvirus Type 2 DNA to Infect Cells", *Acta virol.,* 1991, 35:107.

Poznansky et al., "Biologica Approaches to the Controlled Delivery of Drugs: A Critical Review", *Pharmacol, Rev.,* 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature,* 1992, 359:67–70.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE,* 1992, O–7803–0785, pp. 354–355.

Williams, "Human Gene Therapy: Searching for Better Vectors", *ASM News* [American Society for Microbology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science,* vol. 35, pp. 755–774 (1988).

Sankaram et al., "Cholesterol–Induced Fluid–Phase Immiscibility in Membranes", *Proc. Natl. Acad. Sci.,* vol. 88, pp. 8686–8690 (1991).

*Scientific Apparatus Catalog 92/93* (VWR Scientific, 1991), "Syringes", pp. 1511–1513; "Filtration, Syringe Filters", pp. 766–768; "Filtration, Membranes", pp. 750–753; "Filtration, Filter Holders", p. 744.

Gramiak et al., *Radiology,* "Detection of Intracardiac Blood Flow by Pulsed Echo–Ranging", pp. 415–418 (1971).

Feigenbaum et al., *Circulation,* "Identification of Ultrasound Echoes from the Left Ventricle by Use of Intracardiac Injections of Indocyanine Green", vol. XL1, pp. 615–621 (1970).

Santaella, et al., *FEBS 13463,* "Extended In Vivo Blood Circulation Time of Fluorinated Liposomes", vol. 336, No. 3, pp. 481–484 (1993).

Kost, et al., "Ultrasonic Modulated Drug Delivery Systems", *Polymers in Medicine II: Biomedical and Pharmaceutical Applications,* Chielline E. (ed.), (Plenum Press, New York and London), pp. 387–396.

Brown and Langer, *Annual Review Medicine,* 1988, 39:221 29, Annual Review, Inc., "Transdermal Delivery of Drugs", pp. 221–229.

Moseley, et al., *Microbubbles: A Novel MR Susceptibility Contrast Agent,* abstract, 1991 Napa, California Meeting of the Society for Magnetic Resonance in Medicine.

Ter–Pogossia Tomography, Kee, et al., n, "Physical Principles and Instrumentation", *Computed Body* eds., Raven Press, New York, Chapter 1, pp. 1–7 (1988).

Aronberg, "Techniques", *Computed Body Tomography,* Kee, et al., eds., Raven Press, New York, Chapter 2, pp. 9–36 (1988).

Miller, *Ultrasonics* (Sep. 1981), "Ultrasonic detection of resonant cavitation bubbles in a flow tube by their second–harmonic emissions," pp. 217–224.

Dittrich, "Cardiac Muscle Ischemia and Infarction", *The Second Annual International Symposium on Contrast Agents in Diagnostic Ultrasound,* Atlantic City, NJ (May 7, 1996) (abstract).

Pantely, "Intravenous Contrast Echocardiography–Tissue Imaging & Quantification of Coronary Blood Flow", *The Second Annual International Symposium on Contrast Agents in Diagnostic Ultrasound,* Atlantic City, NJ (May 7, 1996) (abstract).

Schutt et al., "Osmotically Stabilized Microbubble Sonographic Contrast Agents",*Acad. Radiol.,* vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta,* 1192, pp. 61–70 (1994).

Frézard, et al., "Fluorinated Phospholipid–Based Vesicles as Potential Drug Carriers: Encapsulation/Sustaining of Drugs and Stability in Human Serum",*Art, Cells, Blood Subs., and Immob. Biotech.,* 22(4), pp. 1403–1408 (1994).

Canfield et al., "Incorporation of β–Carotene into Mixed Micelles", *Methods in Enzymology,* 1990, 189, 418–422.

Elgorab et al., "Solubilization of β–Carotene and Retinol into Aqueous Solutions of Mixed Micelles", *Biochem. Biophys. Acta.,* 1973, 306, 58–66.

Shinoda, K., et al., "The Formation of Micelles", *Colloidal Surfactant,* Academic Press, New York, 1963, Chapter 1, 1–88.

Ulendorf, "Physics of Ultrasound Contrast Imaging: Scattering in the Linear Range", *IEEE Transactions on Ultrasonics, Ferroelectrics, and Frequency Control,* 1994, 41(1), 70–79.

Sutherland et al., "Color Doppler Myocardial Imaging: A New Technique for the Assessment of Myocardial Function", *J. Am. Soc of Echocardiogr,* 1994, 7(5), 414–458.

Fleischer, *Methods Enzymol,* 1983, 98, 263.

Hansen et al., *Lipids,* 1982, 17, 453.

Hirt et al., *Pharm. Acta. Helv.,* 1958, 33, 349.

Kawabata, K. et al., "Effect of second–harmonic superimposition on efficient induction of sonochemical effect", *Ultrasonics Sonochemistry,* 1966, 3, 1–5.

*Magnetic Resonance Imaging: Principles and Applications,* (William and Wilkins, Baltimore 1986).

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography,* 1998, 11(1), 36–46.

Regen et al., "Polymerized Phosphatidylcholine Vesicles. Synthesis and Characterization", *J. Am. Chem. Soc.,* 1982, 104(3), 191–195.

Wei et al., "Quantification of Myocardial Blood Flow with Ultrasound–Induced Destruction of Microbubbles Administered as a Constant Venous Infusion", *Circulation,* 1998, 97, 473–483.

Hynynen et al., "The Usefulness of a Contrast Agent and Gradient Recalled Acquisition in a Steady–State Imaging Sequence for Magnetic Resonance Imaging–Guided Noninvasive Ultrasound Surgery", *Investigative Radiology,* 1994, 29(10), 897–903.

Lejbkowicz et al., "The response of normal and malignant cells to ultrasound in vitro", Database *BIOSIS,* No. 1993:95122245 (abstract only).

Jackson et al., "Effect of ultrasound therapy on the repair of Achilles tendon injuries in rats", *Med. Sci. Sports Exercise,* 1991, 23(2), 171–176.

Maxwell, "Therapeutic Ultrasound: Its Effects on the Cellular and Molecular Mechanisms of Inflammation and Repair", *Physiotherapy,* 1992, 78(6), 421–426.

Tuncay et al., "Expression of Genes Associated with Tissue Remodeling Upon Ultrasound Perturbation in the Gingival Fibroblast", *J. Dental Res.,* 1996, 75, 143, (abstract only).

Wang et al., "Low Intensity Ultrasound Treatment Increases Strength in a Rat Femoral Fracture Model", *J. Orthopaedic Res.,* 1994, 12(1), 40–47.

Yang et al., "Exposure to Low–Intensity Ultrasound Increases Aggrecan Gene Expression in a Rat Femur Facture Model", *J. Orthopaedic Res.,* 1996, 14(5), 802–809.

Young et al., "Effect of therapeutic ultrasound on the healing of full–thickness excised skin lesions", *Ultrasonics,* 1990, 28(3), 175–180.

Young et al., "The Effect of Therapeutic Ultrasound on Angiogenesis", *Ultrasound Med. Biol.,* 1990, 16(3), 261–269.

Ding, X.C., "Scavenging effect of EDTA–fluorocarbon microspheres on 210 lead," *Chung Kuto Yao Li Hsueh Pao,* 1989, 10(5), 473–475 (abstract only).

Kinsler, L. E., et al., *Fundamentals of Acoustics,* $3^{rd}$ Ed., 1982, 228–331.

Meessen, H. (ed.), *Microcirculation,* Springer–Verlag, Berlin Heidelberg, New York, 1997, 44.

Ring, J., et al., "Humanalbuminunverträglichkeit: klinische und immunologische untersuchungen," *Clinical Weekly,* 1974, 52, 595–598.

Robinson, et al., F.J. Fry (ed.), "Ultrasound: its applications in medicine and biology," Elsevier Scientific Publishing Company, 1978, vol. 3, Chap. XI, 593–596.

Silbernagl, S., et al., "Pocket atlas of physiology," *Georg Thieme Verlag,* Stuttgart, New York, 1983, 156–157.

Wells, P.N.T., "Pulse–echo methods," *Biomedical Ultrasonics,* Academic Press, 1977, 209–220.

Porter, T. R., et al., "Thrombolytic Enhancement with Perfluorocarbon–exposed Sonicated Dextrose Albumin Microbubbles", *American Heart Journal,* Nov. 1996, vol. 132, No. 5, pp. 964–968.

Chortkoff, B.S. et al., "Pharmacokinetics Do Not Explain the Absence of an Anesthetic Effect of Perfluoropropane or Perfluoropenatane," *Anesth. Analg.,* 1994, 79, 234–237.

Sharma, S.K. et al., "Emulsification Methods For Perfluorchemicals," *Drug Develop. Indust Pharm.,* 1988, 14(15–17), 2371–2376.

Tilcock, C. et al., "PEG–coated Lipid Vesicles with Encapusulated Technetium–99m as Blood Pool Agents for Nuclear Medicine," *Nucl. Med. Biol.,* 1994, 21(2), 165–170.

Tilcock, C. et al., "$^{99m}$Tc–labeling of Lipid Vesicles Containing the Lipophilic Chelator PE–DTTA: Effect of Tin–to – chelate Ratio, Chelate Content and Surface Polymer on Labeling Efficiency and Biodistribution Behavior," *Nucl. Med. Biol.,* 1994, 21(2), 89–96.

Zarif, L.et al., "Synergistic Stabilization of Perfluorocarbon– Pluronic F–68 Emulsion by Perfluoroalkylated Polyhydroxylated Surfactants," *JAOCS,* 1989, 66(10), 1515–1523.

Hautanen, A., et al., "Effects of modifications of the RGD sequence and its context on recognition by the fibronectin receptor," *J. Biol. Chem.,* 1989, 264(3), 1437–1442.

Takeuchi, M. et al., "Enhanced visualization of intravascular thrombus with the use of a thrombus targeting ultrasound contrast agent (MRX408): Evidence from in vivo experimental echocardiographic studies," *J. Am. College of Cardiology,* 1998, 81(12), 1 page, Abstract XP–000952675.

Unger, E.C., et al., "In Vitrostudies of a new thrombus–specific ultrasound contrast agent," *J. of Cardiology,* 1998, 81(12), 58G–61G, Abstract XP–002087505.

Wu, Y., et al., "Binding and lysing of blood clots using MRX–408," *Investigate Radiology,* 1998, 33(12), 880–885.

Nomura et al., "US Contrast Enhancement of Hepatic Tumor with Helium Gas Microbubbles: A Preliminary Report", *Jpn. J. Med. Ultrasonics,* 1991, 18(5), (Japanese with English language abstract).

SILICON AMPHIPHILIC COMPOUNDS AND THE USE THEREOF

FIELD OF THE INVENTION

The present invention relates to novel amphiphilic compounds and the use thereof. More particularly, the present invention relates to novel silicon amphiphilic compounds and their use in diagnostic, therapeutic, and other applications.

BACKGROUND OF THE INVENTION

Ultrasound is a valuable diagnostic imaging technique for studying various areas of the body, for example, the vasculature, including tissue microvasculature. Ultrasound provides certain advantages. over other diagnostic techniques. For example, diagnostic techniques involving nuclear medicine and X-rays generally results in exposure of the patient to ionizing electron radiation. Such radiation can cause damage to subcellular material, including deoxyribonucleic acid (DNA), ribonucleic acid (RNA) and proteins. Ultrasound does not involve such potentially damaging radiation. In addition, ultrasound is relatively inexpensive relative to other diagnostic techniques, including computed tomography (CT) and magnetic resonance imaging (MRI), which require elaborate and expensive equipment.

Ultrasound involves the exposure of a patient to sound waves. Generally, the sound waves dissipate due to absorption by body tissue, penetrate through the tissue or reflect off of the tissue. The reflection of sound waves off of tissue, generally referred to as backscatter or reflectivity, forms the basis for developing an ultrasound image. In this connection, sound waves reflect differentially from different body tissues. This differential reflection is due to various factors, including the constituents and the density of the particular tissue being observed. Ultrasound involves the detection of the differentially reflected waves, generally with a transducer that. can detect sound waves having a frequency of 1 megahertz (MHZ) to 10 MHZ. The detected waves can be integrated into an image which is quantitated and the quantitated waves converted into an image of the tissue being studied.

Ultrasound imaging techniques generally also involve the use of contrast agents. Contrast agents are used to improve the quality and usefulness of images which are obtained via ultrasound. Exemplary contrast agents include, for example, suspensions of solid particles, emulsified liquid droplets, and gas-filled bubbles. See, e.g., Hilmann et al., U.S. Pat. No. 4,466,442, and published International Patent Applications WO 92/17212 and WO 92/21382.

The quality of images produced from ultrasound has improved significantly. Nevertheless, further improvement is needed, particularly with respect to images involving vasculature in tissues that are perfused with a vascular blood supply. Accordingly, there is a need for improved ultrasound techniques, including improved contrast agents which are capable of providing medically useful images of the vasculature and vascular-related organs.

The reflection of sound from a liquid-gas interface is extremely efficient. Accordingly, bubbles, including gas-filled bubbles, are useful as contrast agents. The term "bubbles", as used herein, refers to vesicles which are generally characterized by the presence of one or more membranes or walls surrounding an internal void that is filled with a gas or precursor thereto. Exemplary bubbles include, for example, vesicles which are surrounded by monolayers and/or bilayers to form, for example, unilamellar, oligolamellar and/or multilamellar vesicles, such as liposomes, micelles and the like. As discussed more fully hereinafter, the effectiveness of bubbles as contrast agents depends upon various factors, including, for example, the size and/or elasticity of the bubble.

With respect to the effect of bubble size, the following discussion is provided. As known to the skilled artisan, the signal which is reflected off of a bubble is a function of the radius ($r^6$) of the bubble (Rayleigh Scatterer). Thus, a bubble having a diameter of 4 micrometer ($\mu$m) possesses about 64 times the scattering ability of a bubble having a diameter of 2 $\mu$m. Thus, generally speaking, the larger the bubble, the greater the reflected signal.

However, bubble size is limited by the diameter of capillaries through which the bubbles must pass. Generally, contrast agents which comprise bubbles having a diameter of greater than 10 $\mu$m can be dangerous since microvessels may be occluded. Accordingly, it is preferred that greater than about 90% of the bubbles in a contrast agent have a diameter of less than about 10 $\mu$m, with greater than about 95% being more preferred, and greater than about 98% being even more preferred. Mean bubble diameter is important also, and should be greater than 1 $\mu$m, with greater than 2 $\mu$m being preferred. The volume weighted mean diameter of the bubbles should be about 7 to 10 micrometer.

As noted above, the elasticity of bubbles is also important. This is because highly elastic bubbles can deform, as necessary, to "squeeze" through capillaries. This decreases the likelihood of occlusion. The effectiveness of a contrast agent which comprises bubbles is also dependent on the bubble concentration. Generally, the higher the bubble concentration, the greater the reflectivity of the contrast agent.

Another important characteristic which is related to the effectiveness of bubbles as contrast agents is bubble stability. As used herein, particularly with reference to gas-filled bubbles, "bubble stability" refers to the ability of bubbles to retain gas entrapped therein after exposure to a pressure greater than atmospheric pressure. To be effective as contrast agents, bubbles generally need to retain greater than 50% of entrapped gas after exposure to pressure of 300 millimeters (mm) of mercury (Hg) for about one minute. Particularly effective bubbles retain 75% of the entrapped gas after being exposed for one minute to a pressure of 300 mm Hg, with an entrapped gas content of 90% providing especially effective contrast agents. It is also highly desirable that, after release of the pressure, the bubbles return to their original size. This is referred to generally as "bubble resilience."

Bubbles which lack desirable stability provide poor contrast agents. If, for example, bubbles release the gas entrapped therein in vivo, reflectivity is diminished. Similarly, the size of bubbles which possess poor resilience will be decreased in vivo, also resulting in diminished reflectivity.

The stability of bubbles disclosed in the prior art is generally inadequate for use as contrast agents. For example, the prior art discloses bubbles, including gas-filled liposomes, which comprise lipoidal walls or membranes. See, e.g., Ryan et al., U.S. Pat. Nos. 4,900,540 and 4,544,545; Tickner et al., U.S. Pat. No. 4,276,885; Klaveness et al., WO 93/13809 and Schneider et al., EPO 0 554 213 and WO 91/15244. The stability of the bubbles disclosed in the aforementioned references is poor in that as the solutions in which the bubbles are suspended become diluted, for example, in vivo, the walls or membranes of the bubbles are thinned. This results in a greater likelihood of rupture.

Various studies have been conducted in an attempt to improve bubble stability. Such studies have included, for example, the preparation of bubbles in which the membranes or walls thereof comprise materials that are apparently strengthened via crosslinking. See, e.g., Klaveness et al., WO 92/17212, in which there are disclosed bubbles which comprise proteins crosslinked with biodegradable crosslinking agents. Alternatively, bubble membranes can comprise compounds which are not proteins but which are crosslinked also with biocompatible compounds. See, e.g., Klaveness et al., WO 92/17436, WO 93/17718 and WO 92/21382.

Prior art techniques for stabilizing bubbles, including crosslinking, suffer from various drawbacks. For example, the crosslinking described above generally involves the use of new materials, including crosslinked proteins or other compounds, for which the metabolic fate is unknown. In addition, crosslinking requires additional chemical process steps, including isolation and purification of the crosslinked compounds. Moreover, crosslinking can impart rigidity to the membranes or walls of the bubbles. This results in bubbles having reduced elasticity and, therefore, a decreased ability to deform and pass through capillaries. Thus, there is a greater likelihood of occlusion of vessels with prior art contrast agents that are stabilized via crosslinking.

Since the early 1970's, bubbles, especially liposomes, have also been investigated repeatedly and intensively for their use as a delivery means for a wide variety of active agents including, for example, cosmetics, drugs, vitamins and biopolymers. Liposomes may have certain advantageous properties, such as non-toxicity, biodegradability and non-immunogenicity. Nevertheless, prior art liposomes generally suffer from drawbacks in that they may be relatively unstable in vivo and/or may be cleared quickly from the body by the reticuloendothelial system. Accordingly, little success has been achieved to date in connection with the use of liposomes as delivery agents of materials, such as active agents.

Accordingly, new and better amphiphilic compounds which can form stabilized contrast agents, as well as stabilized delivery means for active agents, and methods for providing same are needed. The present invention is directed to these, as well as other, important ends.

SUMMARY OF THE INVENTION

Broadly speaking, the present invention relates to novel silicon amphiphilic compounds. Specifically, in one embodiment, there is provided a silicon amphiphilic compound of the formula:

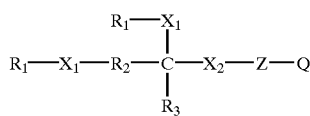

(I)

wherein:
each $X_1$ is independently —O—, —S—, —SO—, —$SO_2$—, —$NR_4$—, —$X_3$—C(=$X_4$)—, —C(=$X_4$)—$X_3$— or —C(=$X_4$)—;

$X_2$ is —$R_5$—$X_3$—$R_6$—, —$R_5$—$X_3$—C(=$X_4$)—$R_6$—, —$R_5$—C(=$X_4$)—$X_3$—$R_6$—, —$R_5$—$X_3$—C(=$X_4$)—$R_6$—C(=$X_4$)—$X_5$—$R_7$—, —$R_5$—$X_3$—(Y$X_3$)P(=$X_4$)—$X_3$—$R_6$—$X_5$—C(=$X_4$)—$R_6$—C(=$X_4$)—$X_3$— or a saccharide diradical;

each $X_3$ is independently a direct bond, —O—, —$NR_4$— or —S—;

each $X_4$ is independently O or S;

each $X_5$ is independently —O—, —$NR_4$— or —S—;

Y is hydrogen or a pharmaceutically acceptable counter ion;

Z is a direct bond or a hydrophilic polymer;

Q is a silicon residue;

each $R_1$ is independently optionally substituted alkyl of 1 to about 50 carbons;

$R_2$ is alkylene of 1 to about 30 carbons;

each of $R_3$ and $R_4$ is independently hydrogen or alkyl of 1 to about 10 carbons; and each of $R_5$, $R_6$ and $R_7$ is independently a direct bond or alkylene of 1 to about 30 carbons.

Silicon amphiphilic compounds which comprise a silicon residue are also the subject of the present invention.

Another aspect of the invention relates to a composition for diagnostic imaging comprising a silicon amphiphilic compound and a gas or gaseous precursor.

Yet another aspect of the invention relates to a cosmetic composition comprising, in combination with a cosmetic agent, a composition which comprises a silicon amphiphilic compound and a gas or gaseous precursor.

Still another aspect of the invention relates to method for the preparation of a composition which comprises a silicon amphiphilic compound and a gas or gaseous precursor. The method comprises agitating, in the presence of a gas or gaseous precursor, an aqueous mixture of a silicon amphiphilic compound.

Another aspect of the invention relates to a method of providing an image of an internal region of a patient. The method comprises administering to the patient a contrast medium which comprises, in an aqueous carrier, a composition comprising a silicon amphiphilic compound and a gas or gaseous precursor. The method also comprises scanning the patient using diagnostic imaging to obtain visible images of the region.

Still another aspect of the invention relates to a method for diagnosing the presence of diseased tissue in a patient. The method comprises administering to the patient a contrast medium which comprises, in an aqueous carrier, a silicon amphiphilic compound and a gas or gaseous precursor. The method also comprises scanning the patient using diagnostic imaging to obtain visible images of any diseased tissue in the patient.

Yet another aspect of the invention relates to a method for the therapeutic delivery in vivo of a bioactive agent. The method comprises administering to a patient a therapeutically effective amount of a formulation which comprises, in combination with a bioactive agent, a composition comprising a silicon amphiphilic compound and a gas or gaseous precursor.

These and other aspects of the invention will become more apparent from the present specification and claims.

DETAILED DESCRIPTION OF THE INVENTION

As employed above and throughout the disclosure, the following terms, unless otherwise indicated, shall be understood to have the following meanings.

"Amphiphile" or "amphiphilic compound" refers to a synthetic or naturally-occurring compound having a water-soluble, hydrophilic portion and a water-insoluble, hydrophobic portion. Preferred amphiphilic compounds are characterized by a polar end group, for example, a phosphatidyicholine, succinate, saccharide or ether group, and one or more nonpolar, aliphatic chains, for example, palmitoyl groups. "Silicon amphiphilic compound" refers to an amphiphilic compound which contains a silicon residue. "Silicon residue", as used herein, refers to a chemical group or moiety which contains at least one silicon atom. An exemplary silicon residue is a siloxy group. "Siloxy group", as used herein, refers to a chemical moiety which consists of at least one silicon atom bonded to at least one oxygen, sulfur or substituted or unsubstituted nitrogen atom. In preferred embodiments, the siloxy group consists of at least one silicon atom bonded to at least one oxygen atom. In certain particularly preferred embodiments, the siloxy group contains at least one moiety of the formula —Si(R)$_2$—O—, where R is, for example, an alkyl group, and preferably, a lower alkyl group. In certain embodiments, the silicon amphiphilic compounds may contain a silicon residue which consists of more than one silicon atom. Thus, the term "silicon residue" encompasses polysiloxane and cyclic polysilane moieties.

In certain preferred embodiments of the present invention, the amphiphilic compounds comprise a lipid compound. "Lipid", as used herein, refers to materials, including fats and fat-derived materials, which are relatively insoluble in water but relatively soluble in organic solvents, such as benzene, chloroform, acetone and ether. Lipids include, for example, fatty acids, fatty acid esters, neutral fats, phosphatides (phospholipids), glycolipids, fatty alcohols, sterols, waxes, terpenes and steroids. Thus, in preferred embodiments, the silicon amphiphilic compounds may comprise a lipid compound which contains a silicon residue.

"Fluorinated silicon amphiphilic compound" refers to a silicon amphiphilic compound in which at least one hydrogen atom present therein is replaced with a fluorine atom. In preferred form, the fluorinated silicon amphiphilic compounds are polyfluorinated. "Polyfluorinated", as used herein, refers to silicon amphiphilic compounds in which at least two hydrogen atoms are replaced with fluorine atoms.

"Stabilized" refers to compositions which have been formulated as a mixture of finely divided colloidal particles floating in a liquid with minimal aggregation. As discussed in detail below, certain preferred embodiments of the present invention involve compositions of stabilized vesicles. In this context, the term "stabilized" refers to vesicles which are substantially resistant to degradation that may be caused, for example, by the loss of structural or compositional integrity in the walls of the vesicles and/or by the loss of any significant portion of a gas, gaseous precursor, bioactive agent, or the like, which is encapsulated within the vesicle.

"Silicon amphiphilic composition" refers to a composition which comprises a silicon amphiphilic compound, typically in an aqueous medium. Exemplary silicon amphiphilic compositions include suspensions, emulsions and vesicle compositions.

"Silicon amphiphilic formulation" refers to a silicon amphiphilic composition which also comprises a bioactive agent.

"Emulsion" refers to a mixture of two or more liquids and is generally in the form of a colloid. The amphiphilic compounds may be heterogeneously dispersed throughout the emulsion. Alternatively, the amphiphilic compounds may be aggregated in the form of, for example, clusters or layers, including mono- or bilayers.

"Suspension" refers to a mixture of finely divided liquid or solid particles floating in a liquid which can remain stable for extended periods of time.

"Hexagonal H II phase structure" refers to a generally tubular aggregation of lipids in liquid media, for example, aqueous media, in which the hydrophilic portion(s) of the amphiphilic compounds generally face inwardly in association with a liquid environment inside the tube. The hydrophobic portion(s) of the amphiphilic compounds generally radiate outwardly and the complex assumes the shape of a hexagonal tube. A plurality of tubes is generally packed together in the hexagonal phase structure.

"Vesicle" or "vesicle species" refer to spherical entities which are generally characterized by the presence of one or more walls or membranes which form one or more internal voids. Vesicles may be formulated, for example, from amphiphilic compounds, including the silicon amphiphilic described herein, conventional lipids, including the various lipids described herein, and/or a combination of the present silicon amphiphilic compounds and conventional lipid compounds. In any given vesicle, the amphiphilic compounds may be in the form of a monolayer or bilayer, and the mono- or bilayer amphiphiles may be used to form one or more mono-or bilayers. In the case of more than one mono- or bilayer, the mono- or bilayers may be concentric. The vesicles may be unilamellar (comprised of one monolayer or bilayer), oligolamellar (comprised of about two or about three monolayers or bilayers) or multilamellar (comprised of more than about three monolayers or bilayers). The vesicles described herein include such entities commonly referred to as, for example, liposomes, micelles, bubbles, microbubbles, microspheres, lipid-coated bubbles, microbubbles and/or microspheres, microcapsules, microballoons, and the like. The internal void of the vesicles may be filled with a liquid (including, for example, an aqueous liquid), a gas, a gaseous precursor, and/or an active agent, including a solid or solute material, such as, for example, a targeting ligand, bioactive agent, cosmetic agent or other active ingredient, as desired.

"Liposome" refers to a generally spherical cluster or aggregate of amphiphilic compounds, typically in the form of one or more concentric layers, for example, bilayers. The liposomes may be formulated, for example, from the silicon amphiphilic described herein, conventional amphiphilic compounds, including lipids, such as ionic and/or non-ionic lipids, and/or a combination of the present silicon amphiphilic compounds and conventional amphiphilic compounds. Liposomes which are formulated from non-ionic lipids may also be referred to as "niosomes."

"Micelle" refers to colloidal entities formulated from amphiphilic compounds, including the silicon amphiphilic compounds described herein, as well as conventional lipids. In certain preferred embodiments, the micelles comprise a monolayer or hexagonal H2 phase configuration. In other preferred embodiments, the micelles may comprise a bilayer configuration.

The vesicles of the present invention preferably contain a gas or gaseous precursor. "Gas filled vesicle" refers to vesicles in which there is encapsulated a gas. "Gaseous precursor filled vesicle" refers to vesicles in which there is encapsulated a gaseous precursor. The vesicles may be minimally, partially or substantially completely filled with the gas and/or gaseous precursor. In certain preferred embodiments, the vesicles may be substantially or completely filled with the gas and/or gaseous precursor. The term "substantially", as used in reference to the gas and/or gaseous precursor filled vesicles, means that greater than about 50% of the internal void volume of the vesicle consists of a gas. Preferably, greater than about 60% of the internal void of the substantially filled vesicles consists of a gas, with greater than about 70% being more preferred. Even more preferably, greater than about 80% of the internal void of the substantially filled vesicles consists of a gas, with greater than about 90% being still more preferred. In particularly preferred embodiments, greater than about 95% of the internal void of the vesicles consists of a gas, with about 100% being especially preferred. Although not considered a preferred embodiment of the present invention, the vesicles may also contain, if desired, no or substantially no gas or gaseous precursor.

"Vesicle composition" refers to a composition, typically in an aqueous medium, which comprises vesicles.

"Vesicle formulation" refers to a vesicle composition which also comprises a bioactive agent. Suitable vesicles or vesicle species for use in vesicle formulations include, for example, gas filled vesicles and gaseous precursor filled vesicles.

"Patient" refers to animals, including mammals, preferably humans.

The phrases "internal region of a patient" and "region of interest" refer to the entire patient or to a particular area or portion of the patient. Internal regions of a patient and regions of interest may include, for example, areas being imaged with diagnostic imaging and/or areas being treated with a bioactive agent. Exemplary of such areas include, for example, the heart region, including myocardial tissue, as well as other bodily tissues, including the vasculature and circulatory system and cancerous tissue. The phrase "vasculature," as used herein, denotes the blood vessels in the body or in an organ or part of the body.

"Bioactive agent" refers to a substance which may be used in connection with an application that is therapeutic or diagnostic in nature, such as in methods for diagnosing the presence or absence of a disease in a patient and/or in methods for the treatment of disease in a patient. As used herein, "bioactive agent" refers also to substances which are capable of exerting a biological effect in vitro and/or in vivo. The bioactive agents may be neutral or positively or negatively charged. Examples of suitable bioactive agents include diagnostic agents, pharmaceuticals, drugs, synthetic organic molecules, proteins, peptides, vitamins, steroids and genetic material, including nucleosides, nucleotides and polynucleotides.

"Diagnostic agent" refers to any agent which may be used in connection with methods for imaging an internal region of a patient and/or diagnosing the presence or absence of a disease in a patient. Exemplary diagnostic agents include, for example, contrast agents for use in connection with ultrasound, magnetic resonance imaging or computed tomography of a patient including, for example, the amphiphilic compositions described herein.

"Polymer", as used herein, refers to molecules formed from the chemical union of two or more repeating units. Accordingly, included within the term "polymer" may be, for example, dimers, trimers and oligomers. The polymer may be synthetic, naturally-occurring or semisynthetic. In preferred form, the term "polymer" refers to molecules which comprise 10 or more repeating units.

"Thickening agent" refers to any of a variety of generally hydrophilic materials which, when incorporated in the amphiphilic compositions described herein, may act as viscosity modifying agents, emulsifying and/or solubilizing agents, suspending agents, and tonicity raising agents. It is contemplated that the thickening agents may be capable of aiding in maintaining the stability of the compositions due to such properties.

"Dispersing agent" refers to a surface-active agent which, when added to a suspending medium of colloidal particles, including, for example, certain of the amphiphilic compositions described herein, may promote uniform separation of particles.

"Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination of the two. The DNA and RNA may optionally comprise unnatural nucleotides and may be single or double stranded. "Genetic material" refers also to sense and anti-sense DNA and RNA, that is, a nucleotide sequence which is complementary to a specific sequence of nucleotides in DNA and/or RNA.

"Pharmaceutical" or "drug" refers to any therapeutic or prophylactic agent which may be used in the treatment (including the prevention, diagnosis, alleviation, or cure) of a malady, affliction, disease or injury in a patient. Therapeutically useful peptides, polypeptides and polynucleotides may be included within the meaning of the term pharmaceutical or drug.

"Stabilizing material" refers to a substance which is biocompatible and which is capable of promoting the formation of vesicles in a silicon amphiphilic composition. As used herein, "stabilizing material" refers also to a substance which is biocompatible and which is capable of improving the stability of a vesicle. The stabilizing materials may comprise amphipathic compounds, including lipids, such as conventional phospholipids, surfactants and fatty materials, as well as polymeric materials. Encompassed also in the definition of "stabilizing material" are certain of the present bioactive agents. The stabilizing material may be neutral or positively or negatively charged. Preferred among the neutral stabilizing materials are polar materials.

"Vesicle stability" refers to the ability of gas-filled vesicles to retain the gas entrapped therein after being exposed, for about one minute, to a pressure of about 300 mm Hg. Vesicle stability may be measured in percent (%), which corresponds to the fraction of the amount of gas which is originally entrapped in the vesicle and which is retained after release of the pressure. Vesicle stability includes reference also to "vesicle resilience" which refers to the ability of a vesicle to return to its original size after release of the pressure.

"Biocompatible" refers to materials which are generally not injurious to biological functions and which will not result in any degree of unacceptable toxicity, including allergenic responses and disease states.

"In combination with" refers, in certain embodiments, to the incorporation of a bioactive agent in a composition of the present invention. "In combination with" may also refer to the incorporation of a targeting ligand in a composition of the present invention. In addition, "in combination with" may refer to the incorporation of additional materials, such as stabilizing materials and excipients, in a composition of the present invention. The bioactive agent, targeting ligand and/or additional materials may be combined with the present compositions in any of a variety of ways. For example, in the case of silicon amphiphilic compositions, the bioactive agent, targeting ligand and/or additional materials may be associated covalently and/or non-covalently with the amphiphilic compounds. The bioactive agent and/or targeting ligand may also be associated covalently and/or non-covalently with optional stabilizing materials. In the case of vesicle compositions, the bioactive agent, targeting ligand and/or additional materials may be entrapped within the internal void of the vesicle. The bioactive agent, targeting ligand and/or additional materials may also be integrated within the layer(s) or wall(s) of the vesicle, for example, by being interspersed among amphiphilic compounds which are contained within the vesicle layer(s) or wall(s). In addition, it is contemplated that the bioactive agent, targeting ligand and/or additional materials may be located on the surface of a vesicle. In any case, the bioactive agent, targeting ligand and/or additional materials may interact chemically with the walls of the vesicles, including, for example, the inner and/or outer surfaces of the vesicle and may remain substantially adhered thereto. Such interaction may take the form of, for example, covalent association or non-covalent association. In certain embodiments, the interaction may result in the stabilization of the vesicle.

"Targeting ligand" refers to any material or substance which may promote targeting of tissues and/or receptors in vivo with the compositions described herein. The targeting ligand may be synthetic, semi-synthetic, or naturally-occurring. Materials or substances which may serve as targeting ligands include, for example, proteins, including antibodies, glycoproteins and lectins, peptides, polypeptides, saccharides, including mono- and polysaccharides, vitamins, steroids, steroid analogs, hormones, cofactors, bioactive agents, and genetic material, including nucleosides, nucleotides and polynucleotides.

"Van der Waal's radius" refers generally to the size of an atom. The van der Waal's radius is about equal to the distance between the nuclei of two nonbonded atoms at a point where attractive forces due, for example, to electrostatic interactions, are about equal to repulsive forces due, for example, to overlap of the outer portions of electron clouds of the atoms.

"Aliphatic" refers to one of the major groups of organic compounds, characterized by straight- or branched-chain arrangement of the constituent carbon atoms. Aliphatic hydrocarbons comprise three subgroups: (1) paraffins, including the alkanes; (2) olefins, including the alkenes, which contain carbon-carbon double bonds; and (3) acetylenes, including the alkynes, which contain carbon-carbon triple bonds.

"Alkyl" refers to an aliphatic hydrocarbon group which may be straight or branched having 1 to about 30 carbon atoms. "Lower alkyl" refers to an alkyl group having 1 to about 8 carbon atoms, preferably, about 1 to about 4 carbon atoms. "Higher alkyl" refers to an alkyl group having about 10 to about 30 carbon atoms. The allyl group may be optionally substituted with one or more alkyl group substituents which may be the same or different, where "alkyl group substituent" includes, for example, halo, aryl, hydroxy, alkoxy, aryloxy, alkyloky, alkylthio, arylthio, carboxy alkoxycarbonyl, oxo and cycloalkyl. There may be optionally inserted along the alkyl group one or more oxygen, sulphur or substituted nitrogen atoms, wherein the nitrogen substituent is preferably lower alkyl. The alkyl group may be linear or branched. "Branched" refers to an alkyl group in which an alkyl group, preferably a lower alkyl group, such as methyl, ethyl or propyl, is attached to a linear alkyl chain. The alkyl group can include one or more points of unsaturation including, for example, carbon-carbon double bonds and carbon-carbon triple bonds. Exemplary alkyl groups include, for example, methyl, ethyl, i-propyl, n-butyl, s-butyl, t-butyl, n-pentyl, heptyl, octyl, nonyl, decyl, undecyl, dodecyl, tridecyl, tetradecyl, pentadecyl and hexadecyl. Preferred alkyl groups include the lower alkyl groups having 1 to about 4 carbon atoms and the higher alkyl groups having about 10 to about 16 carbon atoms. Exemplary alkyl groups which contain alkyl group substituents include hydroxylated alkyl groups, such as alkyl groups derived from glycerol, including, for example, 2,3-dihydroxyprop-1-yl.

"Alkylene" refers to a bivalent aliphatic hydrocarbon group having from 1 to about 30 carbon atoms. The alkylene group may be straight, branched or cyclic. The alkylene group may be also optionally unsaturated and/or substituted with one or more "alkyl group substituents." There may be optionally inserted along the alkylene group one or more oxygen, sulphur or substituted or unsubstituted nitrogen atoms, wherein the nitrogen substituent is alkyl as previously described. Exemplary alkylene groups include methylene (—$CH_2$—), ethylene (—$CH_2CH_2$—), propylene (—$(CH_2)_3$—), prop-1,2,3-triyl (—$CH_2$—CH(-)—$CH_2$—), cyclohexylene (—$C_6H_{10}$—), —CH=CH—CH=CH—, —CH=CH—$CH_2$—, —$(CF_2)_n(CH_2)_m$—, wherein n is an integer from about 1 to about 22 and m is an integer from 0 to about 22, —$(CH_2)_n$—N(R)—$(CH_2)_m$—, wherein each of m and n is independently an integer from 0 to about 30 and R is hydrogen or alkyl, methylenedioxy (—O—$CH_2$—O—) and ethylenedioxy (—O—$(CH_2)_2$—O—). It is preferred that the alkylene group has about 2 to about 3 carbon atoms.

"Alkenyl" refers to an alkyl group which contains one or more carbon-carbon double bonds. "Lower alkenyl" refers to alkenyl having 2 to about 8 carbons. "Higher alkenyl" refers to alkenyl having about 10 to about 30 carbons. The alkenyl may be optionally substituted with one or more "alkyl group substituents." Exemplary alkenyl groups include vinyl, allyl, n-pentenyl, decenyl, dodecenyl and tetradecadienyl. Preferred alkenyl groups include the lower alkenyl groups.

"Alkynyl" refers to an alkyl group which contains one or more carbon-carbon triple bonds. "Lower alkynyl" refers to alkynyl having 2 to about 8 carbons. "Higher alkenyl" refers to alkynyl having about 10 to about 30 carbons. The alkynyl may be optionally substituted with one or more "alkyl group substituents." Exemplary alkynyl groups include ethynyl, propargyl, n-pentynyl, decynyl and dodecynyl. Preferred alkynyl groups include the lower alkynyl groups.

"Cycloalkyl" refers to a non-aromatic mono- or multicyclic ring system of about 4 to about 10 carbon atoms. The cycloalkyl group may be optionally partially unsaturated. The cycloalkyl group may be also optionally substituted with an alkyl group substituent, oxo and/or alkylene. Preferred monocyclic cycloalkyl rings include cyclopentyl, cyclohexyl and cycloheptyl. Preferred multicyclic cycloalkyl rings include adamantyl, octahydronaphthyl, decalin, camphor, camphane, noradamantyl, bicyclo[2.2.2.] oct-5-ene, cis-5-norbornene, 5-norbornene, (1R)-(–)-myrtentane, norbornane and anti-3-oxo-tricyclo[2.2.1.0$^{2.6}$] heptane.

"Heterocyclyl" refers to a monocyclic or multicyclic ring system of about 4 to about 10 members wherein one or more of the atoms in the ring system is an element other than carbon including, for example, nitrogen, oxygen or sulfur. The heterocyclyl group may be optionally partially unsaturated. The heterocyclyl group may be also optionally substituted with an alkyl group substituent, oxo and/or alkylene. Preferred monocyclic cycloalkyl rings include furyl, pyrrolidinyl, piperidinyl, morpholinyl, tetrahydroquinolinyl and tetrahydroisoquinolinyl.

"Aryl" refers to an aromatic carbocyclic radical containing from about 6 to about 10 carbon atoms. The aryl group may be optionally substituted with one or more aryl group substituents which may be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and -NRR', where R and R' are each independently hydrogen, alkyl, aryl and aralkyl. Exemplary aryl groups include substituted or unsubstituted phenyl and substituted or unsubstituted naphthyl.

"Heteroaryl" refers to a monocyclic or multicyclic ring system of about 5 to about 10 members wherein one or more of the atoms in the ring is an element other than carbo including, for example, nitrogen, oxygen and sulfur. The heteroaryl group may be optionally substituted with one or more aryl group substituents. Exemplary heteroaryl groups include furanyl, thienyl, pyridyl, pyrrolyl, N-methylpyrrolyl, quinolinyl and isoquinolinyl.

The present invention is directed, in part, to a new class of silicon amphiphilic compounds which are highly useful in connection with methods for diagnostic imaging. Specifically, the present invention relates to silicon amphiphilic compounds of the formula:

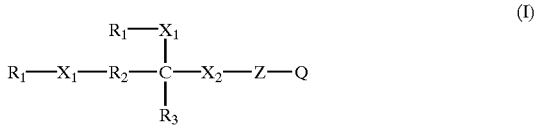

(I)

wherein:

each $X_1$ is independently —O—, —S—, —SO—, —SO$_2$—, —NR$_4$—, —X$_3$—C(=X$_4$)—, —C(=X$_4$)—X$_3$— or —C(=X$_4$)—;

$X_2$ is —R$_5$—X$_3$—R$_6$—, —R$_5$—X$_3$—C(=X$_4$)—R$_6$—, —R$_5$—C(=X$_4$)—X$_3$—R$_6$—, —R$_5$—X$_3$—C(=X$_4$)—R$_6$—C(=X$_4$)—X$_5$—R$_7$—,
—R$_5$—X$_3$—(YX$_3$)P(=X$_4$)—X$_3$—R$_6$—X$_5$—C(=X$_4$)—R$_6$—C(=X$_4$)—X$_3$— or a saccharide diradical;

each $X_3$ is independently a direct bond, —O—, —NR$_4$— or —S—;

each $X_4$ is independently O or S;

each $X_5$ is independently —O—, —NR$_4$— or —S—;

Y is hydrogen or a pharmaceutically acceptable counter ion;

Z is a direct bond or a hydrophilic polymer;

Q is a silicon residue;

each $R_1$ is independently optionally substituted alkyl of 1 to about 50 carbons;

$R_2$ is alkylene of 1 to about 30 carbons;

each of $R_3$ and $R_4$ is independently hydrogen or alkyl of 1 to about 10 carbons; and each of $R_5$, $R_6$ and $R_7$ is independently a direct bond or alkylene of 1 to about 30 carbons.

In the above formula (I), each $X_1$ is independently —O—, —S—, —SO—, —SO$_2$—, —NR$_4$—, —X$_3$—C(=X$_4$)—, —C(=X$_4$)—X$_3$— or —C(=X$_4$)—. Preferably, each $X_1$ is independently —O—, —NR$_4$—, —X$_3$—C(=X$_4$)—, —C(=X$_4$)—X$_3$— or —C(=X$_4$)—. More preferably, each $X_1$ is independently —O—, —X$_3$—C(=X$_4$)— or —C(=X$_4$)—X$_3$—. Even more preferably, $X_1$ is —C(=X$_4$)—X$_3$—.

$X_2$ in the above formula (1) is —R$_5$—X$_3$—R$_6$—, —R$_5$—X$_3$—C(=X$_4$)—R$_6$—, —R$_5$—C(=X$_4$)—X$_3$—R$_6$—, —R$_5$—X$_3$—C(=X$_4$)—R$_6$—C(=X$_4$)—X$_5$—R$_7$—,
—R$_5$—X$_3$—(YX$_3$)P(=X$_4$)—X$_3$—R$_6$—X$_5$—C(=X$_4$)—R$_6$—C(=X$_4$)—X$_3$— or a saccharide diradical.
Preferably, $X_2$ is —R$_5$—X$_3$—R$_6$—, —R$_5$—X$_3$—C(=X$_4$)—R$_6$—C(=X$_4$)—X$_5$—R$_7$— or —R$_5$—X$_3$—(YX$_3$)P(=X$_4$)—X$_3$—R$_6$—X$_3$—C(=X$_4$)—R$_6$—C(=X$_4$)—X$_3$—.

In the above formula (I), each $X_3$ is independently a direct bond, —O—, —NR$_4$— or —S—. Preferably, $X_3$ is —O—.

Each $X_4$ in the above formula (I) is independently O or S. Preferably, $X_4$ is O.

In the above formula (I), each $X_5$ is independently —O—, —NR$_4$— or —S—. Preferably, $X_5$ is —O— or —NR$_4$—.

Y in the above formula (I) is hydrogen or a pharmaceutically acceptable counter ion. Exemplary pharmaceutically acceptable counter ions include, for example, sodium, potassium, and ammonium ions.

In the above formula (I), Z is a direct bond or a hydrophilic polymer, and Q is a silicon residue.

Each $R_1$ in the above formula (I) is independently optionally substituted alkyl of 1 to about 50 carbons. In certain preferred embodiments, $R_1$ is unsubstituted alkyl of 1 to about 50 carbons, while in certain other preferred embodiments, $R_1$ is substituted alkyl of 1 to about 50 carbons. Preferably, each $R_1$ is independently optionally substituted alkyl of 1 to about 30 carbons. More preferably, each $R_1$ is independently optionally substituted alkyl of 1 to about 20 carbons. Even more preferably, each $R_1$ is independently optionally substituted alkyl of 1 to about 15 carbons.

In the above formula (1), $R_2$ is alkylene of 1 to about 30 carbons. Preferably, $R_2$ is allylene of 1 to about 15 carbons, with alkylene of 1 to about 10 carbons being more preferred. Even more preferably, $R_2$ is alkylene of 1 to about 5 carbons. Still more preferably, $R_2$ is methylene (—CH$_2$—).

Each of $R_3$ and $R_4$ in the above formula (I) is independently hydrogen or alkyl of 1 to about 10 carbons. Preferably, each of $R_3$ and $R_4$ is independently hydrogen or alkyl of 1 to about 4 carbons. More preferably, $R_3$ and $R_4$ are hydrogen.

In the above formula (I), each of $R_5$, $R_6$ and $R_7$ is independently a direct bond or alkylene of 1 to about 30 carbons. Preferably, each of $R_5$, $R_6$ and $R_7$ is independently a direct bond or alkylene of 1 to about 15 carbons. More preferably, each of $R_5$, $R_6$ and $R_7$ is a direct bond or alkylene of 1 to about 10 carbons. Even more preferably, each of $R_5$, $R_6$ and $R_7$ is a direct bond or alkylene of 1 to about 5 carbons. Still more preferably, $R_5$ is methylene, $R_6$ is a direct bond or ethylene, and $R_7$ is a direct bond or propylene.

In the formulas depicted herein, it is intended that when any symbol appears more than once in a formula and/or substituent, its meaning in each instance is independent of the other. Also in the formulas depicted herein, it is intended that when two or more adjacent symbols are defined as being a "direct bond" to provide multiple, adjacent direct bonds, the multiple and adjacent direct bonds devolve into a single direct bond.

As noted above, Z in the definition of formula (I), can be a hydrophilic polymer. Exemplary polymers from which Z can be derived include polymers in which the repeating units contain one or more hydroxy groups (polyhydroxy polymers), including, for example, polyvinyl alcohol; polymers in which the repeating units contain one or more ether linkages, including for example, polyethylene glycol, which comprises repeating units of —(CH$_2$CH$_2$O)—; polymers in which the repeating units contain one or more amide groups, including for example, polyvinylpyrrolidone; polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates. The molecular weight of the polymers from which Z is derived may vary, and generally may range from about 50 to about 5,000,000, and all combinations and subcombinations of ranges therein. Preferably, the polymers defined by Z have a molecular weight of from about 100 to about 50,000, with polymers have a molecular weight of from about 150 to about 10,000 being more preferred, and polymers having a molecular weights of from about 200 to about 8,000 being even more preferred.

Preferred polymers from which Z is derived include, for example, polyethyleneglycol (PEG), polyvinylpyrrolidine, polyoxomers, polysorbate and polyvinyl alcohol, with PEG polymers being particularly preferred. Preferred among the PEG polymers are PEG polymers having a molecular weight which ranges from about 100 to about 10,000, and all combinations and subcombinations of ranges therein. More preferably, the PEG polymers have a molecular weight of from about 200 to about 8,000, with PEG1000, PEG5000 and PEG8000 polymers, which are PEG polymers having molecular weights of about 1,000, about 5,000 and about 8,000, respectively, being even more preferred.

Other suitable hydrophilic polymers, in addition to those exemplified above, will be readily apparent to one skilled in the. art based on the present disclosure. Generally, polymers from which Z may be derived include polymers that can be incorporated in the silicon amphiphilic compounds via alkylation or acylation reactions. Such polymers and alkylation or acylation reactions would be readily apparent to one of ordinary skill in the art, once armed with the present disclosure.

As indicated above, Z may also be a saccharide diradical. The saccharide diradical may be a monosaccharide, disaccharide, oligosaccharide or polysaccharide diradical, and derivatives thereof. Suitable saccharides which are represented by Z include arabinans, fructans, fucans, galactans, galacturonans, glucans, mannans, xylans (such as, for example, inulin), levan, fucoidan, carrageenan, galactocarolose, pectic acid, amylose, pullulan, glycogen, amylopectin, cellulose, dextran, pustulan, chitin, agarose, keratin, chondroitan, dermatan, hyaluronic acid, alginic acid, xanthan gum, starch and various other materials, including natural homopolymer or heteropolymers, which contain one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof.

As with the various specific polymers exemplified above, it is contemplated that the polymers and/or saccharides encompassed by Z may contain functional groups in addition, for example, to those which may be involved in linking the polymers and/or saccharides to the silicon amphiphilic compounds. Such functionalities include, for example, carboxyl, amine, hydroxy and thiol groups. These functional groups on the polymeric or saccharide residues can be further reacted, if desired, with materials which are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins and nucleosides. Also, as discussed in detail below, the additional functional groups may be reacted, if desired, with a material that comprises a silicon residue.

As noted above, Q in the above formula (I) is a silicon residue. In preferred embodiments, Q is a residue of the formula —$X_6$—[Si($R_8$)$_2$—$X_3$—Z]$_n$—Si($R_8$)$_3$ wherein:

n is an integer from 0 to about 10,000;

$X_3$ is as previously defined;

$X_6$ is a direct bond, —O—, —$NR_5$— or —S—;

Z is as previously defined; and each $R_8$ is independently alkyl, alkenyl, alkynyl, aryl, heteroaryl, cycloalkyl or heterocyclyl.

In the above definition of Q, n is an integer from 0 to about 10,000. Preferably, n is an integer from 0 to about 1,000, with integers of from 0 to about 100 being more preferred. Even mare preferably, n is an integer from 0 to about 10. In certain preferred embodiments, n is 0. In other preferred embodiments, n is an integer from 1 to about 8, and more preferably, from about 3 to about 6.

In the above definition of Q, $X_6$ is a direct bond, —O—, —$NR_5$— or —S—. Preferably, $X_6$ is a direct bond or —O—.

Also in the above definition of Q, each $R_8$ is independently alkyl, alkenyl, alkynyl, aryl, heteroaryl, cycloalkyl or heterocyclyl. Preferably, each $R_8$ is alkyl, aryl or cycloalkyl, with alkyl being preferred. Preferred among the alkyl defined by $R^8$ are alkyl of 1 to about 10 carbons, with alkyl of 1 to about 4 carbons being more preferred. Even more preferably, $R_8$ is methyl (—$CH_3$).

As noted above, each $R_1$ in the above formula (I) is independently optionally substituted alkyl of 1 to about 50 carbons, with optionally substituted alkyl of 1 to about 30 carbons being preferred. Preferred substituents include the "alkyl substituents" described above. In certain particularly preferred embodiments, at least one of $R_1$ is substituted with at least one halogen atom, that is, a fluorine, chlorine, bromine or iodine atom, with fluorine atoms being preferred. Accordingly, in connection with certain preferred embodiments of the present invention, at least one of $R_1$ is fluorinated alkyl of 1 to about 30 carbons, and the other of $R_1$ is optionally substituted alkyl of 1 to about 30 carbons, for example, unsubstituted alkyl of 1 to about 30 carbons. In these embodiments, the fluorinated $R_1$ group is preferably polyfluorinated alkyl of 1 to about 30 carbons, with perfluorinated alkyl of 1 to about 30 carbons being more preferred. In embodiments in which at least one of $R_1$. is fluorinated alkyl of 1 to about 30 carbons, both of $R_1$ may be fluorinated alkyl of 1 to about 30 carbons, preferably polyfluorinated alkyl of 1 to about 30 carbons, more preferably perfluorinated alkyl of 1 to about 30 carbons.

In embodiments in which at least one of $R_1$ is perfluorinated alkyl of 1 to about 30 carbons, at least one of $R_1$I, and preferably both of R, may be $CaF_{2a+1}—(CH_2)_b—$, wherein a is an integer which ranges from 1 to about 30, and all combinations and subcombinations of ranges therein, and b is an integer which ranges from 0 to about 29, and all combinations and subcombinations of ranges therein, wherein the sum of a and b is not greater than 30. Preferably, a is an integer from 1 to about 10, and b is an integer from 1 to about 20. More preferably, a is an integer from about 3 to about 8, and b is an integer from about 5 to about 15. Still more preferably, a is an integer from about 4 to about 6, and b is an integer from about 9 to about 13. Even more preferably, a is about 5 and b is about 11.

The novel silicon amphiphilic compounds of the present invention, as exemplified by the compounds of formula (I), contain a silicon residue which consists of at least one silicon atom and preferably, at least one siloxy group. The presence of at least one silicon atom and/or siloxy groups and, in certain embodiments, two or more silicon atoms and/or siloxy groups, imparts highly desirable and beneficial properties to the novel amphiphilic compounds. Such properties are generally absent from amphiphilic compounds known heretofore. In this connection, the silicon amphiphilic compounds described herein may be employed in contrast agents for use, for example, in diagnostic imaging, including, for example, ultrasound, computed tomography, and magnetic resonance imaging. Exemplary of such compositions are amphiphilic compositions, and especially, vesicle compositions, such as compositions which comprise micelles and/or liposomes. It has been surprisingly and unexpectedly found that the silicon amphiphilic compounds of the present invention are capable of stabilizing these compositions, including the preferred compositions which comprise vesicles. It has been found also that the present silicon amphiphilic compounds are capable of promoting the formation of vesicles, as well as improving the stability of the formed vesicles. In embodiments in which the vesicles comprise gas filled and/or gaseous precursor filled vesicles, the silicon amphiphilic compounds enable the vesicles to substantially retain the gas and/or gaseous precursor with minimal loss or leakage. This is surprising and. unexpected and generally renders unnecessary the use of additional stabilizing materials, including, for example, surfactants, and stabilizing techniques, including, for example, crosslinking of the materials included in the walls of the vesicles. As discussed above, such techniques have generally been necessary in connection with contrast agents of the prior art. Moreover, the present silicon amphiphilic compounds are generally biocompatible and can be obtained with minimal effort and at minimal expense. Accordingly, the present invention is directed to simple and efficient methods for providing stabilized compositions, including stabilized vesicle compositions, for use as contrast agents in diagnostic imaging, especially ultrasound.

While the inventors do not wish to be bound by any theory or theories of operation, it is believed that the improved ability of the silicon amphiphilic compounds of the present invention to stabilize and/or assist in the formation of amphiphilic compositions, especially vesicle compositions, is due, at least in part, to the presence of the silicon atom(s) and/or siloxy group(s). In this connection, the silicon amphiphilic compounds of the present invention are preferably amphipathic, since they contain both a hydrophilic portion, for example, a siloxy group, and a hydrophobic portion, for example, an alkyl group. It is contemplated that the amphipathic properties of the present silicon amphiphilic compounds may promote the stabilization of amphiphilic compositions, as well as the formation of vesicles in such compositions.

Moreover, the silicon amphiphilic compounds of the present invention are believed to possess unique properties in connection with their behavior as surfactants. These unique properties may further improve the stability of the present amphiphilic compositions, especially vesicle compositions. The silicon residue, as exemplified by the substituent Q in the compounds of formula (I), is generally bulky and possesses an increased van der Waal's radius relative to other chemical groups and/or substituents, including chemical groups and substituents contained in prior art amphiphilic compounds. It is believed that this increased van der Waal's radius may promote stabilization of multi-molecular and/or supramolecular aggregates of these compounds. Exemplary of such aggregates include, for example, vesicles. It is noted also that the silicon amphiphilic compounds of the present invention contain both organic moieties, such as, for example, lipid moieties, and inorganic (silicon-containing) moieties. It is contemplated that the desirable stabilizing properties afforded by the present silicon amphiphilic compounds may be due to this unique combination of organic and inorganic moieties.

As noted above, the silicon amphiphilic compounds of the present invention comprise at least one silicon atom. In an alternate embodiment, the silicon amphiphilic compounds may comprise more than one silicon atom, for example, at least two silicon atoms. In another alternate embodiment, the silicon amphiphilic compounds may comprise more than two silicon atoms, for example, at least three silicon atoms. In yet another alternate embodiment, the silicon amphiphilic compounds may comprise more than three silicon atoms, for example, at least four silicon atoms. In still another alternate embodiment, the silicon amphiphilic compounds may comprise more than four silicon atoms, for example, at least five silicon atoms. In yet another alternate embodiment, the silicon amphiphilic compounds may comprise more than five silicon atoms, for example, at least six silicon atoms. In still another alternate embodiment, the silicon amphiphilic compounds may comprise more than six silicon atoms, for example, at least seven silicon atoms. In certain embodiments, the silicon amphiphilic compounds may comprise more than seven silicon atoms.

As noted above in connection with a preferred embodiment of the invention, the silicon residue in the present silicon amphiphilic compounds may comprise a siloxy group. In these preferred embodiments, the silicon residue may, alternatively, comprise more than one siloxy group, for example, at least two siloxy groups. In another alternate embodiment, the silicon residue may comprise more than two siloxy groups, for example, at least three siloxy groups. In yet another alternate embodiment, the silicon residue may comprise more than three siloxy groups, for example, at least four siloxy groups. In still another alternate embodiment, the silicon residue may comprise more than four siloxy groups, for example, at least five siloxy groups. In yet another alternate embodiment, the silicon residue may comprise more than five siloxy groups, for example, at least six siloxy groups. In still another alternate embodiment, the silicon residue may comprise more than six siloxy groups.

The silicon amphiphilic compounds of the present invention, including the silicon amphiphilic compounds of formula (I), can be prepared readily using standard synthetic methodology well known to those of ordinary skill in the art. In this connection, various compounds which may serve as starting materials for the preparation of the silicon amphiphilic compounds of the present invention are commercially available, or may likewise be readily synthesized. For example, glycerols, including substituted glycerols, glycerol succinates and substituted glycerol succinates, are commercially available from various sources, including, for example, Avanti Polar Lipids (Alabaster Ala.). These materials may be silylated to provide the silicon amphiphilic compounds of the present invention. The silylation reaction may involve standard silylating agents which are also commercially available, including, for example, hexamethyldisilazane, which is commercially available from the Aldrich Chemical Co. (Milwaukee, Wis.). Alternatively, the aforementioned glycerol compounds may be combined, under appropriate reaction conditions, with reactive silicone compounds, for example, silicone compounds which contain reactive groups, such as amine-terminated siloxanes, to provide the silicon amphiphilic compounds of the present invention. Such reactive siloxanes are also commercially available from various sources, including, for example, United Chemical Technologies, Inc. (Bristol, Pa.). The glycerol and reactive siloxane can be reacted together, depending on the particular functional and/or reactive groups present in the respective materials, using standard nucleophilic substitution chemistry and/or standard peptide coupling methodology. For example, the aforementioned glycerols and amine-terminated siloxanes may be combined, preferably in a polar aprotic solvent, such as chloroform or methylene chloride, and reacted at temperatures of from about −10° C. to about the reflux temperature of the solvent. Preferably, the materials are reacted at a temperature of from about 0° C. to about 50° C. If desired, coupling reagents, such as dicyclohexylcarbodiimide, may be used to promote the coupling reaction, particularly in connection with reactions which involve the formation of amide bonds.

As would be apparent to one of ordinary skill in the art, once armed with the present disclosure, the glycerol-containing starting materials described above may include an alkenyl moiety and/or an alkynyl moiety. In these embodiments, the residue Q may be incorporated into the compounds of formula (I) via a hydrosilylation addition reaction involving, for example, the aforementioned unsaturated glycerol compound starting materials and a diorganosiloxane compound of the formula

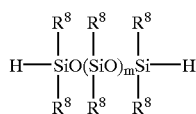

(II)

wherein $R^8$ is as previously defined; and m is an integer of 0 or greater.

It should be understood that the diorganosiloxane moiety (II), when incorporated in the compounds of formula (1), may comprise a mixture of diorganosiloxanes having several values for m. Thus, formula (II) may be a 1,1,3,3-tetraorganodisiloxane when it comprises only diorganosiloxane where m is equal to 0. While the upper limit on m is not specifically restricted, m is preferably an integer of from 0 to about 10,000, more preferably 0 to about 1,000, even more preferably 0 to about 100, still more preferably 0 to about 10.

Compounds of formula (II) are specifically exemplified by the following diorganosiloxanes and by mixtures obtained therefrom.

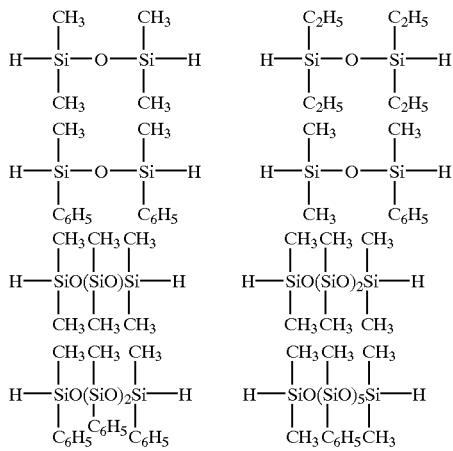

The hydrosilylation reaction is preferably conducted in the presence of a hydrosilylation catalyst which may, serve to accelerate the reaction between the silicon-bonded hydrogen atoms in the compounds of formula (II) and the unsaturated carbon-carbon bonds in the alkenyl/alkynyl moiety-containing starting materials. A wide variety of catalysts are available which may be utilized in the hydrosilylation reaction. Included among such catalysts are platinum catalysts, rhodium catalysts, palladium catalysts, and organoperoxides. Platinum catalysts are preferred in that they may provide a substantial acceleration of the addition reaction. Preferred platinum catalysts include, for example, platinum black, platinum supported on silica micropowder, platinum supported on carbon powder, chloroplatinic acid, alcohol solutions of chloroplatinic acid, platinum vinylsiloxane complexes, and platinum-olefin complexes. The quantity of the catalyst utilized in the addition reaction may vary, depending on the particular organodisiloxane, alkenyl/alkynyl starting material, catalyst and the like utilized. Generally speaking, the catalyst may be utilized in an amount of from about 0.1 to about 500 weight parts (as Pt metal) per 1,000,000 parts by weight based on the total weight of the starting materials.

The sequence of addition of the compounds of formula (II) and the other starting materials in the preparative methods described herein may vary. For example, the alkenyl/alkynyl moiety-containing starting material may be gradually added to a stirred and heated mixture of the compound of formula (II) and the catalyst. Alternatively, the compound of formula (II) may be gradually added to a stirred and heated mixture of the alkenyl/alkynyl moiety-containing starting material and the catalyst. In yet another embodiment, the catalyst may be gradually added to a stirred and heated mixture of the compound of formula (II) and the alkenyl/alkynyl moiety-containing starting material. In still another embodiment, the various starting materials and the catalyst may be combined, stirred and heated.

The hydrosilylation reaction may be conducted neat or in the presence of an organic solvent. Generally speaking, the use of an organic solvent enables the synthesis of organo-silicon compounds with higher molecular weights by the preparative methods described herein. Organic solvents usable in the hydrosilylation reaction include, for example, aromatic hydrocarbon solvents, such as toluene and xylene; aliphatic hydrocarbon solvents, such as hexane, heptane, octane, and nonane; alicyclic hydrocarbon solvents, such as cyclohexane, cycloheptane and cyclooctane; and fluorine-containing aromatic hydrocarbon solvents, such as trifluoromethylbenzene, 1,3-bis(trifluoromethyl)benzene and methylpentafluorobenzene The reaction conditions utilized in the hydrosilylation reaction may vary and depends, for example, on the particular reactants and catalysts involved. When the addition reaction is conducted at ambient pressures, the reaction temperature may range from about room temperature to the boiling point of the compound of formula (II) or the alkenyl/alkynyl moiety-containing starting material, or the boiling point of any organic solvent used. The addition reaction may also be conducted under increased pressures when the boiling points of the starting materials and the (optional) organic solvent are relatively low.

Methods which may be utilized in the preparation of the silicon amphiphilic compounds of the present invention are further described, for example, in U.S. Pat. No. 5,442,083, the disclosures of which are hereby incorporated by reference herein, in their entirety.

As noted above, the silicon amphiphilic compounds of the present invention may contain hydrophilic polymeric moieties or saccharide moieties. It is contemplated that the hydrophilic polymeric moieties and/or saccharide moieties, and especially the hydrophilic polymer moieties, may promote the stabilization of silicon amphiphilic compositions, as well as the formation and/or stabilization of vesicle compositions. Hydrophilic polymeric moieties and/or saccharide moieties may be incorporated in the present compounds using standard synthetic organic techniques well known to those of ordinary skill in the art. For example, various materials which may be incorporated as hydrophilic polymers or saccharide moieties are commercially available. In this connection, PEG polymers of various molecular weights, as well as amino and/or hydroxy terminated PEG polymers, are commercially available from Shearwater Polymers, Inc. (Huntsville, Ala.). These materials may be condensed, for example, with a glycerol succinate using standard peptide coupling methodology, as described hereinbefore. The "pegylated" glycerol succinate may then be silylated, for example, with a standard silylating agent, such as hexamethyldisilazane. Alternatively, the "pegylated" glycerol succinate may be combined with a reactive siloxane, for example, an amine-terminated siloxane as described above. Alternatively, the hydrophilic polymer may be initially silylated or reacted with a reactive siloxane. The "pegylated" siloxane may then be condensed with the aforementioned glycerol succinate to provide the silicon amphiphilic compounds of the present invention.

As noted above, certain embodiments of the present invention involve fluorinated silicon amphiphilic compounds. These fluorinated compounds may also be prepared using standard synthetic methodology, which would be apparent to one of ordinary skill in the art, once armed with the present disclosure. Methods which may be adapted to prepare the fluorinated silicon amphiphilic compounds of the present invention are described, for example in U.S. application Ser. No. 08/465,868, filed Jun. 6, 1995, the disclosures of which are hereby incorporated by reference in their entirety.

With particular reference to fluorinated compounds in which the fluorine atoms are substituted on the $R_1$, group, the following discussion is provided. Suitable methods for preparing fluorinated amphiphilic compounds are disclosed, for example, in C. Santaella et al., *New Journal of Chemistry*, 15, 685 (1991), the disclosures of which are hereby incorporated by reference, in their entirety. Exemplary of the available methods for preparing fluorinated amphiphilic compounds are synthetic methods based on the phosphorylation of 1,2-di-(F-alkylacyl)-3-glycerol derivatives. These methods may be utilized in the preparation of perfluoroalkyl phosphatidyl-cholines and perfluoroalkyl phosphatidylethanolamines, and are disclosed, for example, in the aforementioned Santaella publication. Such methods may involve, for example, linear phosphorylating agents, including the Hirt and Berchtold. reagent (2-bromoethyldichlorophosphate (BEDP)), which is readily available in large quantities. Hirt et al., *Pharm. Acta. Helv.*, 33, 349 (1958). BEDP is highly reactive and may be used to phosphorylate sterically hindered disubstituted glycerols. Hansen et al., Lipids, 17, 453 (1982). The ammonium group may be introduced by reaction of an appropriate amine with the 1,2-diacylglycero-3-(2-bromoethyl)phosphate intermediate to give the desired phosphatidylethanolamine derivatives. This synthetic methodology is depicted in the following reaction scheme.

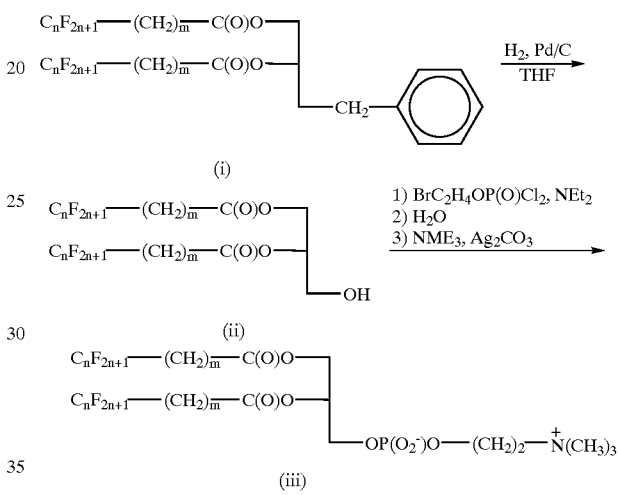

where m is an integer from 0 to about 18 and n is an integer from 1 to about 12.

The 1,2-disubstituted-3-benzylglycerol derivatives of formula (i) above may be readily synthesized in high yields (85 to 90%) by acylation of 1-benzylglycerol with the corresponding perfluoroalkanoyl halides. *Proc. Natl. Acad. Sci. USA*, 75, 4074 (1978). The benzyl protecting group can be removed by hydrogenolysis over a palladium on charcoal catalyst (Pd/C) in tetrahydrofuran (THF). *Proc. Natl. Acad. Sci. USA*, 75, 4074 (1978). Short reaction times for the hydrogenolysis of the benzyl group are preferred to avoid transesterification of the 1,2-diacylglycerol of formula (i) into the more thermodynamically stable 1,3-diacylglycerol isomer. The hydrogenolysis reaction may be monitored by conventional analytical techniques, including, for example, thin layer chromatography (TLC) and proton ($^1$H) nuclear magnetic resonance (NMR). The reaction is generally complete in about one hour with little or no transesterification. The hydrogenolysis reaction is preferably conducted in THF because both the starting material in the involved reaction (the compound of formula (i)) and the product (the compound of formula (ii)) tend to be highly soluble in THF. In addition, THF is conveniently used as the solvent in the subsequent phosphorylation step.

After hydrogenolysis, the catalyst (Pd/C) may be removed by filtration. The 1,2-diacylglycerols of formula (ii) may be reacted immediately with BEDP and an excess of triethylamine. Phosphorylation is typically completed in about 2 to about 4 hours, as measured by TLC. The remaining phosphochloride bond may be hydrolysed in aqueous base and generally requires about 22 hours for completion. When mineral bases or salts are used for hydrolysis including, for example, $Na_2CO_3$, KCl and EDTA sodium salts, the phosphate salts may be highly insoluble in water or organic solvents. Fleischer, *Methods Enzymol.* 98, 263 (1983). The brominated intermediate may be isolated as a stable and soluble hydrogenotriethylammonium salt if excess triethylamine is used. Acidification of the phosphate salts to form the corresponding acid may be difficult because the glycerol ester bonds are hydrolyzed at the necessary pH (pH of 2 to 3). Product degradation may occur also during purification over silica gel. Accordingly, it is preferred to use the phosphate salt without further purification. Nucleophilic displacement of the bromide ion by a large excess of trimethylamine may occur in a solvent mixture of $CHCl_3$/$CH_3CN$ at 45° C. over a 12 hour period. The displaced bromide ion can be precipitated by the addition of silver carbonate. The compounds of formulas (ii) and (iii) may then be converted to the siloxane compound using, for example, the methodology described above in connection with the nonfluorinated compounds.

Other methods for preparing the silicon amphiphilic compounds of the present invention, in addition to those exemplified above, would be readily apparent to one of ordinary skill in the art, once armed with the present disclosure.

As those skilled in the art will recognize, once placed in possession of the present invention, silicon amphiphilic compositions may be readily formulated from the silicon amphiphilic compounds described herein. Depending on the desired physical properties, silicon amphiphilic compositions may be prepared from the silicon amphiphilic compounds, alone or in combination with other materials, for example, materials which may act to further stabilize the resulting compositions. Generally speaking, it may be desirable to combine the silicon amphiphilic compounds with other materials, including stabilizing materials, for example, additional amphiphilic and/or amphipathic compounds, to stabilize and/or otherwise improve the properties of the compositions. Compositions which may be prepared from the present silicon amphiphilic compounds and additional stabilizing materials include, for example, suspensions, emulsions, vesicles, and the like.

A wide variety of materials which may be incorporated in the present compositions and which may serve as stabilizing materials are readily available and would be apparent to a person skilled in the art, once armed with the present disclosure. Included among such materials are additional amphipathic compounds, such as lipids, surfactants and fatty materials, as well as materials which act, for example, as dispersing agents, thickening agents, and the like. The particular stabilizing material which is ultimately combined with the present silicon compounds may be selected as desired to optimize the properties of the resulting composition. It is believed that suitable stabilizing materials are readily identifiable and that compositions of the present silicon amphiphilic compounds can be prepared by one skilled in the art without undue experimentation. In preferred form, the silicon amphiphilic compounds of the present invention may be combined with additional lipid compounds. In these embodiments, and especially compositions in the form of vesicle compositions, it may be advantageous, depending on the particular silicon amphiphilic compound and additional lipid compound selected, to prepare the compositions at a temperature below the gel to liquid crystalline phase transition temperature of the silicon amphiphilic compound and/or additional lipids. This phase transition temperature is the temperature at which a lipid bilayer will convert from a gel state to a liquid crystalline state. See, for example, Chapman et al., *J. Biol. Chem.* 1974 249, 2512–2521.

It is generally believed that vesicles which are prepared from lipids that possess higher gel state to liquid crystalline state phase transition temperatures tend to have enhanced impermeability at any given temperature. See Derek Marsh, *CRC Handbook of Lipid Bilayers* (CRC Press, Boca Raton, Fla. 1990), at p. 139 for main chain melting transitions of saturated diacyl-sn-glycero-3-phosphocholines. The gel state to liquid crystalline state phase transition temperatures of the silicon amphiphilic compounds will be readily apparent to one of ordinary skill in the art, once placed in possession of the present disclosure. The gel state to liquid crystalline state phase transition temperatures of various conventional lipids are described, for example, in Gregoriadis, ed., *Liposome Technology*, Vol. I, 1–18 (CRC Press, 1984), the disclosures of which are hereby incorporated by reference herein, in their entirety. The following table lists some of the representative lipids and their phase transition temperatures.

TABLE 1

Saturated Diacyl-sn-Glycero-3-Phosphocholines: Main Chain Melting Transition Temperatures

| Number of Carbons in Acyl Chains | Main Phase Transition Temperature (° C.) |
| --- | --- |
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

See, for example, Derek Marsh, *CRC Handbook of Lipid Bilayers*, p. 139 (CRC Press, Boca Raton, Fla. 1990).

It may be possible to enhance the stability of vesicles by incorporating in the present silicon amphiphilic compositions at least a minor amount, for example, about 1 to about 10 mole percent, based on the total amount of amphiphilic compound and/or lipid employed, of a negatively charged lipid. Suitable negatively charged lipids include, for example, phosphatidylserine, phosphatidic acid, and fatty acids. Without intending to be bound by any theory or theories of operation, it is contemplated that such negatively charged lipids provide added stability by counteracting the tendency of vesicles to rupture by fusing together. Thus, the negatively charged lipids may act to establish a uniform negatively charged layer on the outer surface of the vesicle, which may be repulsed by a similarly charged outer layer on other vesicles which are proximate thereto. In this way, the vesicles may be less prone to come into touching proximity with each other, which may lead to a rupture of the membrane or skin of the respective vesicles and consolidation of the contacting vesicles into a single, larger vesicle. A continuation of this process of consolidation will, of course, lead to significant degradation of the vesicles.

The lipids used, especially in connection with amphiphilic compositions in the form of vesicle compositions, are also preferably flexible. This means that, in the context of the present invention, the vesicles can alter their shape, for example, to pass through an opening having a diameter that is smaller than the diameter of the vesicle.

A wide variety of lipids are believed to be suitable for incorporation in the present silicon amphiphilic compositions. With particular reference to vesicle compositions, for example, micelles and/or liposomes, any of the materials or combinations thereof which are known to those skilled in the art as suitable for their preparation may be used. The lipids used may be of either natural, synthetic or semi-synthetic origin. Suitable lipids generally include, for example, fatty acids, neutral fats, phosphatides, phospholipids, glycolipids, sulfatides, aliphatic alcohols and waxes, oils, triglycerides, terpenes and steroids. It is contemplated that vesicles prepared from the novel silicon amphiphilic compounds of the present invention and conventional lipids possess highly improved and desirable properties, including improved stability properties. For example, it is contemplated that incorporating the present silicon compounds in compositions, such as lipid compositions, which are used conventionally to prepare vesicles, including liposomes, may alter the biodistribution of the vesicles in vivo, and inhibit uptake of the vesicles by the reticuloendothelial system. Thus, vesicles prepared from the compositions of the present invention may possess longer half-lives in vivo as compared to vesicles available heretofore.

Exemplary lipids which may be incorporated in the present silicon amphiphilic compositions include, for example, fatty acids, lysolipids, phospho-cholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines, which target blood clots; phosphatidylcholine with both saturated and unsaturated lipids, including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dipalmitoylphosphatidylethanolamine (DPPE) and distearoylphosphatidylethanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG), also referred to herein as "pegylated lipids," with preferred lipids bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol iso-butyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl)methyl-amino)-octadecanoic acid; N-[12-(((7'-diethylaminocoumarin-3-yl)carbonyl)methyl-amino)-octadecanoyl]-2-aminopalmitic acid; cholesteryl)4'-trimethylammonio)butanoate; N-succinyldioleoylphosphatidylethanol-amine; 1,2-dioleoyl-sn-glycerol; 1,2-dipalmitoyl-sn-3-succinylglycerol; 1,3-dipalmitoyl-2-succinylglycerol; 1-hexadecyl-2-palmitoyl-glycerophosphoethanolamine and palmitoylhomocysteine, and/or combinations thereof.

If desired, a cationic lipid may be used, such as, for example, N-[1-(2,3-dioleoyloxy)propyl]-N,N,N-trimethylammonium chloride (DOTMA), 1,2-dioleoyloxy-3-(trimethylammonio)propane (DOTAP); and 1,2-dioleoyl-3-(4'-trimethylammonio)-butanoyl-sn-glycerol (DOTB). If a cationic lipid is employed in the silicon amphiphilic compositions, the molar ratio of cationic lipid to silicon amphiphilic compound and/or non-cationic lipid may be, for example, from about 1:1000 to about 1:100. Preferably, the molar ratio of cationic lipid to silicon amphiphilic compound and/or non-cationic lipid may be from about 1:2 to about 1:10, with a ratio of from about 1:1 to about 1:2.5 being preferred. Even more preferably, the molar ratio of cationic lipid to silicon amphiphilic compound and/or non-cationic lipid may be about 1:1.

In the case of compositions which contain both cationic and non-cationic lipids, a wide variety of lipids may be employed as the non-cationic lipid. Preferably, the non-cationic lipid comprises one or more of DPPC, DPPE and dioleoylphos-phatidylethanolamine. In lieu of the cationic lipids listed above, lipids bearing cationic polymers, such as polylysine or polyarginine, as well as alkyl phosphonates, alkyl phosphinates, and alkyl phosphites, may also be used in the silicon amphiphilic compositions.

In certain preferred embodiments of the present invention, the silicon amphiphilic compositions may comprise one or more cationic lipids having the following formula

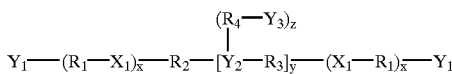
(II)

wherein:
  each of x, y and z is independently an integer from 0 to about 100;
  each $X_1$ is independently —O—, —S—, —$NR_5$, —C(=X)$_2$—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$;
  each $X_2$ is independently O or S;
  each $Y_1$ is independently a phosphate residue, N($R_6$)$_a$—, S($R_6$)$_a$—, P($R_6$)$_a$— or —$CO_2R_6$, wherein a is an integer from 1 to 3;
  each $Y_2$ is independently —N($R_6$)$_b$—, —S($R_6$)$_6$— or —P($R_6$)$_6$—, wherein b is an integer from 0 to 2;
  each $Y_3$ is independently a phosphate residue, N($R_6$)$_a$—, S($R_6$)$_a$—, P($R_6$)$_a$— or —$CO_2R_6$, wherein a is an integer from 1 to 3;
  each of $R_1$, $R_2$, $R_3$ and $R_4$ is independently alkylene of 1 to about 20 carbons;
  each $R_5$ is independently hydrogen or alkyl of 1 to about 10 carbons; and
  each $R_6$ is independently —[$R_7$—$X_3$]$_c$—$R_8$ or —$R_9$—[$X_4$—$R_{10}$]$_d$—Q, wherein:
  each of c and d is independently an integer from 0 to about 100;
  each Q is independently a phosphate residue, —N($R_{11}$)$_q$, —S($R_{11}$)$_q$, —P($R_{11}$)$_q$ or —$CO_2R_6$, wherein q is an integer from 1 to 3;
  each of $X_3$ and $X_4$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—,
  each $R_7$ is independently alkylene of 1 to about 20 carbons;
  each $R_8$ is independently hydrogen or alkyl of 1 to about 60 carbons;
  each of $R_9$ and $R_{10}$ is independently alkylene of 1 to about 20 carbons; and
  each $R_{11}$ is independently —[$R_7$—$X_3$]$_c$—$R_8$ or —$R_9$—[$X_4$—$R_{10d}$]$_d$—W,
wherein:
  each W is independently a phosphate residue, —N($R_{12}$)$_w$, —S($R_{12}$)$_w$, —P($R_{12}$)$_w$ or —$CO_2R_6$, wherein w is an integer from 1 to 3; and
  $R_{12}$ is —[$R_7$—$X_3$]$_c$—$R_8$, with the proviso that the compound of formula (II) comprises at least one, and preferably at least two, quaternary salts.

Another cationic lipid compound which may be incorporated in the compositions of the present invention is a compound of the formula $Y_1$—$R_2$—$Y_1$ (III)

wherein:
  each $Y_1$, is independently a phosphate residue, N($R_2$)$_a$—, S($R_2$)$_a$—, P($R_2$)$_a$— or —$CO_2R_2$, wherein a is an integer from 1 to 3;

$R_1$ is alkylene of 1 to about 60 carbons containing 0 to about 30 —O—, —S—, —$NR_3$— or —$X_2$—($R_3X_2$)P(=$X_2$)—$X_2$— heteroatoms or heteroatom groups;
  $R_2$ is a residue of the formula —$R_4$—[($X_1$—$R_5$)$_x$—$Y_2$]$_y$ $R_6$, wherein:
  each of x and y is independently an integer from 0 to about 100;
  each $X_1$ is independently a direct bond, —O—, —S—, —$NR_3$—, —C(=$X_2$)—, —C(=$X_2$)—N($R_3$)—, —N($R_3$)—C(=$X_2$)—, -C(=$X_2$)—O—, —O—C(=$X_2$)— or —$X_2$—($R_3X_2$)P(=$X_2$)—$X_2$—;
  each $X_2$ is independently O or S;
  each $Y_2$ is independently —S($R_2$)$_b$—, —N($R_2$)$_b$— or —P($R_2$)$_b$—, wherein b is an integer from 0 to 2;
  each $R_3$ is independently hydrogen or alkyl of 1 to about 10 carbons;
  each of $R_4$ and $R_5$ is independently a direct bond or alkylene of 1 to about 30 carbons containing 0 to about 15 —O—, —S—, —$NR_3$— or —$X_2$—($R_3X_2$)P(=$X_2$)—$X_2$— heteroatoms or heteroatom groups; and
  each $R_6$ is independently hydrogen or alkyl of 1 to about 60 carbons containing 0 to about 30 —O—, —S—, —$NR_3$— or —$X_2$—($R_3X_2$)P(=$X_2$)—$X_2$— heteroatoms or heteroatom groups; with the proviso that the compound of formula (III) comprises at least one, and preferably at least two, quaternary salts.

In yet another embodiment, the present silicon amphiphilic compositions may comprise a cationic lipid compound of the formula

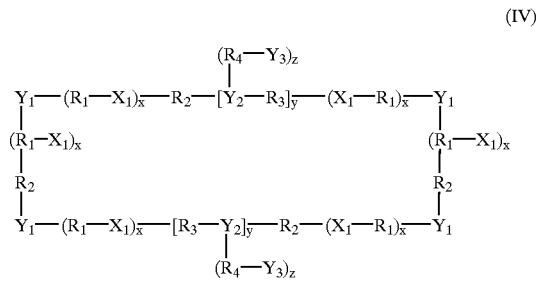
(IV)

wherein:
  each of x, y and z is independently an integer from 0 to about 100;
  each $X_1$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—;
  each $X_2$ is independently O or S;
  each $Y_1$ is independently —O—, —N($R_6$)$_a$—, —S($R_6$)$_a$ or —P($R_6$)$_a$—, wherein a is an integer from 0 to 2;
  each $Y_2$ is independently —N($R_6$)$_a$—, —S($R_6$)$_a$— or —P($R_6$)$_a$—, wherein a is an integer from 0 to 2;
  each $Y_3$ is independently a phosphate residue, N($R_6$)$_b$—, S($R_6$)$_b$—, P($R_6$)$_b$— or —$CO_2R_6$, wherein b is an integer from 1 to 3;
  each of $R_1$, $R_2$, $R_3$ and $R_4$ is independently alkylene of 1 to about 20 carbons;
  each $R_5$ is independently hydrogen or alkyl of 1 to about 10 carbons; and
  each $R_6$ is independently —[$R_7$—$X_3$]$_c$—$R_8$ or —$R_9$—[$X_4$—$R_{10}$]$_d$—Q, wherein:
  each of c and d is independentiy an integer from 0 to about 100;

each Q is independently a phosphate residue, —N(R$_{11}$)$_q$, —S(R$_{11}$)$_q$, —P(R$_{11}$)$_q$ or —CO$_2$R$_{11}$, wherein q is an integer from 1 to 3;

each of X$_3$ and X$_4$ is independently —O—, —S—, —NR$_5$—, —C(=X$_2$)—, —C(=X$_2$)—N(R$_5$)—, —N(R$_5$)—C(=X$_2$)—, —C(=X$_2$)—O—, —O-C(=X$_2$)— or —X$_2$—(R$_5$X$_2$)P(=X$_2$)—X$_2$—;

each R$_7$ is independently alkylene of 1 to about 20 carbons;

each R$_8$ is independently hydrogen or alkyl of 1 to about 60 carbons;

each of P$_9$ and R$_{10}$ is independently alkylene of 1 to about 20 carbons; and each R$_{11}$ is independently —[R$_7$—X$_3$]$_c$—R$_8$ or —R$_9$—[X$_4$—R$_{10}$]$_d$—W, wherein:

each W is independently a phosphate residue, —N(R$_{12}$)$_w$, —S(R$_{12}$)$_w$, —P(R$_{12}$)$_w$ or —CO$_2$R$_{12}$, wherein w is an integer from 1 to 3; and R$_{12}$ is —[R$_7$—X$_3$]$_c$—R$_8$; with the proviso that the compound of formula (IV) comprises at least one, and preferably at least two, quaternary salts. The cationic lipid compounds which are described generally above are set forth in copending U.S. application Ser. No. 08/391,938, the disclosures of which are hereby incorporated by reference herein, in their entirety.

In certain preferred embodiments, the silicon amphiphilic compositions further comprise phospholipids, particularly one or more of DPPC, DPPE, DPPA, DSPC, DSPE, DSPG, and DAPC (20 carbons), preferably, DPPC, DPPE and/or DPPA, and more preferably, DPPC and DPPA.

In addition, saturated and unsaturated fatty acids may be employed in the present silicon amphiphilic compositions, and these fatty acids may include compounds that preferably contain from about 12 carbons to about 22 carbons, in linear or branched form. Hydrocarbon groups consisting of isoprenoid units and/or prenyl groups can be used as well. Examples of saturated fatty acids that are suitable include, for example, lauric, myristic, palmitic, and stearic acids. Suitable unsaturated fatty acids that may be used include, for example, lauroleic, physeteric, myristoleic, palmitoleic, petroselinic, and oleic acids. Examples of branched fatty acids that may be used include, for example, isolauric, isomyristic, isopalmitic, and isostearic acids.

As noted above, the present silicon amphiphilic compositions also preferably comprise a gas, such as an inert gas. The gas provides the silicon amphiphilic compositions with enhanced reflectivity, particularly in connection with vesicle compositions in which the gas is entrapped within the vesicles. This may increase their effectiveness as contrast agents.

Preferred gases are gases which are inert and which are biocompatible, that is, gases which are not injurious to biological function. Preferred gases include those selected from the group consisting of air, noble gases, such as helium, rubidium hyperpolarized xenon, hyperpolarized argon, hyperpolarized helium, neon, argon and xenon, carbon dioxide, nitrogen, fluorine, oxygen, sulfur-based gases, such as sulfur hexafluoride and sulfur tetrafluoride, fluorinated gases, including, for example, partially fluorinated gases or completely fluorinated gases. Exemplary fluorinated gases include the fluorocarbon gases, such as the perfluorocarbon gases, and mixtures thereof. Paramagnetic gases, such as $^{17}O_2$ may also be used in the silicon amphiphilic compositions.

In preferred embodiments, the gas comprises a fluorinated gas. Such fluorinated gases include materials which contain one, or more than one, fluorine atom. Preferred are gases which contain more than one fluorine atom, with perfluorocarbons (that is, fully fluorinated fluorocarbons) being more preferred. Preferably, the perfluorocarbon gas is selected from the group consisting of perfluoromethane, perfluoroethane, perfluoropropane, perfluorobutane, perfluoropentane, perfluorocyclobutane and mixtures thereof. More preferably, the perfluorocarbon gas is perfluoropropane or perfluorobutane, with perfluoropropane being particularly preferred. Another preferable gas is sulfur hexafluoride. Yet another preferable gas is heptafluoropropane, including 1,1,1,2,3,3,3-heptafluoropropane and its isomer, 1,1,2,2,3,3,3-heptafluoropropane. It is contemplated that mixtures of different types of gases, such as mixtures of a perflucrocarbon gas and another type of gas, such as air, can also be used in the compositions of the present invention. Other gases, including the gases exemplified above, would be readily apparent to one skilled in the art based on the present disclosure.

In certain preferred embodiments, a gas, for example, air or a perfluorocarbon gas, is combined with a liquid perfluorocarbon, such as perfluoropentane, perfluorohexane, perfluoroheptane, perfluorooctylbromide (PFOB), perfluorodecalin, perfluorododecalin, perfluorooctyliodide, perfluorotripropylamine and perfluorotributylamine.

It may also be desirable to incorporate in the silicon amphiphilic compositions a precursor to a gaseous substance. Such precursors include materials that are capable of being converted to a gas in vivo. Preferably, the gaseous precursor is biocompatible, and the gas produced in vivo is biocompatible also.

Among the gaseous precursors which are suitable for use in compositions described herein are agents which are sensitive to pH. These agents include materials that are capable of evolving gas, for example, upon being exposed to a pH that is neutral or acidic. Examples of such pH sensitive agents include salts of an acid which is selected from the group consisting of inorganic acids, organic acids and mixtures thereof. Carbonic acid (H$_2$CO$_3$) is an example of a suitable inorganic acid, and aminomalonic acid is an example of a suitable organic acid. Other acids, including inorganic and organic acids, would be readily apparent to one skilled in the art based on the present disclosure.

Gaseous precursors which are derived form salts are preferably selected from the group consisting of alkali metal salts, ammonium salts and mixtures thereof. More preferably, the salt is selected from the group consisting of carbonate, bicarbonate, sesquecarbonate, aminomalonate and mixtures thereof.

Examples of suitable gaseous precursor materials which are derived from salts include, for example, lithium carbonate, sodium carbonate, potassium carbonate, lithium bicarbonate, sodium bicarbonate, potassium bicarbonate, magnesium carbonate, calcium carbonate, magnesium bicarbonate, ammonium carbonate, ammonium bicarbonate, ammonium sesquecarbonate, sodium sesquecarbonate, sodium aminomalonate and ammonium aminomalonate. Aminomalonate is well known in the art, and its preparation is described, for example, in Thanassi, *Biochemistry*, Vol. 9, no. 3, pp. 525–532 (1970); Fitzpatrick et al., *Inorganic Chemistry*, Vol. 13, no. 3 pp. 568–574 (1974); and Stelmashok et al., *Koordinatsionnaya Khimiya*, Vol. 3, no. 4, pp. 524–527 (1977). The disclosures of these publications are hereby incorporated herein by reference.

In addition to, or instead of being sensitive to changes in pH, the gaseous precursor materials may also comprise compounds which are sensitive to changes in temperature. Exemplary of suitable gaseous precursors which are sensitive to changes in temperature are the perfluorocarbons. As the artisan will appreciate, a particular perfluorocarbon may exist in the liquid state when the compositions are first made, and are thus used as a gaseous precursor. Alternatively, the perfluorocarbon may exist in the gaseous state when the compositions are made, and are thus used directly as a gas. Whether the perfluorocarbon is used as a liquid or a gas generally depends on its liquid/gas phase transition temperature, or boiling point. For example, a preferred perfluorocarbon, perfluoropentane, has a liquid/gas phase transition temperature (boiling point) of 29.5° C. This means that perfluoropentane is generally a liquid at room temperature (about 25° C.), but is converted to a gas within the human body, the normal temperature of which is about 37° C., which is above the transition temperature of perfluoropentane. Thus, under normal circumstances, perfluoropentane is a gaseous precursor. As a further example, there are the homologs of perfluoropentane, namely perfluorobutane and perfluorohexane. The liquid/gas transition of perfluorobutane is 4° C. and that of perfluorohexane is 57° C. Thus, perfluorobutane can be useful as a gaseous precursor, although more likely as a gas, whereas perfluorohexane can be useful as a gaseous precursor because of its relatively high boiling point. As known to one of ordinary skill in the art, the effective boiling point of a substance may be related to the pressure to which that substance is exposed. This relationship is exemplified by the ideal gas law: PV=nRT, where P is pressure, V is volume, n is moles of substance, R is the gas constant, and T is temperature. The ideal gas law indicates that as pressure increases, the effective boiling point increases also. Conversely, as pressure decreases, the effective boiling point decreases.

A wide variety of materials can be used as gaseous precursors in the present compositions. It is only required that the material be capable of undergoing a phase transition to the gas phase upon passing through the appropriate temperature. Suitable gaseous precursors include, for example, hexafluoroacetone, isopropyl acetylene, allene, tetrafluoroallene, boron trifluoride, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiyne, 1-fluorobutane, 2-methylbutane, perfluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluorobutyne, 3-methyl-1-butyne, perfluoro-2-butyne, 2-bromo-butyraldehyde, carbonyl sulfide, crotononitrile, cyclobutane, methylcyclobutane, octafluorocyclobutane, perfluorocyclobutene, 3-chlorocyclopentene, perfluorocyclo-pentane, octafluoro-cyclopentene, cyclopropane, perfluorocyclopropane, 1,2-dimethylcyclopropane, 1,1-dimethylcyclopropane, 1,2-dimethylcyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis (dimethylphosphine) amine, perfluorohexane, perfluoroheptane, perfluorooctane, 2,3-dimethyl-2-norbornane, perfluorodimethyl-amine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, perfluoroethane, nitropentafluoroethane, nitrosopenta-fluoroethane, perfluoroethyl-amine, ethyl vinyl ether, 1,1-dichloroethane, 1,1-dichloro-1,2-difluoroethane, 1,2-difluoroethane, methane, trifluoromethanesulfonylchloride, trifluoromethanesulfonylfluoride, bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, iodomethane, iodotrifluoromethane, nitrotrifluoro-methane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neopentane, nitrous oxide, 1,2,3-nonadecanetricarboxylic acid 2-hydroxytrimethyl ester, 1-nonene-3-yne, 1,4-pentadiene, n-pentane, perfluoropentane, 4-amino4-methylpentan-2-one, 1-pentene, 2-pentene (cis and trans), 3-bromopent-1-ene, perfluoropent-1-ene, tetrachloro-phthalic acid, 2,3,6-trimethylpiperidine, propane, 1,1,1,2,2,3-hexafluoropropane, 1,2-epoxy-propane, 2,2-difluoropropane, 2-aminopropane, 2-chloropropane, heptafluorol-nitropropane, heptafluoro-1-nitrosopropane, perfluoropropane, propene, hexafluoro-propane, 1,1,1,2,3,3-hexafluoro-2,3-dichloropropane, 1-chloropropane, chloropropane-(trans), 2-chloropropane, 3-fluoropropane, propyne, 3,3,3-trifluoropropyne, 3-fluorostyrene, sulfur (di)-decafluoride ($S_2F_{10}$), 2,4-diaminotoluene, trifluoroacetonitrile, trifluoromethyl peroxide, trifluoromethyl sulfide, tungsten hexafluoride, vinyl acetylene and vinyl ether.

Perfluorocarbons are both preferred gases and preferred gaseous precursors for use in connection with the compositions of the present invention. Included among such perfluorocarbons are saturated perfluorocarbons, unsaturated perfluorocarbons, and cyclic perfluorocarbons. The saturated perfluorocarbons, which are usually preferred, have the formula $C_nF_{2n+2}$, where n is an integer from 1 to about 12, preferably about 2 to about 10, more preferably about 3 to about 8, and even more. preferably about 3 to about 6. Suitable perfluorocarbons include, for example, perfluoromethane, perfluoroethane, perfluoropropane, perfluorobutane, perfluorocyclobutane, perfluoropentane, perfluorohexane, perfluoroheptane, perfluorooctane and perfluorononane. Preferably, the perfluorocarbon is selected from the group consisting of perfluoropropane, perfluorobutane, perfluorocyclobutane, perfluoropentane, perfluorohexane, perfluoroheptane and perfluorooctane, with perfluoropropane being particularly preferred. Cyclic perfluorocarbons, which have the formula $C_nF_{2n}$, where n is from 3 to 8, preferably 3 to 6, may also be preferred, and include, for example, hexafluorocyclopropane, octafluorocyclobutane, and decafluorocyclopentane. Generally speaking, perfluorocarbons containing about 4 carbons or less are gases at room temperature, whereas perfluorocarbons containing from about 5 to about 12 carbons are liquids at room temperature. In either case, both liquid and/or gaseous perfluorocarbons may be incorporated in the compositions of the present invention.

In addition to the perfluorocarbons, it may be desirable to utilize stable fluorocarbons which are not completely fluorinated. Such fluorocarbons include heptafluoropropane, for example, 1,1,1,2,3,3,3-heptafluoropropane and its isomer, 1,1,2,2,3,3,3-heptafluoropropane.

The gaseous precursor materials may be also photoactivated materials, such as diazonium ion and aminomalonate. As discussed more fully hereinafter, certain silicon amphiphilic compositions, and particularly vesicle compositions, may be formulated so that gas is formed at the target tissue or by the action of sound on the lipid composition. Examples of gaseous precursors are described, for example, in U.S. Pat. Nos. 5,088,499 and 5,149,319, the disclosures of which are hereby incorporated herein by reference, in their entirety. Other gaseous precursors, in addition to those exemplified above, will be apparent to one skilled in the art based on the present disclosure.

The gaseous substances and/or gaseous precursors are preferably incorporated in the silicon amphiphilic compositions irrespective of the physical nature of the composition. Thus, it is contemplated that the gaseous substances and/or precursors thereto may be incorporated, for example, in compositions in which the silicon amphiphilic compounds and optional additional stabilizing materials, such as lipids, are aggregated randomly, as well as in vesicle compositions, such as micelles and liposomes. Incorporation of the gaseous substances and/or precursors thereto in the silicon amphiphilic compositions may be achieved by using any of a number of methods. For example, the formation of gas filled vesicles can be achieved by shaking or otherwise agitating an aqueous mixture which comprises a gas or gaseous precursor and one or more silicon amphiphilic compounds, and optional additional stabilizing materials. This promotes the formation of stabilized vesicles within which the gas or gas precursor is encapsulated.

In addition, a gas may be bubbled directly into an aqueous mixture of vesicle forming compounds, including silicon amphiphilic compounds and additional stabilizing materials. Alternatively, a gas instillation method can be used as disclosed, for example, in U.S. Pat. Nos. 5,352,435 and 5,228,446, the disclosures of which are hereby incorporated herein by reference, in their entirety. Suitable methods for incorporating the gas or gas precursor in cationic lipid compositions are disclosed also in U.S. Pat. No. 4,865,836, the disclosures of which are hereby incorporated herein by reference. Other methods would be apparent to one skilled in the art based on the present disclosure. Preferably, the gas may be instilled in the silicon amphiphilic compositions after or during the addition of the stabilizing material and/or during formation of vesicles.

In preferred embodiments, the gaseous substances and/or gaseous precursor materials are incorporated in vesicle compositions, with micelles and liposomes being preferred. As discussed in detail below, vesicles in which a gas or gaseous precursor or both are encapsulated are advantageous in that they provide improved reflectivity in vivo.

As discussed more fully hereinafter, it is preferred that the silicon amphiphilic compositions, and especially vesicle compositions, be formulated from silicon amphiphilic compounds and additional stabilizing materials, especially lipids, to promote the formation of stable vesicles. In addition, it is also preferred that the silicon amphiphilic compositions comprise a highly stable gas as well. The phrase "highly stable gas" refers to a gas which has limited solubility and diffusability in aqueous media. Exemplary highly stable gases include perfluorocarbons since they are generally less diffusible and relatively insoluble in aqueous media. Accordingly, their use may promote the formation of highly stable vesicles.

In certain embodiments, it may be desirable to use a fluorinated compound, especially a perfluorocarbon compound, which may be in the liquid state at the temperature of use of the silicon amphiphilic compositions, including, for example, the in vivo temperature of the human body, to assist or enhance the stability of the compositions, and especially, gas filled vesicles. Suitable fluorinated compounds include, for example, fluorinated surfactants, such as fluorinated surfactants which are commercially available as ZONYL® surfactants (the DuPont Company, Wilmington, Del.), as well as liquid perfluorocarbons, such as for example, perfluorooctylbromide (PFOB), perfluorodecalin, perfluorododecalin, perfluorooctyliodide, perfluorotripropylamine, and perfluorotri-butylamine. In general, perfluorocarbons comprising about six or more carbon atoms will be liquids at normal human body temperature. Among these perfluorocarbons, perfluorooctylbromide and perfluorohexane, which are liquids at room temperature, are preferred. The gas which is present may be, for example, nitrogen or perfluoropropane, or may be derived from a gaseous precursor, which may also be a perfluorocarbon, for example, perfluoropentane. In the latter case, the silicon amphiphilic compositions may be prepared from a mixture of perfluorocarbons, which for the examples given, would be perfluoropropane (gas) or perfluoropentane (gaseous precursor) and perfluorooctylbromide (liquid). Although not intending to be bound by any theory or theories of operation, it is believed that, in the case of vesicle compositions, the liquid fluorinated compound may be situated at the interface between the gas and the membrane or wall surface of the vesicle. There may be thus formed a further stabilizing layer of liquid fluorinated compound on the internal surface of the stabilizing compound, for example, a silicon amphiphilic compound and/or biocompatible lipid used to form the vesicle, and this perfluorocarbon layer may also prevent the gas from diffusing through the vesicle membrane. A gaseous precursor, within the context of the present invention, is a liquid at the temperature of manufacture and/or storage, but becomes a gas at least at or during the time of use.

Thus, it has been discovered that a liquid fluorinated compound, such as a perfluorocarbon, when combined with a gas or gaseous precursor ordinarily used to make the silicon amphiphilic compositions described herein, may confer an added degree of stability not otherwise obtainable with the gas or gaseous precursor alone. Thus, it is within the scope of the present invention to utilize a gas or gaseous precursor, such as a perfluorocarbon gaseous precursor, for example, perfluoropentane, together with a perfluorocarbon which remains liquid after administration to a patient, that is, whose liquid to gas phase transition temperature is above the body temperature of the patient, for example, perfluorooctylbromide. Perfluorinated surfactants, such as ZONYL® fluorinated surfactants, may be used to stabilize the silicon amphiphilic compositions, and to act, for example, as a coating for vesicles. Preferred perfluorinated surfactants are the partially fluorinated phosphocholine surfactants. In these preferred fluorinated surfactants, the dual alkyl compounds may be fluorinated at the terminal alkyl chains and the proximal carbons may be hydrogenated. These fluorinated phosphocholine surfactants may be incorporated in the compositions of the present invention.

In addition to vesicle compositions, the silicon amphiphilic compounds of the present invention may also be employed in emulsions, including oil-in-water emulsions, as well as other binary or multiple phase systems. Silicon oil nanodroplet emulsions and microdroplet suspensions, oil-in-water and oil-in-oil systems are among the numerous multiphasic mixtures that may be stabilized by the novel silicon amphiphilic compounds of the present invention.

In connection with embodiments involving vesicle compositions, the size of the vesicles can be adjusted for the particular intended end use including, for example, diagnostic and/or therapeutic use. The size of the vesicles may preferably range from about 30 nanometers (nm) to about 100 micrometers ($\mu$m) in diameter, and all combinations and subcombinations of ranges therein. More preferably, the vesicles have diameters of from about 100 nm to about 10 $\mu$m, with diameters of from about 200 nm to about 7 $\mu$m being even more preferred. In connection with particular uses, for example, intravascular use, including magnetic resonance imaging of the vasculature, it may be preferred that the vesicles be no larger that about 30 $\mu$m in diameter, with smaller vesicles being preferred, for example, vesicles of no larger than about 12 $\mu$m in diameter. In certain preferred embodiments, the diameter of the vesicles may be about 7 $\mu$m or less, with vesicles having a mean diameter of about 5 $\mu$m or less being more preferred, and vesicles having a mean diameter of about 3 $\mu$m or less being even more preferred. It is contemplated that these smaller vesicles may perfuse small vascular channels, such as the microvasculature, while at the same time providing enough space or room within the vascular channel to permit red blood cells to slide past the vesicles.

The size of the gas filled vesicles can be adjusted, if desired, by a variety of procedures including, for example, shaking, microemulsification, vortexing, extrusion, filtration, sonication, homogenization, repeated freezing and thawing cycles, extrusion under pressure through pores of defined size, and similar methods.

As noted above, compositions employed herein may also include, with respect to their preparation, formation and use, gaseous precursors that can be activated to change from a liquid or solid state into a gas by temperature, pH, light, and energy (such as ultrasound). The gaseous precursors may be made into gas by storing the precursors at reduced pressure. For example, a vial stored under reduced pressure may create a headspace of perfluoropentane or perfluorohexane gas, useful for creating a preformed gas prior to injection. Preferably, the gaseous precursors may be activated by temperature. Set forth below is a table listing a series of gaseous precursors which undergo phase transitions from liquid to gaseous states at relatively close to normal body temperature (37° C.) or below, and the size of the emulsified roplets that would be required to form a vesicle of a maximum size of 10 $\mu$m.

TABLE 2

Physical CHaracteristics of Gaseous Precursors and Diameter of Emulsified Droplet to Form a 10 $\mu$m Vesicle*

| Compound | Molecular Weight | Boiling Point (° C.) | Density | Diameter ($\mu$m) of emulsified droplet to make 10 micron vesicle |
|---|---|---|---|---|
| perfluoro pentane | 288.04 | 29.5 | 1.7326 | 2.9 |
| 1-fluorobutane | 76.11 | 32.5 | 0.67789 | 1.2 |
| 2-methyl butane (isopentane) | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluoro cyclobutane | 200.04 | −5.8 | 1.48 | 2.8 |
| decafluoro butane | 238.04 | −2 | 1.517 | 3.0 |
| hexafluoro ethane | 138.01 | −78.1 | 1.607 | 2.7 |

*Source: Chemical Rubber Company Handbook of Chemistry and Physics, Robert C. Weast and David R. Lide, eds., CRC Press, Inc. Boca Raton, Florida (1989-1990).

The perfluorocarbons, as already indicated, are preferred for use as the gas or gaseous precursors, as well as additional stabilizing components.

As noted above, it is preferred to optimize the utility of the silicon amphiphilic compositions, especially vesicle compositions, by using gases of limited solubility. The phrase "limited solubility" refers to the ability of the gas to diffuse out of the vesicles by virtue of its solubility in the surrounding aqueous medium. A greater solubility in the aqueous medium imposes a gradient with the gas in the vesicle such that the gas may have a tendency to diffuse out of the vesicle. A lesser solubility in the aqueous milieu, may, on the other hand, decrease or eliminate the gradient between the vesicle and the interface such that diffusion of the gas out of the vesicle may be impeded. Preferably, the gas entrapped in the vesicle has a solubility less than that of oxygen, that is, about 1 part gas in about 32 parts water. See *Matheson Gas Data Book*, 1966, Matheson Company Inc. More preferably, the gas entrapped in the vesicle possesses a solubility in water less than that of air; and even more preferably, the gas entrapped in the vesicle possesses a solubility in water less than that of nitrogen.

In addition to the silicon amphiphilic compound and additional optional lipids discussed above, the compositions described herein may comprise one or more additional stabilizing materials. Exemplary of such additional stabilizing materials are, for example, biocompatible polymers. These additional stabilizing materials may be employed to desirably assist in the formation of vesicles and/or to assure substantial encapsulation of the gases or gaseous precursors. Even for relatively insoluble, non-diffusible gases, such as perfluoropropane or sulfur hexafluoride, improved vesicle compositions may be obtained when one or more stabilizing materials are utilized in the formation of the gas and gaseous precursor filled vesicles. These compounds may help improve the stability and the integrity of the vesicles with regard to their size, shape and/or other attributes.

The terms "stable" or "stabilized", as used herein in connection with vesicle compositions, means that the vesicles may be substantially resistant to degradation, including, for example, loss of vesicle structure or encapsulated gas or gaseous precursor, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein, including gas and gaseous precursor filled vesicles, may also be stable even under adverse conditions, such as temperatures and pressures which are above or below those experienced under normal ambient conditions.

The stability of the vesicles described herein may be attributable, at least in part, to the materials from which the vesicles are made, including, for example, the silicon amphiphilic compounds of the present invention, and it may be unnecessary to employ additional stabilizing materials, including additional lipid compounds and/or polymers, although it is optional and may be preferred to do so. Such additional stabilizing materials and their characteristics are described more fully hereinafter. In addition, because of the.ease of formulation, including the capability of preparing vesicles immediately prior to administration, these vesicles may be conveniently made on site.

The biocompatible polymers useful as stabilizing materials for preparing the gas and gaseous precursor filled vesicles may be of natural, semi-synthetic (modified natural) or synthetic origin. As used herein, the term polymer denotes a compound comprised of two or more repeating monomeric units, and preferably 10 or more repeating monomeric units. The phrase semi-synthetic polymer (or modified natural polymer), as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, polydextrose, pustulan, chitin, agarose, keratan, chondroitan, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof. Methods for the preparation of vesicles which employ polymers as stabilizing compounds will be readily apparent to those skilled in the art, once armed with the present disclosure, when the present disclosure is coupled with information known in the art, such as that described and referred to in Unger, U.S. Pat. No. 5,205,290, the disclosures of which are hereby incorporated herein by reference, in their entirety.

Particularly preferred embodiments of the present invention may involve vesicles which comprise in addition to at least one silicon amphiphilic compound, one or more of the following components: (1) a neutral lipid, for example, a nonionic or zwitterionic lipid, (2) a negatively charged lipid, and (3) a lipid bearing a stabilizing material, for example, a hydrophilic polymer. It will be understood to one of ordinary skill in the art, once armed with the present disclosure, that the silicon amphiphilic compounds of the present invention, including the silicon amphiphilic compounds of formula (I), may themselves contain one or more of components (1) to (3). For example, the silicon amphiphilic compounds may comprise lipid moieties which are neutral, that is, nonionic or zwitterionic. Alternatively, the silicon amphiphilic compound may comprise a lipid moiety which possess a net negative charge. Also, the silicon amphiphilic compound may. comprise a lipid moiety that bears a stabilizing material, for example, a hydrophilic polymer. In the case of the preferred embodiments represented by the compounds of formula (I), the hydrophilic polymeric stabilizing materials are exemplified by the diradical "Z."

In compositions which comprise separate negatively charged lipids and/or lipids bearing stabilizing material (polymer), the amount of the negatively charged material is preferably greater than about 1 mole percent of the total lipid and silicon amphiphilic compound present, and the amount of lipid bearing a hydrophilic polymer will be greater than about 1 mole percent of the total lipid and silicon amphiphilic compound present. Exemplary and preferred negatively charged lipids include phosphatidic acids. The lipid bearing a hydrophilic polymer will desirably be a lipid covalently linked to the polymer, and the polymer will preferably have a weight average molecular weight which ranges from about 400 to about 100,000, and all combinations and subcombinations of ranges therein. Suitable hydrophilic polymers are preferably selected from the group consisting of polyethylene glycol (PEG), polypropylene glycol, polyvinyl alcohol, and polyvinylpyrrolidone and copolymers thereof, with PEG polymers being preferred. Preferably, the PEG polymer has a molecular weight of from about 1000 to about 7500, with molecular weights of from about 2000 to about 5000 being more preferred. The PEG or other polymer may be bound to the lipid, for example, DPPE, through a covalent bond, such as an amide, carbamate or amine linkage. In addition, the PEG or other polymer may be linked to a targeting ligand, or other lipids, with a covalent bond including, for example, amide, ester, ether, thioester, thioamide or disulfide bonds. Where the hydrophilic polymer is PEG, a lipid bearing such a polymer will be said to be "pegylated." In preferred form, the lipid bearing a hydrophilic polymer may be DPPE-PEG, including, for example, DPPE-PEG5000, which refers to DPPE having a polyethylene glycol polymer of a mean weight average molecular weight of about 5000 attached thereto (DPPE-PEG5000). Another suitable pegylated lipid is distearoylphosphatidylethanol-amine-polyethylene glycol 5000 (DSPE-PEG5000).

In certain preferred embodiments of the present invention, the silicon amphiphilic compositions may comprise about 80 to about 90 mole % DPPC, about 5 to about 15 mole % DPPA and about 5 to about 15 mole % silicon amphiphilic compound. Especially preferred are compositions which comprise DPPC, DPPA and silicon amphiphilic compound in a mole % ratio of 82:10:8, respectively. DPPC is substantially neutral, since the phosphatidyl portion is negatively charged and the choline portion is positively charged. Consequently, DPPA, which is negatively charged, may be added to enhance stabilization in accordance with the mechanism described above. In preferred embodiments, the silicon amphiphilic compound possesses a PEG moiety to which a silicon residue is covalently attached. This provides a pegylated material bound to the lipid membrane or skin of the vesicle by the silicon amphiphilic compound, with the PEG moiety free to surround the vesicle membrane or skin, and thereby form a physical barrier to various enzymatic and other endogenous agents in the body whose function is to degrade such foreign materials. The PEG group may provide more vesicles of a smaller size which are safe and stable to pressure when combined with other lipids, such as DPPC and DPPA, in the given ratios. It is also theorized that the pegylated material, because of its structural similarity to water, may be able to defeat the action of the macrophages of the human immune system, which would otherwise tend to surround and remove the foreign object. The result is an increase in the time during which the stabilized vesicles may function as diagnostic imaging contrast media.

The vesicle compositions may further comprise other materials, in addition to the silicon amphiphilic compounds and optional stabilizing materials described above, provided that the vesicles so prepared meet the stability and other criteria set forth herein. These materials may be basic and fundamental, and form the primary basis for creating or establishing the stabilized gas and gaseous precursor filled vesicles. On the other hand, they may be auxiliary, and act as subsidiary or supplementary agents which can enhance the functioning of the basic stabilizing material or materials, or contribute some desired property in addition to that afforded by the basic stabilizing material.

However, it is not always possible to determine whether a given material is a basic or an auxiliary agent, since the functioning of the material in question is determined empirically, for example, by the results produced with respect to producing stabilized vesicles. As examples of how these basic and auxiliary materials may function, it has been observed that the simple combination of a biocompatible lipid and water or saline when shaken will often give a cloudy solution subsequent to autoclaving for sterilization. Such a cloudy solution may function as a contrast agent, but is aesthetically objectionable and may imply instability in the form of undissolved or undispersed lipid particles. Cloudy solutions may be also undesirable where the undissolved particulate matter has a diameter of greater than about 7 μm, and especially greater than about 10 μm. Manufacturing steps, such as sterile filtration, may also be problematic with solutions which contain undissolved particulate matter. Thus, propylene glycol may be added to remove this cloudiness by facilitating dispersion or dissolution of the lipid particles. The propylene glycol may also function as a wetting agent which can improve vesicle formation and stabilization by increasing the surface tension on the vesicle membrane or skin. It is possible that the propylene glycol can also function as an additional layer that may coat the membrane or skin of the vesicle, thus providing additional stabilization. As examples of such further basic or auxiliary stabilizing materials, there are conventional surfactants which may be used; see D'Arrigo U.S. Pat. Nos. 4,684,479 and 5,215,680.

Additional auxiliary and basic stabilizing materials include such agents as peanut oil, canola oil, olive oil, safflower oil, corn oil, or any other oil commonly known to be ingestible which is suitable for use as a stabilizing compound in accordance with the teachings herein. Various auxiliary and basic stabilizing materials are disclosed, for example, in U.S. application Ser. No. 08/444,574, filed May 19, 1995, the disclosures of which are incorporated herein by reference, in their entirety.

In addition, compounds used to make mixed micelle systems may be suitable for use as basic or auxiliary stabilizing materials, and these include, for example, lauryltrimethylammonium bromide (dodecyl-), cetyltrimethylammonium bromide (hexadecyl-), myristyltrimethylammonium bromide (tetradecyl-), alkyldimethylbenzylammonium chloride (where alkyl is $C_{12}$, $C_{14}$ or $C_{16}$,), benzyldimethyldodecylammonium bromide/chloride, benzyldimethyl hexadecylammonium bromide/chloride, benzyldimethyl tetradecylammonium bromide/chloride, cetyldimethylethylammonium bromide/chloride, or cetylpyridinium bromide/chloride.

It has also been found that the gas and gaseous precursor filled vesicles used in the present invention may be controlled according to size, solubility and heat stability by choosing from among the various additional or auxiliary stabilizing materials described herein. These materials can affect these parameters of the vesicles not only by their physical interaction with the membranes, but also by their ability to modify the viscosity and surface tension of the surface of the gas and gaseous precursor filled vesicle. Accordingly, the gas and gaseous precursor filled vesicles of the present invention may be favorably modified and further stabilized, for example, by the addition of one or more of a wide variety of (a) viscosity modifiers, including, for example, carbohydrates and their phosphorylated and sulfonated derivatives; polyethers, preferably with molecular weight ranges between 400 and 100,000; and di- and trihydroxy alkanes and their polymers, preferably with molecular weight ranges between 200 and 50,000; (b) emulsifying and/or solubilizing agents including, for example, acacia, cholesterol, diethanolamine, glyceryl monostearate, lanolin alcohols, lecithin, mono- and di-glycerides, monoethanolamine, oleic acid, oleyl alcohol, poloxamer, for example, poloxamer 188, poloxamer 184, and poloxamer 181, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax; (c) suspending and/or viscosity-increasing agents, including, for example, acacia, agar, alginic acid, aluminum mono-stearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropyl methylcellulose, magnesium-aluminum-silicate, Zeolites®, methylcellulose, pectin, polyethylene oxide, povidone, propylene glycol alginate, silicon dioxide, sodium alginate, tragacanth, xanthan gum, α-d-gluconolactone, glycerol and mannitol; (d) synthetic suspending agents, such as polyethylene glycol (PEG), polyvinylpyrrolidone (PVP), polyvinyl alcohol (PVA), polypropylene glycol (PPG), and polysorbate; and (e) tonicity raising agents which stabilize and add tonicity, including, for example, sorbitol, mannitol, trehalose, sucrose, propylene glycol and glycerol.

A wide variety of methods are available for the preparation of the present silicon amphiphilic compositions, including vesicle compositions, such as micelles and/or liposomes. Included among these methods are, for example, shaking, drying, gas-installation, spray drying, and the like. Suitable methods for preparing vesicle compositions are described, for example, in U.S. Pat. No. 5,469,854, the disclosures of which are incorporated herein by reference.

With particular reference to the preparation of micelle compositions, the following discussion is provided. Micelles may be prepared using any one of a variety of conventional micellar preparatory methods which will be apparent to those skilled in the art. These methods typically involve suspension of the silicon amphiphilic compound, and optional stabilizing materials, namely, lipid compounds, in an organic solvent, evaporation of the solvent, resuspension in an aqueous medium, sonication and centrifugation. The foregoing methods, as well as others, are discussed, for example, in Canfield et al., *Methods in Enzymology*, Vol. 189, pp. 418–422 (1990); El-Gorab et al, *Biochem. Biophys. Acta*, Vol. 306, pp. 58–66 (1973); *Colloidal Surfactant*, Shinoda, K., Nakagana, Tamamushi and Isejura, Academic Press, N.Y. (1963) (especially "The Formation of Micelles", Shinoda, Chapter 1, pp. 1–88); *Catalysis in Micellar and Macromolecular Systems*, Fendler and Fendler, Academic Press, N.Y. (1975). The disclosures of each of the foregoing publications are incorporated by reference herein, in their entirety.

As noted above, the vesicle composition may comprise liposomes. In any given liposome, the silicon amphiphilic compounds, and additional optional stabilizing materials, may be in the form of a monolayer or bilayer, and the mono- or bilayers may be used to form one or more mono- or bilayers. In the case of more than one mono- or bilayer, the mono- or bilayers are generally concentric. Thus, the materials described herein may be used to form unilamellar liposomes (comprised of one monolayer or bilayer), oligolamellar liposomes (comprised of two or three monolayers or bilayers) or multilamellar liposomes (comprised of more than three monolayers or bilayers).

A wide variety of methods are available in connection with the preparation of liposome compositions. Accordingly, the liposomes may be prepared using any one of a variety of conventional liposomal preparatory techniques which will be apparent to those skilled in the art. These techniques include, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the vesicles in various fashions. See, e.g., Madden et al., *Chemistry and Physics of Lipids*, 1990 53, 37–46, the disclosures of which are hereby incorporated herein by reference in their entirety. Suitable freeze-thaw techniques are described, for example, in International Application Serial No. PCT/US89/05040, filed Nov. 8, 1989, the disclosures of which are incorporated herein by reference in their entirety. Methods which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing. This may be achieved, for example, by the use of a mechanical shaking device, such as a Wig-L-Bug™ (Crescent Dental, Lyons, Ill.), a Mixomat, sold by Degussa AG (Frankfurt, Germany), a Capmix, sold by Espe Fabrik Pharmazeutischer Praeparate GMBH & Co. (Seefeld, Oberay Germany), a Silamat Plus, sold by Vivadent (Lechtenstein), or a Vibros, sold by Quayle Dental, (Sussex, England). Conventional microemulsification equipment, such as a Microfluidizer™ (Microfluidics, Woburn, Mass.) may also be used.

Spray drying may be also employed to prepare the gas-filled vesicles. Utilizing this procedure, the silicon amphiphilic compound, and optional additional stabilizing materials, may be pre-mixed in an aqueous environment and then spray dried to produce gas-filled vesicles. The vesicles may be stored under a headspace of a desired gas.

Many liposomal preparatory techniques which may be adapted for use in the preparation of vesicle compositions are discussed, for example, in U.S. Pat. No. 4,728,578; U.K. Patent Application. GB 2193095 A; U.S. Pat. No. 4,728,575; U.S. Pat. No. 4,737,323; International Application Serial No. PCT/US85/01161; Mayer et al., *Biochimica et Biophysica Acta*, Vol. 858, pp. 161–168 (1986); Hope et al., *Biochimica et Biophysica Acta*, Vol. 812, pp. 55–65 (1985); U.S. Pat. No. 4,533,254; Mayhew et al., *Methods in Enzymology*, Vol. 149, pp. 64–77 (1987); Mayhew et al., *Biochimica et Biophysica Acta*, Vol 755, pp. 169–74 (1984); Cheng et al, *Investigative Radiology*, Vol. 22, pp. 47–55 (1987); International Application Serial No. PCT/US89/05040; U.S. Pat. No. 4,162,282; U.S. Pat. No. 4,310,505; U.S. Pat. No. 4,921,706; and *Liposome Technology*, Gregoriadis, G., ed., Vol. I, pp. 29–31, 51–67 and 79–108 (CRC Press Inc., Boca Raton, Fla. 1984), the disclosures of each of which are hereby incorporated by reference herein, in their entirety.

Silicon amphiphilic compositions comprising a gas can be prepared by agitating an aqueous solution containing, if desired, an additional stabilizing material, in the presence of a gas. The term "agitating," as used herein, means any shaking, mixing or other motion of an aqueous solution such that gas is introduced from the local ambient environment into the aqueous solution. This agitation is preferably conducted at a temperature below the gel to liquid crystalline phase transition temperature of any additional lipids which may be present, and, depending on the particular silicon amphiphilic compound or compounds employed, may also be conducted at a temperature below the gel to liquid crystalline phase transition temperature of the silicon amphiphilic compound(s). The agitation of the solutions is preferably of sufficient force to result in the formation of a silicon amphiphilic composition, preferably a vesicle composition, and particularly vesicle compositions comprising gas filled vesicles. The agitation may be by swirling, such as by vortexing, side-to-side, up and down or mixing motion. Different types of motion may be combined. Also, the agitation may occur by shaking the container holding the aqueous silicon amphiphilic solution, or by shaking the aqueous solution within the container without shaking the container itself.

The agitation may occur manually or by machine. Mechanical shakers that may be used include, for example, a shaker table such as a VWR Scientific (Cerritos, Calif.) shaker table, as well as any of the shaking devices described hereinbefore, with the Capmix (Espe Fabrik Pharmazeutischer Praeparate GMBH & Co., Seefeld, Oberay Germany)

being preferred. It has been found that certain modes of shaking or vortexing can be used to make vesicles within a preferred size range. Shaking is preferred, and it is preferred that the shaking be carried out using the Espe Capmix mechanical shaker. In accordance with this preferred method, it is preferred that a reciprocating motion be utilized to generate the silicon amphiphilic compositions, and particularly vesicle compositions. It is even more preferred that the motion be reciprocating in the form of an arc. It is contemplated that the rate of reciprocation, as well as the arc thereof, is particularly important in connection with the formation of vesicles. Preferably, the number of reciprocations or full cycle oscillations is from about 1000 to about 20,000 per minute. More preferably, the number of reciprocations or oscillations is from about 2500 to about 8000, with reciprocations or oscillations of from about 3300 to about 5000 being even more preferred. Of course, the number of oscillations can be dependent upon the mass of the contents being agitated. Generally speaking, a larger mass requires fewer. oscillations. Another means for producing agitation includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing at about 60 to about 300 revolutions per minute is more preferred. Vortexing at about 300 to about 1800 revolutions per minute is even more preferred.

In addition to the simple agitation methods described above, more elaborate methods can also be employed. Such elaborate methods include, for example, liquid crystalline shaking gas instillation processes and vacuum drying gas instillation processes, such as those described in copending U.S. application Serial No. 08/076,250, filed Jun. 11, 1993, the disclosures of which are incorporated herein by reference, in their entirety. Although any of a number of varying techniques can be used, the vesicle compositions employed in the present invention are preferably prepared using a shaking technique. Preferably, the shaking technique involves agitation with a mechanical shaking apparatus, such as an Espe Capmix (Seefeld, Oberay Germany), using, for example, the techniques disclosed in copending U.S. application Ser. No. 160,232, filed Nov. 30, 1993, the disclosures of which are hereby incorporated herein by reference in their entirety.

The size of gas filled vesicles can be adjusted, if desired, by a variety of procedures, including, for example, microemulsification, vortexing, extrusion, filtration, sonication, homogenization, repeated freezing and thawing cycles, extrusion under pressure through pores of defined size, and similar methods. Gas filled vesicles prepared in accordance with the methods described herein can range in size from less than about 1 $\mu$m to greater than about 100 $\mu$m. In addition, after extrusion and sterilization procedures, which are discussed in detail below, agitation or shaking provides vesicle compositions which provide substantially no or minimal residual anhydrous lipid phase in the remainder of the solution. (Bangham, A. D., Standish, M. M, & Watkins, J. C., *J. Mol. Biol.* Vol. 13, pp. 238–252 (1965). If desired, the vesicles of the present invention may be used as they are formed, without any attempt at further modification of the size thereof. For intravascular use, the vesicles preferably have diameters of less than about 30 $\mu$m, and more preferably, less than about 12 $\mu$m. For targeted intravascular use including, for example, binding to certain tissue, such as cancerous tissue, the vesicles can be significantly smaller, for example, less than about 100 nm in diameter. For enteric or gastrointestinal use, the vesicles can be significantly larger, for example, up to a millimeter in size. Preferably, the vesicles are sized to have diameters of from about 2 $\mu$m to about 100 $\mu$m.

The gas filled vesicles may be sized by a simple process of extrusion through filters wherein the filter pore sizes control the size distribution of the resulting gas filled vesicles. By using two or more cascaded or stacked set of filters, for example, a 10 $\mu$m filter followed by an 8 $\mu$m filter, the gas filled vesicles can be selected to have a very narrow size distribution around 7 to 9 $\mu$m. After filtration, these gas filled vesicles can remain stable for over 24 hours.

The sizing or filtration step may be accomplished by the use, for example, of a filter assembly when the composition is removed from a sterile vial prior to use, or more preferably, the filter assembly may be incorporated into a syringe during use. The method of sizing the vesicles will then comprise using a syringe comprising a barrel, at least one filter, and a needle; and will be carried out by a step of extracting which comprises extruding the vesicles from the barrel through the filter fitted to the syringe between the barrel and the needle, thereby sizing the vesicles before they are administered to a patient. The step of extracting may also comprise drawing the vesicles into the syringe, where the filter will function in the same way to size the vesicles upon entrance into the syringe. Another alternative is to fill such a syringe with vesicles which have already been sized by some other means, in which case the filter now functions to ensure that only vesicles within the desired size range, or of the desired maximum size, are subsequently administered by extrusion from the syringe.

In certain preferred embodiments, the vesicle compositions may be heat sterilized or filter sterilized and extruded through a filter prior to shaking. Generally speaking, vesicle compositions comprising a gas may be heat sterilized, and vesicle compositions comprising gaseous precursors may be filter sterilized. Once gas filled vesicles are formed, they may be filtered for sizing as described above. Performing these steps prior to the formation of gas and gaseous precursor filled vesicles provide sterile gas filled vesicles ready for administration to a patient. For example, a mixing vessel such as a vial or syringe may be filled with a filtered lipid composition, and the composition may be sterilized within the mixing vessel, for example, by autoclaving. Gas may be instilled into the composition to form gas filled vesicles by shaking the sterile vessel. Preferably, the sterile vessel is equipped with a filter positioned such that the gas filled vesicles pass through the filter before contacting a patient.

The step of extruding the solution of silicon amphiphilic compound through a filter decreases the amount of unhydrated material by breaking up any dried materials and exposing a greater surface area for hydration. Preferably, the filter has a pore size of about 0.1 to about 5 $\mu$m, more preferably, about 0.1 to about 4 $\mu$m, even more preferably, about 0.1 to about 2 $\mu$m, and still more preferably, about 1 $\mu$m. Unhydrated compound, which is generally undesirable, may appear as amorphous clumps of non-uniform size.

The sterilization step provides a composition. that may be readily administered to a patient for diagnostic imaging including, for example, ultrasound or CT. In certain preferred embodiments, sterilization may be accomplished by heat sterilization, preferably, by autoclaving the solution at a temperature of at least about 100° C., and more preferably, by autoclaving at about 100° C. to about 130° C., even more preferably, about 110° C. to about 130° C., still more preferably, about 120° C. to about 130° C., and even more preferably, about 130° C. Preferably, heating occurs for at least about 1 minute, more preferably, about 1 to about 30 minutes, even more preferably, about 10 to about 20 minutes, and still more preferably, about 15 minutes.

If desired, the extrusion and heating steps, as outlined above, may be reversed, or only one of the two steps can be used. Other modes of sterilization may be used, including, for example, exposure to gamma radiation.

In addition to the aforementioned embodiments, gaseous precursors contained in vesicles can be formulated which, upon activation, for example, by exposure to elevated temperature, varying pH, or light, undergo a phase transition from, for example, a liquid, including a liquid entrapped in a vesicle, to a gas, expanding to create the gas filled vesicles described herein. This technique is described in detail in copending patent applications Ser. Nos. 08/160,232, filed Nov. 30, 1993 and 08/159,687, filed Nov. 30, 1993, the disclosures of which are incorporated herein by reference, in their entirety.

The preferred method of activating the gaseous precursor is by exposure to elevated temperature. Activation or transition temperature, and like terms, refer to the boiling point of the gaseous precursor and is the temperature at which the liquid to gaseous phase transition of the gaseous precursor takes place. Useful gaseous precursors are those materials which have boiling points in the range of about −100° C. to about 70° C. The activation temperature is particular to each gaseous precursor. An activation temperature of about 37° C., or about human body temperature, is preferred for gaseous precursors in the context of the present invention. Thus, in preferred form, a liquid gaseous precursor is activated to become a gas at about 37° C. or below. The gaseous precursor may be in liquid or gaseous phase for use in the methods of the present invention.

The methods of preparing the gaseous precursor filled vesicles may be carried out below the boiling point of the gaseous precursor such that a liquid is incorporated, for example, into a vesicle. In addition, the methods may be conducted at the boiling point of the gaseous precursor, such that a gas is incorporated, for example, into a vesicle. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature-activated gaseous precursor filled vesicles may be carried out at a temperature below the boiling point of the gaseous precursor. In this embodiment, the gaseous precursor is entrapped within a vesicle such that the phase transition does not occur during manufacture. Instead, the gaseous precursor filled vesicles are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the vesicles upon attaining the gaseous state may be determined.

Alternatively, the gaseous precursors may be utilized to create stable gas filled vesicles which are pre-formed prior to use. In this embodiment, the gaseous precursor is added to a container housing a silicon amphiphilic composition at a temperature below the liquid-gaseous phase transition temperature of the respective gaseous precursor. As the temperature is increased, and an emulsion is formed between the gaseous precursor and liquid solution, the gaseous precursor undergoes transition from the liquid to the gaseous state. As a result of this heating and gas formation, the gas displaces the air in the head space above the liquid mixture so as to form gas filled vesicles which entrap the gas of the gaseous precursor, ambient gas (e.g. air), or coentrap gas state gaseous precursor and ambient air. This phase transition can be used for optimal mixing and formation of the contrast agent. For example, the gaseous precursor, perfluorobutane, can be entrapped in the lipid vesicles and as the temperature is raised beyond the boiling point of perfluorobutane (4° C.), perfluorobutane gas is entrapped in the vesicles.

Accordingly, the gaseous precursors may be selected to form gas filled vesicles in vivo or may be designed to produce the gas filled vesicles in situ, during the manufacturing process, on storage, or at some time prior to use. A water bath, sonicator or hydrodynamic activation by pulling back the plunger of a syringe against a closed stopcock may be used to activate targeted gas-filled vesicles from temperature-sensitive gaseous precursors prior to IV injection.

As a further embodiment of this invention, by preforming the gaseous precursor in the liquid state into an aqueous emulsion, the maximum size of the vesicle may be estimated by using the ideal gas law, once the transition to the gaseous state is effectuated. For the purpose of making gas filled vesicles from gaseous precursors, the gas phase is assumed to form instantaneously and substantially no gas in the newly formed vesicle has been depleted due to diffusion into the liquid, which is generally aqueous in nature. Hence, from a known liquid volume in the emulsion, one would be able to predict an upper limit to the size of the gas filled vesicle.

In embodiments of the present invention, a mixture of a silicon amphiphilic compound, optional additional stabilizing materials, and a gaseous precursor, containing liquid droplets of defined size, may be formulated such that upon reaching a specific temperature, for example, the boiling point of the gaseous precursor, the droplets will expand into gas filled vesicles of defined size. The defined size represents an upper limit to the actual size because the ideal gas law cannot account for such factors as gas diffusion into solution, loss of gas to the atmosphere, and the effects of increased pressure.

The ideal gas law, which can be used for calculating the increase in the volume of the gas bubbles upon transitioning from liquid to gaseous states, is as follows:

$$PV=nRT$$

where

P is pressure in atmospheres (atm);

V is volume in liters (L);

n is moles of gas;

T is temperature in degrees Kelvin (K); and

R is the ideal gas constant (22.4 L-atm/K-mole).

With knowledge of volume, density, and temperature of the liquid in the mixture of liquids, the amount, for example, in moles, and volume of liquid precursor may be calculated which, when converted to a gas, will expand into a vesicle of known volume. The calculated volume will reflect an upper limit to the size of the gas filled vesicle, assuming instantaneous expansion into a gas filled vesicle.and negligible diffusion of the gas over the time of the expansion. .

Thus, for stabilization of the precursor in the liquid state in a mixture wherein the precursor droplet is spherical, the volume of the precursor droplet may be determined by the equation:

$$\text{Volume (spherical. vesicle)}=4/3\pi r^3$$

where r is the radius of the sphere.

Thus, once the volume is predicted, and knowing the density of the liquid at the desired temperature, the amount of liquid gaseous precursor in the droplet may be determined. In more descriptive terms, the following can be applied:

$$V_{gas}=4/3\pi(r_{gas})^3$$

by the ideal gas law, $$PV=nRT$$

substituting reveals, $$V_{gas}=nRT/P_{gas}$$

or, $$n=4/3[\pi r_{gas}^3]P/RT \quad (A)$$

amount $n=4/3[\pi r_{gas}^3 P/RT] \cdot MW_n$

Converting back to a liquid volume $$V_{liq}=[4/3[\pi r_{gas}^3]P/RT] \cdot MW_n/D] \quad (B)$$

where D is the density of the precursor.

Solving for the diameter of the liquid droplet, $$\text{diameter}/2=[\tfrac{3}{4}\pi[4/3 \cdot [\pi r_{gas}^3]P/RT]MW_n/D]^{1/3} \quad (C)$$

which reduces to $$\text{Diameter}=2[[r_{gas}^3]P/RT[MW_n/D]]^{1/3}.$$

As a further means of preparing vesicles of the desired size for use in the methods of the present invention, and with a knowledge of the volume and especially the radius of the liquid droplets, one can use appropriately sized filters to size the gaseous precursor droplets to the appropriate diameter sphere.

A representative gaseous precursor may be used to form a vesicle of defmed size, for example, 10 $\mu$m diameter. In this example, the vesicle is formed in the bloodstream of a human being, thus the typical temperature would be 37° C. or 310 K. At a pressure of 1 atmosphere and using the equation in (A), $7.54\times10^{-17}$ moles of gaseous precursor would be required to fill the volume of a 10 $\mu$m diameter vesicle.

Using the above calculated amount of gaseous precursor and 1-fluorobutane, which possesses a molecular weight of 76.11, a boiling point of 32.5° C. and a density of 0.7789 g/mL at 20° C., further calculations predict that $5.74\times10^{-15}$ grams of this precursor would be required for a 10 $\mu$m vesicle. Extrapolating further, and with the knowledge of the density, equation (B) further predicts that $8.47\times10^{-16}$ mL of gaseous precursor is necessary to form a vesicle with an upper limit of 10 $\mu$m.

Finally, using equation (C), a mixture, for example, an emulsion containing droplets with a radius of 0.0272 $\mu$m or a corresponding diameter of 0.0544 $\mu$m, is formed to make a gaseous precursor filled vesicle with an upper limit of a 10 $\mu$m vesicle.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment for preparing gas filled vesicles may be applied to all gaseous precursors activated by temperature. In fact, depression of the freezing point of the solvent system allows the use of gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers, the freezing point is lowered by an amount that is dependent upon the composition of the solution. Thus, as defined by Wall, one can express the freezing point depression of the solvent by the following equation:

$$\text{In}x_a=\text{In }(1-x_b)=\Delta H_{fus}R(1/T_o-1/T)$$

where $x_a$ is the mole fraction of the solvent;

$x_b$ is the mole fraction of the solute;

$\Delta H_{fus}$ is the heat of fusion of the solvent; and $T_o$ is the normal freezing point of the solvent.

The normal freezing point of the solvent can be obtained by solving the equation. If $X_b$ is small relative to xa, then the above equation may be rewritten as follows.

$$x^b=\Delta H_{fus}/R[T-T_o/T_oT]\approx\Delta H_{fus}\Delta T/RT_o{}^2$$

The above equation assumes the change in temperature $\Delta T$ is small compared to $T_2$. This equation can be simplified further by expressing the concentration of the solute in terms of molality, m (moles of solute per thousand grams of solvent). Thus, the equation can be rewritten as follows.

$$X_b=m/[m+1000/m_a]\approx mMa/1000$$

where Ma is the molecular weight of the solvent.

Thus, substituting for the fraction $x_b$:

$$\Delta T=[M_aRT_o{}^2/1000\Delta H_{fus}]m$$

or $$\Delta T=K_fm, \text{ where}$$

$$K_f=M_aRT_o{}^2/1000\Delta H_{fus}$$

$K_f$ is the molal freezing point and is equal to 1.86 degrees per unit of molal concentration for water at one atmosphere pressure. The above equation may be used to accurately determine the molal freezing point of solutions of gaseous-precursor filled vesicles. Accordingly, the above equation can be applied to estimate freezing point depressions and to determine the appropriate concentrations of liquid or solid solute necessary to depress the solvent freezing temperature to an appropriate value.

Methods of preparing the temperature activated gaseous precursor filled vesicles include:

(a) vortexing and/or shaking an aqueous mixture of gaseous precursor and additional materials as desired, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor filled vesicle to form spontaneously and cooling down the suspension of gaseous precursor filled vesicles; and extruding an aqueous suspension of gaseous precursor through a filter of about 0.22 μm. Alternatively, filtering may be performed during in vivo administration of the vesicles such that a filter of about 0.22 μm is employed;

(b) microemulsification whereby an aqueous mixture of gaseous precursor is emulsified by agitation and heated to form, for example, vesicles prior to administration to a patient;

(c) heating a gaseous precursor in a mixture, with or without agitation, whereby the less dense gaseous precursor filled vesicles float to the top of the solution by expanding and displacing other vesicles in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor vesicle to form spontaneously, whereby the expanded gaseous precursor in the sealed vessel increases the pressure in the vessel, and cooling down the gas filled vesicle suspension, after which shaking may also take place.

Freeze drying is useful to remove water and organic materials prior to the shaking installation method. Drying installation methods may be used to remove water from vesicles. By pre-entrapping the gaseous precursor in the dried vesicles (i.e. prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state. For example, perfluorobutane can be used to fill dried vesicles at temperatures above 4° C. (the boiling point of perfluorobutane).

Preferred methods for preparing the temperature activated gaseous precursor filled vesicles comprise shaking an aqueous solution of the silicon amphiphilic compound and optional additional stabilizing materials, in the presence of a gaseous precursor, at a temperature which is below the liquid state to gas state phase transition temperature of the gaseous precursor. This may also be conducted, depending on the materials employed in the compositions, at a temperature below the gel state to liquid crystalline state phase transition temperature of the silicon amphiphilic compound and optional lipid. The mixture is then heated to a temperature above the liquid state to gas state phase transition temperature of the gaseous precursor which causes the precursor to volatilize and expand. Heating is then discontinued, and the temperature of the mixture is then allowed to drop below the liquid state to gas state phase transition temperature of the gaseous precursor. Shaking of the mixture may take place during the heating step, or subsequently after the mixture is allowed to cool.

Other methods for preparing gaseous precursor filled vesicles can involve shaking an aqueous solution of, for example, a silicon amphiphilic compound and a gaseous precursor, and separating the resulting gaseous precursor filled vesicles.

Conventional, aqueous-filled liposomes of the prior art are routinely formed at a temperature above the phase transition temperature of the lipids used to make them, since they are more flexible and thus useful in biological systems in the liquid crystalline state. See, e.g., Szoka and Papahadjopoulos, *Proc. Natl. Acad. Sci.* 1978, 75, 4194–4198, the disclosures of which are incorporated herein by reference, in their entirety. In contrast, the vesicles made according to certain preferred embodiments described herein are gaseous precursor filled, which imparts greater flexibility, since gaseous precursors after gas formation are more compressible and compliant than an aqueous solution.

The methods contemplated by the present invention provide for agitating an aqueous solution comprising a silicon amphiphilic compound and optional additional stabilizing materials, in the presence of a temperature activatable gaseous precursor. Preferably, the agitation is of sufficient force such that a foam may be formed within a short period of time, such as about 30 minutes, and preferably within about 20 minutes, and more preferably, within about 10 minutes. The agitation may involve shaking, microemulsifying, microfluidizing, swirling (such as by vortexing), mixing, homogenization, side-to-side, or up and down motion. In the case of the addition of gaseous precursor in the liquid state, sonication may be used in addition to the agitation methods set forth above. Further, different types of motion may be combined. Also, the agitation may occur by shaking the container holding the aqueous solution, or by shaking the aqueous solution within the container without shaking the container itself. Further, the agitation may occur manually or by machine. Mechanical shakers that may be used include, for example, the mechanical shakers described hereinbefore, with an Espe Capmix (Seefeld, Oberay Germany) being preferred. Another means for producing agitation includes the action of gaseous precursor emitted under high velocity or pressure.

According to the methods described herein, a gas, such as air, may also be provided by the local ambient atmosphere. The local ambient atmosphere can include the atmosphere within a sealed container, as well as the external environment. Alternatively, for example, a gas may be injected into or otherwise added to the container having the aqueous solution or into the aqueous solution itself to provide a gas other than air. Gases that are lighter than air are generally added to a sealed container, while gases heavier than air can be added to a sealed or an unsealed container. Accordingly, the present invention includes co-entrapment of air and/or other gases along with gaseous precursors.

Hence, the gaseous precursor filled vesicles can be used in substantially the same manner as the gas filled vesicles described herein, once activated by application to the tissues of a host, where such factors as temperature or pH may be used to cause generation of the gas. It is preferred that the gaseous precursors undergo phase transitions from liquid to gaseous states at near the normal body temperature of the host, and are thereby activated, for example, by the in vivo temperature of the host so as to undergo transition to the gaseous phase therein. Alternating, activation prior to IV injection may be used, for example, by thermal, mechanical or optical means. This activation can occur where, for example, the host tissue is human tissue having a normal temperature of about 37° C. and the gaseous precursors undergo phase transitions from liquid to gaseous states near 37° C.

As noted above, the silicon amphiphilic compositions may be sterilized by autoclave or sterile filtration if these processes are performed before the installation step or prior to temperature mediated conversion of the temperature sensitive gaseous precursors within the compositions. Alternatively, one or more anti-bactericidal agents and/or preservatives may be included in the formulation of the compositions, such as sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized vesicles are used for imaging under invasive circumstances, e.g., intravascularly or intraperitonealy. The appropriate means of sterilization will be apparent to the artisan based on the present disclosure.

As with the preparation of silicon amphiphilic compositions, a wide variety of techniques are available for the preparation of silicon amphiphilic formulations. For example, the silicon amphiphilic formulations may be prepared from a mixture of silicon amphiphilic compounds, optional additional stabilizing materials, bioactive agent and gas or gaseous precursor. In this case, silicon amphiphilic compositions are prepared as described above in which the compositions also comprise bioactive agent. Thus, for example, micelles can be prepared in the presence of a bioactive agent. In connection with silicon amphiphilic compositions which comprise a gas, the preparation can involve, for example, bubbling a gas directly into a mixture of the silicon amphiphilic compounds and one or more optional additional materials. Alternatively, the silicon amphiphilic compositions may be preformed from silicon amphiphilic compounds and gas or gaseous precursor. In the latter case, the bioactive agent is then added to the silicon amphiphilic composition prior to use. For example, an aqueous mixture of liposomes and gas may be prepared to which the bioactive agent is added and which is agitated to provide the liposome formulation. The liposome formulation can be readily isolated since the gas and/or bioactive agent filled liposome vesicles generally float to the top of the aqueous solution. Excess bioactive agent can be recovered from the remaining aqueous solution.

As those skilled in the art will recognize, any of the silicon amphiphilic compositions and/or silicon amphiphilic formulations may be lyophilized for storage, and reconstituted, for example, with an aqueous medium (such as sterile water, phosphate buffered solution, or aqueous saline solution), with the aid of vigorous agitation. To prevent agglutination or fusion of the silicon amphiphilic compound, lipids and/or vesicles as a result of lyophilization, it may be useful to include additives which prevent such fusion or agglutination from occurring. Additives which may be useful include sorbitol, mannitol, sodium chloride, glucose, trehalose, polyvinylpyrrolidone and poly(ethylene glycol) (PEG), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life.

As discussed above, the compositions of the present invention, including gas and/or gaseous precursor filled vesicles, are useful as contrast agents for diagnostic imaging, including, for example, ultrasound imaging (US), computed tomography (CT) imaging, including CT angiography (CTA) imaging, magnetic resonance (MR) imaging, including magnetic resonance angiography (MRA), nuclear medicine, optical imaging and elastography.

In accordance with the present invention, there are provided methods of imaging one or more regions of a patient. The present invention also provides methods for diagnosing the presence or absence of diseased tissue in a patient. The methods of. the present invention involve the administration of a contrast medium, preferably in the form of a silicon amphiphilic composition, to a patient. The patient is scanned using diagnostic imaging including, for example ultrasound imaging, to obtain visible images of an internal region of a patient. The methods are especially useful in providing images of the heart region and the gastrointestinal region or the lymphatic system, but can also be employed more broadly to image other internal regions of the patient including, for example, the vasculature. The phrase "gastrointestinal region" or "gastrointestinal tract," as used herein, includes the region of a patient defined by the esophagus, stomach, small and large intestines and rectum. The present methods can also be used in connection with the delivery of a bioactive agent to an internal region of a patient.

If desired, the lipid and/or vesicle compositions described herein may further comprise a targeting agent to promote targeting of tissues and/or receptors in vivo including, for example, myocardial tissue. Suitable targeting agents, methods for their incorporation into lipid and/or vesicle compositions, and methods for the use of such targeted compositions, are described, for example, in copending U.S. application Ser. No. 08/640,464, filed May 1, 1996 and copending U.S. application Ser. No. 08/660,032, filed Jun. 6, 1996, the disclosures of which are hereby incorporated herein by reference, in their entirety.

As one skilled in the art would recognize, once placed in possession of the present disclosure, administration of the silicon amphiphilic compositions described herein may be carried out in various fashions, namely, parenterally, orally, or intraperitoneally. Parenteral administration, which is preferred, includes administration by the following routes: intravenous; intramuscular; interstitially; intra-arterially; subcutaneous; intraocular; intrasynovial; transepithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration. The useful dosage to be administered and the particular mode of administration will vary depending upon the age, weight and the particular mammal and region thereof to be scanned, and the particular composition employed. Typically, dosage is initiated at lower levels and increased until the desired contrast enhancement is achieved. Various combinations of the silicon amphiphilic compositions may be used to alter properties as desired, including viscosity, osmolarity or palatability. In carrying out the imaging methods of the present invention, the contrast medium can be used alone, or in combination with diagnostic, therapeutic or other agents. Such other agents include excipients such as flavoring or coloring materials. CT imaging techniques which are employed are conventional and are described, for example, in *Computed Body Tomography*, Lee, J. K. T., Sagel, S. S., and Stanley, R. J., eds., 1983, Ravens Press, New York, N.Y., especially the first two chapters thereof entitled *"Physical Principles and Instrumentation"*, Ter-Pogossian, M. M., and *"Techniques"*,. Aronberg, D. J., the disclosures of which are incorporated by reference herein in their entirety.

In the case of diagnostic applications, such as ultrasound and CT, energy, such as ultrasonic energy, is applied to at least a portion of the patient to image the target tissue. A visible image of an internal region of the patient is then obtained, such that the presence or absence of diseased tissue can be ascertained. With respect to ultrasound, ultrasonic imaging techniques, including second harmonic imaging, and gated imaging, are well known in the art, and are described, for example, in Uhlendorf, "Physics of Ultrasound Contrast Imaging: Scattering in the Linear Range", *IEEE Transactions on Ultrasonics, Ferroelectrics, and Frequency Control*, Vol. 14(1), pp. 70–79 (1994) and Sutherland, et al., "Color Doppler Myocardial Imaging: A New Technique for the Assessment of Myocardial Function", *Journal of the American Society of Echocardiography*, Vol. 7(5), pp. 441–458 (1994), the disclosures of which are hereby incorporated herein by reference in their entirety.

Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Thus, diagnostic ultrasound generally involves the application of a pulse of echoes, after which, during a listening period, the ultrasound transducer receives reflected signals. Harmonics, ultraharmonics or subharmonics may be used. The second harmonic mode may be beneficially employed, in which the 2x frequency is received, where x is the incidental frequency. This may serve to decrease the signal from the background material and enhance the signal from the transducer using the contrast media of the present invention. Other harmonics signals, such as odd harmonics signals, for example, 3x or 5x, would be similarly received using this method. Subharmonic signals, for example, x/2 and x/3, may also be received and processed so as to form an image.

In addition to the pulsed method, continuous wave ultrasound, for example, Power Doppler, may be applied. In this case, the relatively higher energy of the Power Doppler may be made to resonate the vesicles and thereby promote their rupture. This can create acoustic emissions which may be in the subharmonic or ultraharmonic range or, in some cases, in the same frequency as the applied ultrasound. It is contemplated that there will be a spectrum of acoustic signatures released in this process and the transducer so employed may receive the acoustic emissions to detect, for example, the presence of a clot. In addition, the process of vesicle rupture may be employed to transfer kinetic energy to the surface, for example of a clot to promote clot lysis. Thus, therapeutic thrombolysis may be achieved during a combination of diagnostic and therapeutic ultrasound. Spectral Doppler may also be employed. In general, the levels of energy from diagnostic ultrasound are insufficient to promote the rupture of vesicles and to facilitate release and cellular uptake of the bioactive agents. As noted above, diagnostic ultrasound may involve the application of one or more pulses of sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle species. In general, devices for therapeutic ultrasound employ from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may be pulsed also. If pulsed sound energy is used, the sound will generally be pulsed in echo train lengths of from about 8 to about 20 or more pulses at a time. Preferably, the echo train lengths are about 20 pulses at a time. In addition, the frequency of the sound used may vary from about 0.025 to about 100 megahertz (MHZ). In general, frequency for therapeutic ultrasound preferably ranges between about 0.75 and about 3 MHZ, with from about 1 and about 2 MHZ being more preferred. In addition, energy levels may vary from about 0.5 Watt (W) per square' centimeter ($cm^2$) to about 5.0 $W/cm^2$, with energy levels of from about 0.5 to about 2.5 $W/cm^2$ being preferred. Energy levels for therapeutic ultrasound involving hyperthermia are generally from about 5 $W/cm^2$ to about 50 $W/cm^2$. For very small vesicles, for example, vesicles having a diameter of less than about 0.5 $\mu$m, higher frequencies of sound are generally preferred. This is because smaller vesicles are capable of absorbing sonic energy more effectively at higher frequencies of sound. When very high frequencies are used, for example, greater than about 10 MHZ, the sonic energy will generally penetrate fluids and tissues to a limited depth only. Thus, external application of the sonic energy may be suitable for skin and other superficial tissues. However, it is generally necessary for deep structures to focus the ultrasonic energy so that it is preferentially directed within a focal zone. Alternatively, the ultrasonic energy may be applied via interstitial probes, intravascular ultrasound catheters or endoluminal catheters. Such probes or catheters may be used, for example, in the esophagus for the diagnosis and/or treatment of esophageal carcinoma. In addition to the therapeutic uses discussed above, the present compositions can be employed in connection with esophageal carcinoma or in the coronary arteries for the treatment of atherosclerosis, as well as the therapeutic uses described, for example, in U.S. Pat. No. 5,149,319, the disclosures of which are hereby incorporated herein by reference, in their entirety.

A therapeutic ultrasound device may be used which employs two frequencies of ultrasound. The first frequency may be x, and the second frequency may be 2x. In preferred form, the device would be designed such that the focal zones of the first and second frequencies converge to a single focal zone. The focal zone of the device may then be directed to the targeted compositions, for example, targeted vesicle compositions, within the targeted tissue. This ultrasound device may provide second harmonic therapy with simultaneous application of the x and 2x frequencies of ultrasound energy. It is contemplated that, in the case of ultrasound involving vesicles, this second harmonic therapy may provide improved rupturing of vesicles as compared to ultrasound energy involving a single frequency. Also, it is contemplated that the preferred frequency range may reside within the fundamental harmonic frequencies of the vesicles. Lower energy may also be used with this device. An ultrasound device which may be employed in connection with the aforementioned second harmonic therapy is described, for example, in Kawabata, K. et al., *Ultrasonics Sonochemistry*, Vol. 3, pp. 1–5 (1996), the disclosures of which are hereby incorporated herein by reference, in their entirety.

The concentration of silicon amphiphilic compound and optional stabilizing materials, including lipids, employed in a silicon amphiphilic composition and/or to form stabilized vesicles may vary and depends, for example, upon the particular silicon amphiphilic compound and. optional stabilizing material used. Suitable concentrations may be readily determined by one skilled in the art through routine experimentation. In preferred embodiments, the concentration of silicon amphiphilic compound may range from about 0.1 mg/mL to about 30 mg/mL of saline solution, and all combinations and subcombinations of ranges therein. Preferably, the concentration of silicon amphiphilic compound may range from about 0.5 mg/mL to about 20 mg/mL, with concentrations of from about 1 mg/mL to about 10 mg/mL being preferred. DPPC may optionally be employed in a concentration which ranges from about 0.1 mg/mL to about 30 mg/mL of saline solution, and all combinations and subcombinations of ranges therein. More preferably, DPPC may be employed in a concentration of from about 1 mg/mL to about 25 mg/mL of saline solution, and even more preferably from about 5 mg/mL to about 20 mg/mL of saline solution. DPPA may also be employed in the present compositions in a concentration which ranges from about 0.1 mg/mL to about 30 mg/mL of saline solution, and all combinations and subcombinations of ranges therein. More preferably, DPPA may be be employed in a concentration of from about 0.5 mg/mL to about 20 mg/mL of saline solution, and even more preferably, from about 1 mg/mL to about 10 mg/mL of saline solution. The concentration of distearoylphosphatidylcholine (DSPC) which may be used in preferred embodiments is about 0.1 mg/mL to about 30 mg/mL of saline solution, more preferably from about 0.5 mg/mL to about 20 mg/mL of saline solution, and most preferably from about 1 mg/mL to about 10 mg/mL of saline solution. The amount of composition which is administered to a patient can vary. Typically, the IV dose may be less than about 10 mL for a 70 Kg patient, with lower doses being preferred.

The gaseous precursors may be utilized to create stable gas filled vesicles which are pre-formed prior to use. In this embodiment, the gaseous precursor may be added to a container containing a medium which comprises a silicon amphiphilic compound and optional stabilizing materials at a temperature below the liquid-gaseous phase transition temperature of the respective gaseous precursor. As the temperature is increased, and the liquid-gaseous phase transition temperature exceeded, an emulsion typically forms between the gaseous precursor and liquid solution as the gaseous precursor undergoes transition from the liquid to the gaseous state. As a result of this heating and gas formation, the gas displaces the air in the head space above the liquid suspension so as to form gas filled vesicles which entrap the gas of the gaseous precursor, ambient gas for example, air, or coentrap gas state gaseous precursor and ambient air. This phase transition can be used for optimal mixing and stabilization of the contrast medium. For example, the gaseous precursor, perfluorobutane, can be entrapped in a vesicle of the silicon amphiphilic compound and optional stabilizing materials, and as the temperature is raised beyond about 4° C., which is boiling point of perfluorobutane, vesicles are provided which contain entrapped fluorobutane gas. As an additional example, the gaseous precursor fluorobutane can be suspended in an aqueous suspension containing silicon amphiphilic compound and emulsifying and stabilizing agents, such as glycerol or propylene glycol, and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, surprisingly stable gas filled vesicles result.

Accordingly, the gaseous precursors may be selected to form a gas filled vesicle in vivo or may be designed to produce the gas filled vesicle in situ, during the manufacturing process, on storage, or at some time prior to use.

It will be understood by one skilled in the art, once armed with the present disclosure, that the silicon amphiphilic compound, and other stabilizing compounds used as starting materials, or the vesicle final products, may be manipulated prior and subsequent to being subjected to the methods contemplated by the present invention. For example, the silicon amphiphilic compound and stabilizing compound such as a biocompatible lipid may be hydrated and then lyophilized, processed through freeze and thaw cycles, or simply hydrated. In preferred embodiments, the silicon amphiphilic compound is hydrated and then lyophilized, or hydrated, then processed through freeze and thaw cycles and then lyophilized, prior to the formation of gaseous precursor filled vesicles.

According to the methods contemplated by the present invention, the presence of gas, such as and not limited to air, may also be provided by the local ambient atmosphere. The local ambient atmosphere may be the atmosphere within a sealed container, or in an unsealed container, may be the external environment. Alternatively, for example, a gas may be injected into or otherwise added to the container having the aqueous solution or into the aqueous solution itself in order to provide a gas other than air. Gases that are not heavier than air may be added to a sealed container while gases heavier than air may be added to a sealed or an unsealed container. Accordingly, the present invention includes co-entrapment of air and/or other gases along with gaseous precursors.

As already described above in the section dealing with the stabilizing compound, the methods contemplated by the present invention may be carried out, depending, for example, on the particular materials employed in the compositions, at a temperature which is below the gel state to liquid crystalline state phase transition temperature of the silicon amphiphilic compound and/or optional lipids employed. The phrase "gel state to liquid crystalline state phase transition temperature" means the temperature at which a lipid bilayer will convert from a gel state to a liquid crystalline state. See, e.g., Chapman et al., *J. Biol. Chem.* 1974, 249, 2512–2521.

Hence, the stabilized vesicle precursors described above, can be used in the same manner as the other stabilized vesicles used in the present invention, once activated by application to the tissues of a host, where such factors as temperature or pH may be used to cause generation of the gas. It is preferred that this embodiment is one wherein the gaseous precursors undergo phase transitions from liquid to gaseous states at near the normal body temperature of the host, and are thereby activated by the temperature of the host tissues so as to undergo transition to the gaseous phase therein. More preferably still, this method is one wherein the host tissue is human tissue having a normal temperature of about 37° C., and wherein the gaseous precursors undergo phase transitions from liquid to gaseous states near 37° C.

All of the above embodiments involving preparations of the stabilized gas filled vesicles used in the present invention, may be sterilized by autoclave or sterile filtration if these processes are performed before either the gas instillation step or prior to temperature mediated gas conversion of the temperature sensitive gaseous precursors within the suspension. Alternatively, one or more antibactericidal agents and/or preservatives may be included in the formulation of the contrast medium, such as sodium benzoate, all quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, for example, intravascularly or intraperitoneally. The appropriate means of sterilization will be apparent to the artisan instructed by the present description of the stabilized gas filled vesicles and their use. The contrast medium is generally stored as an aqueous suspension but in the case of dried vesicles the contrast medium may be stored as a dried powder ready to be reconstituted prior to use.

The novel compositions of the present invention, and especially the vesicle compositions, are useful as contrast media in diagnostic imaging, and are also suitable for use in all areas where diagnostic imaging is employed. However, the stabilized vesicles are particularly useful for perfusion imaging.

Diagnostic imaging is a means to visualize internal body regions of a patient. Diagnostic imaging includes, for example, ultrasound (US), magnetic resonance imaging (MRI), nuclear magnetic resonance (NMR), computed tomography (CT), electron spin resonance (ESR), nuclear medicine when the contrast medium includes radioactive material, and optical imaging, particularly with a fluorescent contrast medium. Diagnostic imaging also includes promoting the rupture of the vesicles via the methods of the present invention. For example, ultrasound may be used to visualize the vesicles and verify the localization of the vesicles in certain tissue. In addition, ultrasound may be used to promote rupture of the vesicles once the vesicles reach the intended target, including tissue and/or receptor destinations, thus releasing a bioactive agent and/or diagnostic agent.

In accordance with the present invention, there are provided methods of imaging a patient generally, and/or in specifically diagnosing the presence of diseased tissue in a patient. The imaging process of the present invention may be carried out by administering a contrast medium of the invention to a patient, and then scanning the patient using, for example, ultrasound, computed tomography, and/or magnetic resonance imaging, to obtain visible images of an internal region of a patient and/or of any diseased tissue in that region. The term region of a patient refers to the whole patient or a particular area or portion of the patient. The contrast medium may be particularly useful in providing images of tissue, such as myocardial, endothelial, and/or epithelial tissue, as well as the gastrointestinal and cardiovascular regions, but can also be employed more broadly, such as in imaging the vasculature or in other ways as will be readily apparent to those skilled in the art. Cardiovascular region, as that phrase is used herein, denotes the region of the patient defined by the heart and the vasculature leading directly to and from the heart. The phrase vasculature, as used herein, denotes the blood vessels (arteries, veins, etc.) in the body or in an organ or part of the body. The patient can be any type of mammal, but most preferably is a human.

The present invention also provides a method of diagnosing the presence of diseased tissue. Diseased tissue includes, for example, endothelial tissue which results from vasculature that supports diseased tissue. As a result, the localization and visualization of endothelial tissue to a region of a patient which under normal circumstances is not associated with endothelial tissue provides an indication of diseased tissue in the region.

In carrying out the magnetic resonance imaging method of the present invention, the contrast medium can be used alone, or in combination with other diagnostic, therapeutic or other agents. Such other agents include excipients such as flavoring or coloring materials. The magnetic resonance imaging techniques which are employed are conventional and are described, for example, in D. M. Kean and M. A. Smith, *Magnetic Resonance Imaging: Principles and Applications*, (William and Wilkins, Baltimore 1986). Contemplated MRI techniques include, but are not limited to, nuclear magnetic resonance (NMR) and electronic spin resonance (ESR). The preferred imaging modality is NMR.

In addition to the bioactive agents discussed above, the compositions of the present invention, and especially vesicle compositions, may be employed to deliver to a patient a wide variety of other active ingredients. For example, in addition to a variety of therapeutic agents which may be incorporated in the present compositions, there are a number of agents which may be classified as cosmetic agents that may be administered to a patient with the compositions of the present invention. Such administration may involve, for example, topical or subcutaneous administration. The various types of cosmetic formulations to which the compositions of the present invention, and especially vesicle compositions, are applicable and to which they may be advantageously adapted, include, among others, cosmetic creams, ointments, lotions, skin softeners, gels, blush, eyeliners, mascaras, acne-medications, cold creams, cleansing creams, and oleaginous foams. Cosmetic agents which may be incorporated into the compositions of the present invention include, for example, Vitamin A, Vitamin C, Vitamin D, Vitamin E, Vitamin K, Beta Carotene, collagen, elastin, retinoic acid, retinol palmitate, aloe vera, lanolin, hyaluronic acid, and nucleosides. If desired, the cosmetic formulations may also comprise a gas or gaseous precursor, as discussed above in connection with, for example, the vesicle compositions.

The present compositions may also be used for administering sunscreen agents to a selected tissue. Such sunscreen agents include but are not limited to: 4% benzyl salicylate and benzyl cinnamate (2% each); 5% cycloform (isobutyl-p-aminobenzoate); 5% diallyl trioleate; 2.5% monoglyceryl p-aminobenzoate; 4% propylene glycol p-aminobenzoate; and other photoabsorptive compounds.

For applications involving cosmetics and to a lesser extent for therapeutic agents, particularly topical applications, a coloring agent may also be desirably incorporated in the compositions. Suitable coloring agents include, for example, Violet 1, FD&C Blue #1, FD&C Green #33 as well as FD&C Red #44. Natural colors may also be used in cosmetic formulations including, for example, alkanet, annatto, carotene, chlorophyll, cochineal, saffron and tumeric.

A skin absorption enhancing agent may also be incorporated into the compositions. Such skin absorption enhancers include, for example, the following: pyrrolidones, such as 2 pyrrolidone, N-methyl-2-pyrrolidone (NMP), 1-methyl-2-pyrrolidone, 5-methyl-2-pyrrolidone, 1-ethyl-2-pyrrolidone, 2-pyrrolidone-5-carboxylic acid, N-hydroxyethylpyrrolidone (HEP), N-cyclohexylpyrrolidone (CHP), N-dimethylaminopropylpyrrolidone (DAPP), N-tallowalkylpyrrolidone (TAP), 1-lauryl-2-pyrrolidone (LP), and 1-hyxyl-2-pyrrolidone (HP); fatty acids, such as oleic acid, linoleic acid, heptanoic acid, caproic acid, lauric acid, stearic acid, octadecenoic acid, palmitoleic acid, myristic acid and palmitelaidic acid; sulfoxides, such as dimethylsulfoxide (DMSO), dimethylacetamide (DMAC), dimethylformamide (DMF), N-methylformamide (NMF) and decylmethylsulfoxide (DCMS); amines and derivatives thereof, such as N,N-diethyl-m-toluamide, dodecylamine, ethoxylated amine, N,N-bis(2-hydroxyethyl)oleylamine, dodecyl-N,N-dimethylamino acetate, sodium pryoglutaminate and N-hydroxylethalacetamide; terpenes and terpenoids, such as Δ-pinenes, δ-limonene, 3-carene, α-terpineol, terpinen-4-ol, careol, abisabolol, carvone, pulegone, piperitone, menthone, fenchone, cyclohexene oxide, limonene oxide, pinene oxide, cyclopentene oxide, ascaridol, 7-oxabicyclo[2.2.1]heptane, 1,8-cineole, safrole, 1-carvone, terpenoid cyclohexanone derivatives, acyclic terpenehydrocarbon chains, hydrocarbon terpenes, cyclic ether terpenes, cardamon seed extract, monoterpene terpineol and acetyl terpineol; essential oils of eucalyptus, chenopodium and yang ylang; surfactants, including anionic surfactants, such as sodium laurylsulfate (SLS), phenylsulfurate CA, calcium dodecylbenzene sulfonate, empicol ML26/F and magnesiumlaurylsulfate, cationic surfactants, such as cetyltrimethylammonium bromide, nonionic surfactants, such as NP series and PE series and the polysorbates or zwiterionic surfactants, such as N-dodecyl-N,N-dimethylbetaine; alcohols, such as ethanol, lauryl alcohol, linolenyl alcohol, 1-octanol, 1-propanol and 1-butanol; urea, cyclic unsaturated urea analogs, glycols, azone, n-alkanols, n-alkanes, orgelase, alphaderm cream and water. If desired, the aforementioned materials may be included in a base which can be composed of various substances including, for example, glycerol, propylene glycol (PG), isopropyl myristate, urea (in a propylene glycol, ethanol and water medium) or polyethylene glycol (PEG).

The compositions of the present invention which are formulated as cosmetics may be administered to a patient in any of a variety of ways, with topical and subcutaneous administration being preferred. While topical administration will ordinarily and predominantly be to the skin of a patient, it is not limited thereto, but includes application to any and all tissue surfaces of a patient whether internal or external. Thus, in addition to a patient's skin, other sites of topical administration include various mucosal membranes, such as those of the eyes, nose, mouth, rectum and vagina. Application to the tissue surface sites is topical (that is, to the place applied), but there may also be further delivery as a result of absorption and transfer to other tissues, especially systemic delivery via the blood, from the site of topical administration.

Similarly, subcutaneous administration will ordinarily and predominantly be delivery underneath the skin of a patient by way of injection or the like. However, it is also not limited thereto, but includes application below any and all tissue surfaces of a patient whether internal or external. Thus, in addition to administration below a patient's skin, other sites of subcutaneous administration include beneath the various mucosal membranes, such as those of the eyes, nose, mouth, rectum and vagina. Delivery to these sites is typically local (that is, to the place applied), but there may also be further delivery as a result of absorption and transfer to other tissues, especially systemic delivery via the blood, from the local place of subcutaneous administration. It should be noted in particular that absorption and transfer of therapeutic and cosmetic agents to other tissues can be achieved for longer periods of time through the use of subcutaneous depot injections. Generally with subcutaenous injections, the injections are typically immediately below the tissue surface, and are generally injected at a depth of up to about 3.0 cm. Preferably, the depth of the subcutaneous injections are from about 0.05 to about 1.0 cm, more preferably from about 0.1 mm to about 1 mm, even more preferably from about 0.1 to about 0.5 mm, and still more preferably about 0.2 mm.

It is contemplated that the silicon amphiphilic compounds of the present invention may possess physical properties such as relatively high viscosities at room temperature and low surface tensions, as well as substantial resistance to scission by ionic substances, such as acids, alkalis, and the like. In view of these properties, the present silicon amphiphilic compounds and compositions containing them may be utilized in industrial applications such as, for example, lubricants, antifoams, greases and the like. In addition to the medical, diagnostic and therapeutic utilities described above, the compounds of the present invention may also have utility in connection with topically applied insecticides. Furthermore, they may be suited for use as base polymers in organoperoxide-curing silicone rubber compositions, addition reaction-curing silicone rubber compositions and condensation reaction-curing silicone rubber compositions. The silicon compounds described herein may be used as starting materials in connection with organosilicon group-endblocked organic polymers, the latter of which may be used as surfaces, films and coatings in semiconductor wafer fabrication and related uses in mask technology for the directed synthesis of biological polymers.

The present invention is further described in the following examples. In these examples, Examples 1 to 8 are actual examples, while Examples 9 to 15 are prophetic examples. These examples are for illustrative purposes only, and are not to be construed as limiting the appended claims.

Various of the starting materials used in the following examples are commercially available. Aminopropyldimethyl terminated polydimethylsiloxane and dimethylamine terminated polydimethylsiloxane were obtained from United Chemical Technologies, Inc. (Bristol, Pa.). 1,2-Dipalmitoyl-sn-glycero-3-succinate, 1,2-dipalmitoyl-sn-glycerol, dipalmitolylphosphatidic acid and dipalmitoylphosphatidylcholine were obtained from Avanti Polar Lipids (Alabaster, Ala.). ω-Hydroxy-α-aminopolyethylene glycol was obtained from Shearwater Polymers, Inc. (Huntsville, Ala.) and perfluoropropane and perfluorobutane were obtained from Flura Corporation (Newport, Tenn.).

In the following examples, "DPPE" refers to dipalmitoylphosphatidylethanolamine; "DPPA" refers to dipalmitolylphosphatidic acid; and "DPPC" refers to dipalmitoylphosphatidylcholine. "DPGS" refers to 1,2-dipalmitoyl-sn-glycero-3-succinate. "PEG" refers to poly(ethylene glycol) polymer. "DPG" refers to 1,2-dipalmitoyl-sn-glycerol. "PEG1000" refers to a poly(ethylene glycol) polymer having a molecular weight of about 1000. "DMAP" refers to 4dimethylaminopyridine and "DMF" refers to dimethylformamide. "HMDS" refers to 1,1,1,3,3,3-hexamethyldisilazane and "DCC" refers to dicyclohexylcarbodiimide.

The following examples are directed to the preparation of silicon amphiphilic compounds within the scope of the present invention.

EXAMPLE 1

This example is directed to the preparation of a compound of the following formula.

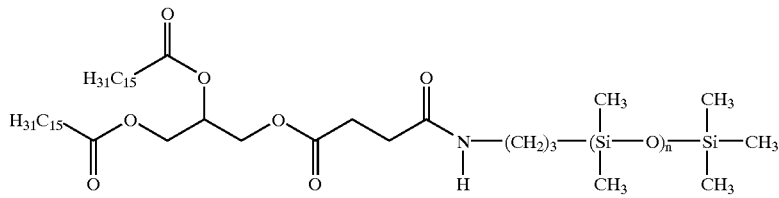

where n is 3 to 6.

To a solution of DPGS (335 mg, 0.05 mmol, 1 equiv.) in $CH_2Cl_2$ (25 mL) was added a solution of aminopropyldimethyl terminated polydimethylsiloxane (1250 mg, 0.5 mmol, 10 equiv.) in $CH_2Cl_2$ (25 mL). The resulting solution was cooled to 0–5° C. and a solution of DCC (110 mg, 0.54 mmol, 10.8 equiv.) in $CH_2Cl_2$ (25 mL) was added dropwise over a period of about one hour. The reaction mixture was stirred overnight at room temperature after which ice water (100 mL) was added and the resulting mixture was stirred an additional hour. The organic layer was separated, dried ($Na_2SO_4$), concentrated in vacuo, and lyophilized for 2 hours to yield a white, gel-like solid. Solid precipitate which was formed by adding hexane (60 mL) (Mallinckrodt, St. Louis, Mo.) was removed by filtration. Concentration of the filtrate afforded 1.42 g of the compound depicted above, a silicon amphiphilic compound within the scope of the present invention, as a gel-like solid.

IR ($cm^{-1}$): 1739, 1630, 1263.

EXAMPLE 2

This example is directed to the preparation of a compound of the following formula.

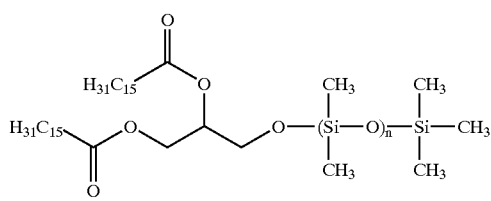

where n is 3 to 6

To a solution of dimethylamine terminated polydimethylsiloxane (250 mg, 0.44 mmol, 1 equiv.) in $CHCl_3$ (25 mL) was added a solution of DPG (250 mg, 0.44 mmol, 1 equiv.) in $CHCl_3$ (25 mL). The resulting mixture was heated to 40–50° C. and stirred for about 16 hours under an inert atmosphere ($N_2$). The reaction mixture was concentrated in vacuo and lyophilized for about 3 hours to provide 0.47 g of the compound depicted above, a silicon amphiphilic compound within the scope of the present invention, as a soft white material.

IR ($cm^{-1}$): 1730, 1260; TLC: $R_f$ of 0.85 (1:3 EtOAc:Hexane).

EXAMPLE 3

This example is directed to the preparation of a compound of the following formula.

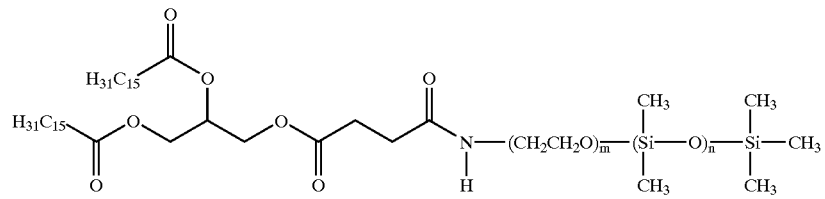

where n is 3 to 6.

A. Preparation of Intermediate Compound

This step is directed to the preparation of the following intermediate compound.

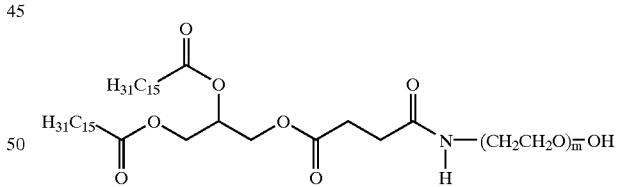

where n is 3 to 6.

To a solution of DPGS (98.5 mg, 0.15 mmol, 1 equiv.) in $CH_2Cl_2$ (10 mL) was added a solution of ω-hydroxy-α-amino-PEG (MW 3400) (500 mg, 0.15 mmol, 1 equiv.) in $CH_2Cl_2$ (10 mL). The resulting mixture was cooled to 0–5° C., and a solution of DCC (32.4 mg, 0.16 mmol) in $CH_2Cl_2$ (10 mL) was added dropwise over a period of about 30 minutes. The resulting mixture was stirred at room temperature for about 24 hours. Deionized water (50 mL) was added and stirring was continued for an additional 2 hours. The precipitated urea was removed by filtration. Concentration of the filtrate afforded a white solid (0.54 g) which was dissolved in acetonitrile (30 mL). Filtration followed by concentration of the filtrate afforded 0.45 g of the intermediate compound depicted above as a soft white material.

IR (cm$^{-1}$): 1740, 1650.

B. Preparation of Silicon Amphiphilic Compound

This step is directed to the preparation of the silicon amphiphilic compound.

The intermediate compound prepared in Step A (0.45 g, 0.11 mmol, 1 equiv.) was dissolved in CHCl$_3$ (30 mL) and a solution of dimethylamine terminated polydimethylsiloxane (66 mg, 0.11 mmol, 1 equiv.) in CHCl$_3$ (10 mL) was added. The resulting mixture was heated to 40–50° C. under an inert atmosphere (N$_2$) for about 16 hours. Removal of the solvent followed by lyophilization for about 2 hours afforded 0.48 g of the compound depicted above, a silicon amphiphilic compound within the scope of the present invention, as a yellow solid.

IR (cm$^{-1}$): 1740, 1670, 1260, 1100.

EXAMPLE 4

This example is directed to the preparation of a compound of the following formula.

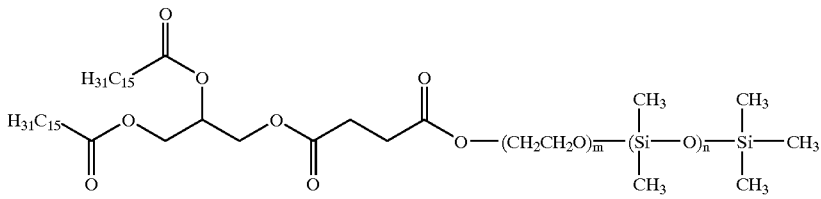

where n is 3 to 6.

A. Preparation of Intermediate Compound

This step is directed to the preparation of the following intermediate compound.

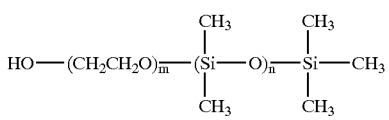

where n is 3 to 6.

To a solution of PEG. 1000 (5 g, 5 mmol, 1 equiv.) in CHCl$_3$ (30 mL) was added dropwise a solution of dimethylamine terminated polydimethylsiloxane (3 g, about 5 mmol, 1 equiv.) in CHCl$_3$ (30 mL). The resulting mixture was heated to 40–50° C. under an inert atmosphere (N$_2$) and stirred for about 16 hours. Removal of the solvent and concentration in vacuo for about 2 hours afforded 8 g of the intermediate compound depicted above.

IR (cm$^{-1}$): 1260, 1100.

B. Preparation of Silicon Amphiphilic Compound

This step is directed to the preparation of the silicon amphiphilic compound.

To a solution of the intermediate compound prepared in Step A (800 mg, 0.5 mmol, 1 equiv.) in CH$_2$Cl$_2$ (20 mL) was added a solution of 1,2-dipalmitoyl-sn-glycero-3-succinate (335 mg, 0.5 mmol, 1 equiv.) and DMAP (16 mg) in CH$_2$Cl$_2$ (20 mL). The reaction mixture was cooled to 0–5° C., and a solution of DCC (108 mg, 0.53 mmol) in CH$_2$Cl$_2$ (10 mL) was added dropwise over a period of about 5 hours. The resulting solution was stirred at room temperature for about 32 hours. The solid precipitate which had formed was removed by filtration, and the filtrate was diluted with ice water and stirred an additional 2 hours. The organic layer was separated, dried (Na$_2$SO$_4$) and concentrated. The resulting residue was diluted with methanol (30 mL) and the resulting mixture was stirred for about 2 hours and filtered. Concentration of the filtrate, followed by lyophilization for about 3 hours, afforded 0.59 g (51% yield) of the compound depicted above, a silicon amphiphilic compound within the scope of the present invention.

IR (cm$^{-1}$): 1740, 1260, 1100.

EXAMPLE 5

This example is directed to the preparation of a compound of the following formula.

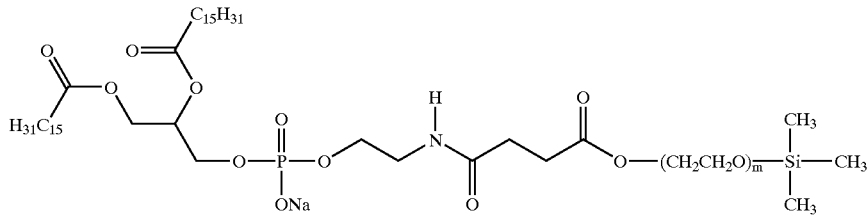

A. Preparation of Intermediate Compound A

This step is directed to the preparation of the following intermediate compound.

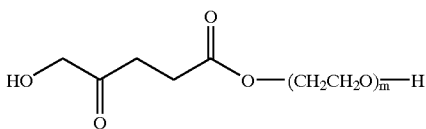

To a solution of terminal trimethylsilyl capped PEG 1000 (dehydrated by lyophilization for about 8 hours) (5 g, 5 mmol, 1 equiv.) in DMF (10 mL) was added dropwise a solution of succinic anhydride (5 mmol, 1 equiv.) and triethylamine (0.5 g, 5 mmol, 1 equiv.) in DMF (5 mL). The resulting mixture was stirred at about 50° C. for about 4 hours. The reaction mixture was cooled, washed with 10% HCl, and diluted with $H_2O$ (30 mL). The resulting mixture was extracted with $CHCl_3$ (50 mL) and the organic layer was washed with $H_2O$ (50 mL), dried ($Na_2SO_4$) and concentrated. The resulting oily residue was dissolved in $CHCl_3$ (5 mL). Dropwise addition of anhydrous ether (70 mL) (Mallinckrodt, St. Louis, Mo.) resulted in the precipitation of the crude intermediate compound. The supernatant was decanted, and the crude compound was washed twice with $Et_2O$ and dried to yield intermediate compound A as a white, cream-like material.

IR ($cm^{-1}$): 1730, 1670.

B. Preparation of Intermediate Compound B

This step is directed to the preparation of the following intermediate compound.

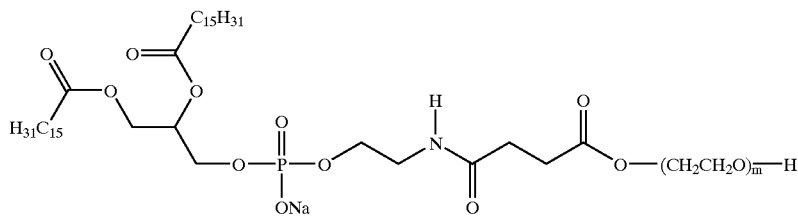

A mixture of intermediate compound A (550 mg, 0.5 mmol, 1 equiv.) and DCC (103 mg, 0.5 mmol, 1 equiv.) in $CHCl_3$ (30 mL) was stirred at 0–10° C. for about 2 hours. To this solution was added a suspension of DPPE (346.5 mg, 0.5 mmol, 1 equiv.) and triethylamine (50 mg, 0.5 mmol, 1 equiv.) in $CH_2Cl_2$ (30 mL) at 0–5° C. The reaction mixture was then stirred overnight at room temperature. Removal of the precipitate by filtration, followed by concentration of the filtrate, afforded 0.7 g of intermediate compound B.

IR ($cm^{-1}$): 1730, 1690, 1100.

C. Preparation of Silicon Amphiphilic Compound

This step is directed to the preparation of the silicon amphiphilic compound.

A solution of intermediate compound B (360 mg) in $CHCl_3$ (30 mL) was combined with a solution of HMDS (260 mg) in $CHCl_3$ (10 mL). This mixture was heated to 40–50° C. for about 16 hours under an inert atmosphere ($N_2$). Concentration of the reaction mixture, followed by lyophilization for about 4 hours, afforded 0.32 g of the compound depicted above, a silicon amphiphilic compound within the scope of the present invention.

The following examples are directed to the preparation of vesicle compositions within the scope of the present invention.

EXAMPLE 6

The silicon amphiphilic compound of Example 1 (343 mg; approximate molecular weight of 3,151), DPPC (820 mg), DPPA (91.2 mg) and $CHCl_3$ (50 mL) were combined to provide a final molar ratio of lipids of 82 mole % DPPC, 10 mole % DPPA and 8 mole % silicon amphiphilic compound. The mixture was concentrated, lyophilized and suspended in 5 mL of a mixture of normal saline, propylene glycol and glycerol (8:1:1). A portion (1.5 mL) of this mixture, at a lipid. concentration of 1 mg/mL, was added to a 2 mL glass tubing vial (Wheaton Glass Products, Millville, N.J.). The head space of the vial was filled with perfluoropropane and the bottle was stoppered, sealed, and placed on an ESPE Capmix (ESPE, Seefeld, Germany) and shaken for 60 seconds at 4,300 RPM. The resulting gas filled vesicles were sized using a Model 770 AccuSizer (Particle Sizing Systems, Santa Barbara, Calif.). This revealed that the concentration of vesicles was about $1.6 \times 10^7$ vesicles/mL, and the vesicles had a mean diameter of about 6.96 μm. Evaluation of the vesicle composition for acoustic activity using a custom built bench top acoustic lab revealed that the vesicles exhibited desirable backscatter and pressure stability.

EXAMPLE 7

The procedure described in Example 6 was repeated, except that the silicon amphiphilic compound of Example 1 was replaced with the silicon amphiphilic compound prepared in Example 2. The concentration of vesicles in the resulting vesicle composition was about $9.16 \times 10^8$ vesicles/mL, and the vesicles had a mean diameter of about 2.96 μm.

EXAMPLE 8

The procedure described in Example 7 was repeated, except that the perfluoropropane was replaced with perfluorobutane. The resulting composition had a vesicle concentration of about 9.4×108 vesicles/mL, with a vesicle mean diameter of about 2.69 μm.

EXAMPLE 9

This example is directed to the preparation of a compound of the following formula.

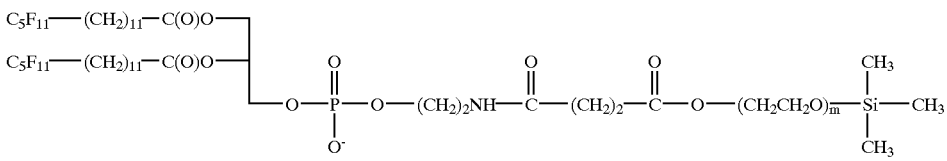

A. Preparation of Intermediate Compound

A fluorinated amphiphilic compound having the following general formula

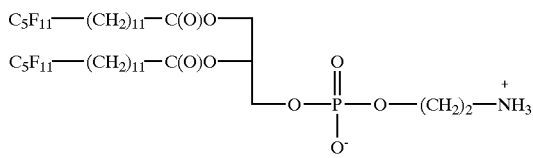

will be synthesized as described in copending U.S. application Ser. No. 08/465,868, filed Jun. 6, 1995 and C. Santaella et al., *New Journal of Chemistry*, Vol. 15, p. 685 (1991), the disclosures of which are incorporated herein by reference, in their entirety.

B. Preparation of Intermediate Compound

This step is directed to the preparation of the following intermediate compound.

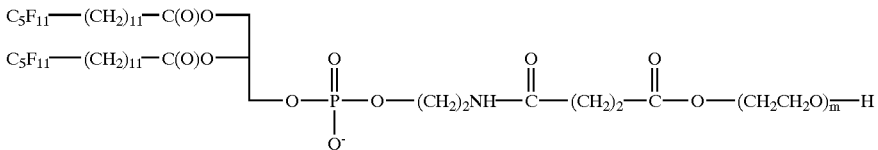

A mixture of the intermediate compound of Example 5A (550 mg, 0.5 mmol, 1 equiv.) and DCC (103 mg, 0.5 mmol, 1 equiv.) in $CHCl_3$ (30 mL) will be stirred at 0–10° C. for about 2 hours. To the resulting solution will be added a suspension of the intermediate compound prepared in Step A of this example (550 mg, 0.5 mmol, 1 equiv.), triethylamine (50 mg, 0.5 mmol, 1 equiv.) and $CH_2Cl_2$ (30 mL) at 0–5° C. The resulting mixture will be stirred overnight at room temperature. Removal of the precipitate by filtration, followed by concentration of the filtrate, will yield about 1 g of the intermediate compound depicted above.

C. Preparation of Silicon Amphiphilic Compound

This step is directed to the preparation of the silicon amphiphilic compound.

A solution of the intermediate from Step B in this example (520 mg) in $CHCl_3$ (30 mL) will be combined with a solution of HMDS (260 mg) in $CHCl_3$ (10 mL). The resulting mixture will be heated to 40–50° C. for about 16 hours under an inert atmosphere ($N_2$). The reaction mixture will be concentrated and lyophilized for about 4 hours to yield about 0.5 g of the compound depicted above, a silicon. amphiphilic compound within the scope of the present invention.

The following examples are directed to the preparation of vesicle compositions within the scope of the present invention.

EXAMPLE 10

A fluorinated phosphatidylcholine will be synthesized as described in copending U.S. application Ser. No. 08/465,868, filed Jun. 6, 1995 and C. Santaella et al., *New Journal of Chemistry*, Vol. 15, p. 685 (1991), the disclosures of which are incorporated herein by reference, in their entirety.

The fluorinated phosphatidylcholine (90 mole %), the fluorinated silicon amphiphilic compound prepared in Example 9 (10 mol %) and $CHCl_3$ will be combined at a total lipid concentration of 50 mg/mL. This lipid mixture will be lyophilized and the lyophilized lipids will be suspended in phosphate buffered normal saline. The resulting mixture will be heated to 80° C. and sonicated for 10 minutes using a Heat Systems Probe Sonicator (Farmingdale N.Y.), at level 4. The resulting fluorinated phospholipid vesicles will be cooled to room temperature and their size will be determined by an Accusizer. The fluorinated liposomes will range in size from about 30 to about 500 nm.

EXAMPLE 11

Egg phosphatidylcholine and cholesterol (8:2) and the silicon amphiphilic compound prepared in Example 5 (5% of total lipid) will be combined in chloroform. The resulting mixture will be concentrated in vacuo and rehydrated with an aqueous solution of doxorubicin hydrochloride (0.5 M). The resulting mixture will be stirred for one hour, subjected to three freeze-thaw cycles, and extruded eight times through a polycarbonate membrane (100 nm). The resulting solution will be dialyzed through a membrane (5000 MW CO) to separate unencapsulated doxorubicin. The resulting vesicle composition will be useful as a therapeutic delivery agent.

EXAMPLE 12

Egg phosphatidylcholine and cholesterol (7:3) and the silicon amphiphilic compound prepared in Example 4 (3% of total lipid employed) will be combined in chloroform. The resulting mixture will be concentrated in vacuo and rehydrated with an aqueous solution of gadolinium DTPA (0.5 M). The resulting mixture will be stirred for one hour, subjected to three freeze-thaw cycles, and extruded eight times through a polycarbonate membrane (100 nm). The resulting solution will be dialyzed through a membrane (5000 MW CO) to separate unencapsulated gadolinium DTPA. The resulting vesicle composition will be useful as an MRI contrast agent.

EXAMPLE 13

Example 12 will be repeated, except that iohexol will be substituted for gadolinium DTPA. The resulting vesicle composition may be used as a CT contrast agent.

EXAMPLE 14

Example 12 will be repeated except that Tc-99m pentaacetate (DTPA) will be substituted for gadolinium DTPA. The resulting vesicle composition may be used in radiopharmaceutical applications.

EXAMPLE 15

Lecithin (natural or hydrogenated) and the silicon amphiphilic compound prepared in Example 3 (3% of total lipid employed) will be combined in chloroform. The resulting mixture will be concentrated in vacuo, and the residue obtained will be rehydrated with an aqueous mixture of fragrant materials, vitamins and other nutritional materials such as placenta, a-tocopherol acetate, L-ascorbyl magnesium phosphate and bovine serum extract, UV absorber, and the like. The resulting mixture will be stirred for one hour, sonicated and combined with suitable cosmetic additives and/or excipients, for example, cosmetic creams, ointments and/or lotions, as well as suitable coloring additives, to provide a cosmetic formulation.

The disclosures of each patent, patent application and publication cited or described in this document are hereby incorporated by reference, in their entirety.

Various modifications of the invention, in addition to those described herein, will be apparent to those skilled in the art from the foregoing description. Such modifications are also intended to fall within the scope of the appended claims.

What is claimed is:

1. A compound of the formula:

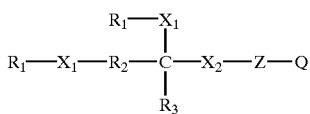

(I)

wherein:

each $X_1$ is independently —O—, —S—, —SO—, —SO$_2$—, —NR$_4$—, —X$_3$—C(=X$_4$)—, —C(=X$_4$)—X$_3$— or —C(=X$_4$)—;

$X_2$ is —R$_5$—X$_3$—R$_6$—, —R$_5$—X$_3$—C(=X$_4$)—R$_6$—, —R$_5$—C(=X$_4$)—X$_3$—R$_6$—, —R$_5$—X$_3$—C(=X$_4$)—R$_6$—C(=X$_4$)—X$_5$—R$_7$—,

—R$_5$—X$_3$—(YX$_3$)P(=X$_4$)—X$_3$—R$_6$—X$_5$—C(=X$_4$)—R$_6$—C(=X$_4$)—X$_3$— or a saccharide diradical;

each $X_3$ is independently a direct bond, —O—, —NR$_4$— or —S—;

each $X_4$ is independently O or S;

each $X_5$ is independently —O—, —NR$_4$— or —S—;

Y is hydrogen or a pharmaceutically acceptable counter ion;

Z is a direct bond or a hydrophilic polymer;

Q is a silicon residue;

each $R_1$ is independently optionally substituted alkyl of 1 to about 50 carbons;

$R_2$ is alkylene of 1 to about 30 carbons;

each of $R_3$ and $R_4$ is independently hydrogen or alkyl of 1 to about 10 carbons; and each of $R_5$, $R_6$ and $R_7$ is independently a direct bond or alkylene of 1 to about 30 carbons.

2. A compound according to claim 1 wherein:

Q is a residue of the formula —X$_6$—[Si(R$_8$)$_2$—X$_3$—Z]$_n$—Si(R$_8$)$_3$ wherein:

n is an integer from 0 to about 10,000;

$X_6$ is a direct bond, —O—, —NR$_5$— or —S—; and each $R_8$ is independently alkyl of 1 to about 10 carbons.

3. A compound according to claim 2 wherein:

each $X_1$ is independently —O—, —NR$_4$—, —X$_3$—C(=X$_4$)—, —C(=X$_4$)-X$_3$— or —C(=X$_4$)—; and $X_2$ is —R$_5$—X$_3$—R$_6$—, —R$_5$—X$_3$—C(=X$_4$)—R$_6$—C(=X$_4$)—X$_5$—R$_7$— or —R$_5$—X$_3$—(YX$_3$)P(=X$_4$)—X$_3$—R$_6$—X$_3$—C(=X$_4$)—R$_6$—C(=X$_4$)—X$_3$—.

4. A compound according to claim 3 wherein:

each $X_1$ is independently —O—, —X$_3$—C(=X$_4$)— or —C(=X$_4$)—X$_3$—.

5. A compound according to claim 4 wherein:

$X_1$ is —C(=X$_4$)—X$_3$—;

$X_3$ is —O—;

$X_4$ is O;

$X_5$ is —O— or —NR$_4$—; and $X_6$ is a direct bond or —O—.

6. A compound according to claim 5 wherein:

n is an integer from 0 to about 1,000.

7. A compound according to claim 6 wherein:

n is an integer from 0 to about 100.

8. A compound according to claim 7 wherein:

each $R_1$ is independently optionally substituted alkyl of 1 to about 30 carbons;

$R_2$ is alkylene of 1 to about 15 carbons;

each of $R_3$ and $R_4$ is independently hydrogen or alkyl of 1 to about 4 carbons;

each of $R_5$, $R_6$ and $R_7$ is independently a direct bond or alkylene of 1 to about 15 carbons; and each $R_8$ is independently alkyl of 1 to about 4 carbons.

9. A compound according to claim 8 wherein:

each $R_1$ is independently optionally substituted alkyl of 1 to about 20 carbons;

$R_2$ is alkylene of 1 to about 10 carbons;

$R_3$ and $R_4$ are hydrogen;

each of $R_5$, $R_6$ and $R_7$ is independently a direct bond or alkylene of 1 to about 10 carbons; and $R_8$ is methyl.

10. A compound according to claim 9 wherein:

$R_2$ is alkylene of 1 to about 5 carbons; and each of $R_5$, $R_6$ and $R_7$ is independently a direct bond or alkylene of 1 to about 5 carbons.

11. A compound according to claim 10 wherein:

$R_2$ is methylene.

12. A compound according to claim 11 wherein:

n is an integer from 0 to about 10.

13. A compound according to claim 12 wherein:

n is an integer. from 1 to about 8.

14. A compound according to claim 13 wherein:

n is an integer from about 3 to about 6.

15. A compound according to claim 14 wherein:

each $R_1$ is independently optionally substituted alkyl of 1 to about 15 carbons.

16. A compound according to claim 15 wherein:

Z is a direct bond.

17. A compound according to claim 16 wherein:
$X_2$ is —$R_5$—$X_3$—$R_6$—; and
$X_6$ is —O—.
18. A compound according to claim 17 wherein:
$R_5$ is methylene; and
$R_6$ is a direct bond.
19. A compound according to claim 16 wherein:
$X_2$ is —$R_5$—$X_3$—C(=$X_4$)—$R_6$—C(=$X_4$)—$X_5$—$R_7$—.
20. A compound according to claim 19 wherein:
$X_5$ is —$NR_4$—; and
$X_6$ is —O—.
21. A compound according to claim 20 wherein:
$R_5$ is methylene;
$R_6$ is ethylene; and
$R_7$ is propylene.
22. A compound according to claim 15 wherein:
Z is a hydrophilic polymer.
23. A compound according to claim 22 wherein:
Z is selected from the group consisting of polyethylene glycol, polyvinyl alcohol or polyvinyl pyrrolidone.
24. A compound according to claim 23 wherein:
Z is polyethylene glycol.
25. A compound according to claim 24 wherein:
$X_2$ is —$R_5$—$X_3$—C(=$X_4$)—$R_6$—C(=$X_4$)—$X_5$—$R_7$—.
26. A compound according to claim 25 wherein:
$R_5$ is methylene;
$R_6$ is ethylene; and
$R_7$ is a direct bond.
27. A compound according to claim 26 wherein:
$X_6$ is —O—.
28. A compound according to claim 27 wherein:
$X_5$ is —$NR_4$—.
29. A compound according to claim 27 wherein:
$X_5$ is —O—.
30. A compound according to claim 12 wherein:
n is 0.
31. A compound according to claim 30 wherein:
Z is a hydrophilic polymer.
32. A compound according to claim 31 wherein:
Z is selected from the group consisting of polyethylene glycol, polyvinyl alcohol or polyvinyl pyrrolidone.
33. A compound according to claim 32 wherein:
Z is polyethylene glycol.
34. A compound according to claim 33 wherein:
$X_2$ is —$R_5$—$X_3$—(Y$X_3$)P(=$X_4$)—$X_3$—$R_6$—$X_5$—C(=$X_4$)—$R_6$—C(=$X_4$)—$X_3$—.
35. A compound according to claim 34 wherein:
$X_5$ is —$NR_4$—; and
$X_6$ is a direct bond.
36. A compound according to claim 35 wherein:
$R_5$ is methylene; and
$R_6$ is ethylene.
37. A compound according to claim 36 wherein:
each $R_1$ is independently optionally substituted alkyl of 1 to about 15 carbons.
38. A compound according to claim 37 wherein:
each $R_1$ is independently substituted alkyl of 1 to about 15 carbons.
39. A compound according to claim 38 wherein:
said substituent of said substituted alkyl is halogen.
40. A compound according to claim 39 wherein: said halogen is fluorine.
41. A compound according to claim 40 wherein: $R_1$ comprises perfluorinated alkyl.
42. A compound according to claim 41 wherein:
said perfluorinated alkyl has the formula $C_aF_{2a+1}$—$(CH_2)_b$— wherein:
a is an integer from 1 to about 30; and
b is an integer from 0 to about 29;
provided that the sum of a and b is not greater than about 30.
43. A compound according to claim 42 wherein:
a is an integer from 1 to about 10; and
b is an integer from 1 to about 20.
44. A compound according to claim 43 wherein:
a is an integer from about 3 to about 8; and
b is an integer from about 5 to about 15.
45. A compound according to claim 44 wherein:
a is an integer from about 4 to about 6; and
b is an integer from about 9 to about 13.
46. A compound according to claim 45 wherein:
a is an integer from about 3 to about 8; and
b is an integer from about 5 to about 15.
47. A compound according to claim 46 wherein:
a is an integer from about 4 to about 6; and
b is an integer from about 9 to about 13.
48. A compound according to claim 47 wherein:
a is about 5; and
b is about 11.
49. A silicon amphiphilic compound which comprises a silicon residue.
50. A silicon amphiphilic compound according to claim 49 wherein aid silicon residue comprises at least one silicon atom.
51. A silicon amphiphilic compound according to claim 50 wherein said silicon residue comprises from 1 to about seven 7 silicon atoms.
52. A silicon amphiphilic compound according to claim 51 wherein said silicon residue comprises at least one siloxy group.
53. A compound according to claim 52 which comprises from 1 to about 6 siloxy groups.
54. A silicon amphiphilic compound according to claim 49 which is fluorinated.
55. A silicon amphiphilic compound according to claim 54 wherein at least a portion of the compound is polyfluorinated.
56. A silicon amphiphilic compound according to claim 55 wherein said polyfluorinated portion is perfluorinated.
57. A composition for diagnostic imaging comprising a silicon amphiphilic compound and a gas or gaseous precursor.
58. A composition according to claim 57 which comprises a vesicle composition.
59. A composition according to claim 58 wherein said vesicles are selected from the group consisting of micelles and liposomes.
60. A composition according to claim 59 wherein said vesicles comprise gas filled vesicles.
61. A composition according to claim 60 wherein said gas is selected from the group consisting of air, nitrogen, carbon dioxide, oxygen, helium, argon, xenon, neon and fluorine.
62. A composition according to claim 60 wherein said gas comprises a fluorinated gas.
63. A composition according to claim 62 wherein said fluorinated gas is selected from the group consisting of a perfluorocarbon, sulfur hexafluoride and heptafluoropropane.

64. A composition according to claim 63 wherein said fluorinated gas comprises a perfluorocarbon.

65. A composition according to claim 64 wherein said perfluorocarbon is selected from the group consisting of perfluoromethane, perfluoroethane, perfluoropropane, perfluorobutane and perfluorocyclobutane.

66. A composition according to claim 65 wherein said perfluorocarbon gas is selected from the group consisting of perfluoropropane and perfluorobutane.

67. A composition according to claim 66 wherein said perfluorocarbon gas comprises perfluoropropane.

68. A composition according to claim 66 wherein said perfluorocarbon gas comprises perfluorobutane.

69. A composition according to claim 57 wherein said gaseous precursor has a boiling point of greater than about 37° C.

70. A composition according to claim 69 wherein said gaseous precursor comprises a fluorinated compound.

71. A composition according to claim 70 wherein said fluorinated compound comprises a perfluorocarbon.

72. A composition according to claim 70 wherein said perfluorocarbon is selected from the group consisting of perfluoropentane, perfluorohexane and perfluoroheptane.

73. A composition according to claim 57 further comprising a stabilizing material.

74. A composition according to claim 73 wherein said stabilizing material comprises a lipid.

75. A composition according to claim 74 wherein said lipid comprises a phospholipid.

76. A composition according to claim 75 wherein said phospholipid is selected from the group consisting of phosphatidylcholine and phosphatidic acid.

77. A composition according to claim 76 wherein said phosphatidylcholine is selected from the group consisting of dioleoylphosphatidylcholine, dimyristoylphosphatidylcholine, dipalmitoylphosphatidylcholine and distearoylphosphatidylcholine.

78. A composition according to claim 77 wherein said phosphatidylcholine comprises dipalmitoylphosphatidylcholine.

79. A composition according to claim 76 wherein said phosphatidic acid comprises dipalmitolylphosphatidic acid.

80. A composition according to claim 57 wherein said diagnostic imaging is selected from the group consisting of ultrasound imaging, computed tomography imaging and magnetic resonance imaging.

81. A composition according to claim 80 wherein said diagnostic imaging comprises ultrasound imaging.

82. A composition according to claim 57 further comprising a bioactive or cosmetic agent.

83. A cosmetic formulation comprising, in combination with a cosmetic agent, a composition comprising a silicon amphiphilic compound and a gas or gaseous precursor.

84. A method for the preparation of a composition which comprises a silicon amphiphilic compound and a gas or gaseous precursor, wherein the method comprises agitating, in the presence of a gas or gaseous precursor, an aqueous mixture of a silicon amphiphilic compound.

85. A composition according to claim 74 wherein said lipid is selected from the group consisting of unilamellar lipids, oligolamellar lipids and multilamellar lipids.

86. A composition a according to claim 85 wherein said lipids comprise unilamellar lipids.

87. A composition according to claim 86 wherein said lipid comprises one monolayer.

88. A composition according to claim 86 wherein said lipid is a phospholipid.

89. A composition according to claim 87 wherein said lipid is a phospholipid and said gas or gaseous precursor is sulfur hexafluoride.

90. A composition according to claim 87 wherein said lipid is a phospholipid and said gas or gaseous precursor is perfluoropentane.

91. A composition according to claim 87 wherein said lipid is a phospholipid and said gas or gaseous precursor is perfluoropropane.

92. A composition according to claim 86 wherein said lipid comprises one bilayer.

93. A composition according to claim 92 wherein said lipid is a phospholipid.

94. A composition according to claim 92 wherein said lipid is a phospholipid and said gas or gaseous precursor is sulfur hexafluoride.

95. A composition according to claim 92 wherein said lipid is a phospholipid and said gas or gaseous precursor is perfluoropentane.

96. A composition according to claim 92 wherein said lipid is a phospholipid and said gas or gaseous precursor is perfluoropropane.

97. A composition according to claim 86 wherein said lipids are selected from the group consisting of oligolamellar lipids and multilamellar lipids.

98. A composition according to claim 97 wherein said lipids comprise one monolayer.

99. A composition according to claim 98 wherein said lipid is a phospholipid.

100. A composition according to claim 98 wherein said lipid is a phospholipid and said gas or gaseous precursor is sulfur hexafluoride.

101. A composition according to claim 98 wherein said lipid is a phospholipid and said gas or gaseous precursor is perfluoropentane.

102. A composition according to claim 98 wherein said lipid is a phospholipid and said gas or gaseous precursor is perfluoropropane.

103. A composition according to claim 97 Wherein said lipids comprise one bilayer.

104. A composition according to claim 103 wherein said lipid is a phospholipid.

105. A composition according to claim 103 wherein said lipid is a phospholipid and said gas or gaseous precursor is sulfur hexafluoride.

106. A composition according to claim 103 wherein said lipid is a phospholipid and said gas or gaseous precursor is perfluoropentane.

107. A composition according to claim 103 wherein said lipid is a phospholipid and said gas or gaseous precursor is perfluoropropane.

108. A composition according to claim 74 wherein said lipid is a polymerized lipid.

109. A composition according to claim 74 which further comprises polyethylene glycol.

110. A compound according to claim 1 which is in a lyophilized form.

111. A silicon amphiphilic compound according to claim 49 which is in a lyophilized form.

112. A composition according to claim 57 which has been reconstituted from a lyophilized composition.

113. A composition according to claim 57 which further comprises a surfactant.

114. A composition according to claim 113 wherein said gas or gaseous precursor is selected from the group consisting of nitrogen, sulfur hexafluoride, perfluoromethane, perfluoroethane, perfluoropropane, perfluorocylcopropane, perfluorobutane, perfluorocyclobutane, perfluoropentane, perfluorocyclopentane, perfluorohexane, perfluoroheptane, perfluorooctane and perfluorononane.

115. A composition according to claim 114 wherein said gas or gaseous precursor is a combination of nitrogen and perfluorohexane.

116. A composition according to claim 114 wherein said gas or gaseous precursor is a combination of nitrogen and perfluoropropane.

117. A composition according to claim 58 wherein said vesicles comprise a surfactant.

118. A composition according to claim 117 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

119. A composition according to claim 118 wherein said gas or gaseous precursor is a combination of nitrogen and perfluorohexane.

120. A composition according to claim 118 wherein said gas or gaseous precursor is a combination of nitrogen and perfluoropropane.

121. A method according to claim 84 wherein said composition is reconstituted from a lyophilized composition.

122. A method according to claim 84 wherein said aqueous mixture further comprises a surfactant.

* * * * *

UNITED STATES PATENT AND TRADEMARK OFFICE
CERTIFICATE OF CORRECTION

PATENT NO. : 6,414,139 B1
DATED : July 2, 2002
INVENTOR(S) : Unger et al.

It is certified that error appears in the above-identified patent and that said Letters Patent is hereby corrected as shown below:

Column 14,
Line 67, delete "I" after "$R_1$";

Column 15,
Line 1, delete "R," and insert therefore -- $R_1$ --;

Column 46,
Line 40, delete "xa," and insert therefore -- $x_a$, --;

Column 64,
Line 58, delete "9.4x108" and insert therefore -- $9.4 \times 10^8$ --;

Column 72,
Line 39, delete "Wherein" and insert therefore -- wherein --;

Signed and Sealed this

Twenty-seventh Day of January, 2004

JON W. DUDAS
*Acting Director of the United States Patent and Trademark Office*